(12) United States Patent
Almhjell et al.

(10) Patent No.: US 12,421,534 B2
(45) Date of Patent: Sep. 23, 2025

(54) ENGINEERED ENZYMES AND METHOD FOR THE SYNTHESIS OF DIVERSE TYROSINE ANALOGS

(71) Applicant: California Institute of Technology, Pasadena, CA (US)

(72) Inventors: Patrick J. Almhjell, Pasadena, CA (US); Frances H. Arnold, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 17/985,033

(22) Filed: Nov. 10, 2022

(65) Prior Publication Data

US 2023/0313245 A1    Oct. 5, 2023

Related U.S. Application Data

(60) Provisional application No. 63/277,804, filed on Nov. 10, 2021.

(51) Int. Cl.
*C12P 13/22* (2006.01)
*C12N 9/88* (2006.01)

(52) U.S. Cl.
CPC .............. *C12P 13/225* (2013.01); *C12N 9/88* (2013.01); *C12Y 402/0102* (2013.01)

(58) Field of Classification Search
CPC .......... C12P 13/225; C12P 13/22; C12N 9/88; C12Y 402/0102; C12R 2001/01
See application file for complete search history.

(56) References Cited

U.S. PATENT DOCUMENTS

| | | | |
|---|---|---|---|
| 10,612,056 B2 * | 4/2020 | Boville | C12P 13/227 |
| 11,332,729 B2 * | 5/2022 | Romney | C12N 9/88 |
| 2018/0057806 A1 * | 3/2018 | Romney | C07D 209/20 |
| 2018/0327793 A1 * | 11/2018 | Boville | C07K 14/415 |
| 2019/0271016 A1 * | 9/2019 | Boville | C07D 209/08 |

FOREIGN PATENT DOCUMENTS

WO    2023086520 A2    5/2023

OTHER PUBLICATIONS

Almhjell PJ, Johnston KE, Porter NJ, et al "The β-subunit of Tryptophan Synthase is a Latent Tyrosine Synthase" Nature Chemical Biology, May 14, 2024, vol. 20, pp. 1086-1093; doi.org/10.1038/s41589-024-01619-z. (Year: 2024).*

"3-(4-Hydroxy-1-naphthyl) Alanine", PubChem SID 275346487, Available Online at: https://pubchem.ncbi.nlm.nih.gov/substance/275346487, 2015, pp. 1-5.

Almhjell et al., "Engineering Enzymes for Noncanonical Amino Acid Synthesis", Chemical Society Reviews, vol. 47, No. 24, Dec. 21, 2018, pp. 8980-8997.

Boville et al., "Engineered Biosynthesis of β-Alkyl Tryptophan Analogs", ChemRxiv, Available Online at: <https://authors.library.caltech.edu/88128/1/Boville_2018_ChemRxiv.pdf>, Aug. 14, 2018, pp. 14764-14768.

Boville et al., "Improved Synthesis of 4-Cyanotryptophan and Other Tryptophan Analogues in Aqueous Solvent Using Variants of TrpB From Thermotoga Maritima", The Journal of Organic Chemistry, vol. 83, No. 14, Juy 20, 2018, pp. 7447-7452.

Brzovic et al., "Substitution of Glutamic Acid 109 by Aspartic Acid Alters the Substrate Specificity and Catalytic Activity of the Beta-Subunit in the Tryptophan Synthase Bienzyme Complex from *Salmonella typhimurium*", Biochemistry, vol. 31, No. 4, Feb. 4, 1992, pp. 1180-1190.

Buller et al., "Directed Evolution of the Tryptophan Synthase β-Subunit for Stand-Alone Function Recapitulates Allosteric Activation", Proceedings of the National Academy of Sciences, vol. 112, No. 47, Nov. 24, 2015, pp. 14599-14604.

Dick et al., "Tailoring Tryptophan Synthase TrpB for Selective Quaternary Carbon Bond Formation", Journal of the American Chemical Society, vol. 141, Nov. 20, 2019, pp. 19817-19822.

Herger et al., "Synthesis of β-Branched Tryptophan Analogues Using an Engineered Subunit of Tryptophan Synthase", Journal of the American Chemical Society, vol. 138, No. 27, Jul. 2016, pp. 8388-8391.

Kumar et al., "Review on Recent Developments in Biocatalysts for Friedel-Crafts Reactions", ACS Catalysis, vol. 12, Aug. 17, 2022, pp. 10742-10763.

Liu et al., "Significant Expansion of the Fluorescent Protein Chromophore through the Genetic Incorporation of a Metal-Chelating Unnatural Amino Acid", Angewandte Chemie International Edition, vol. 52, No. 18, Apr. 26, 2013, pp. 4805-4809.

Lutke-Eversloh et al., "Perspectives of Biotechnological and its Applications", Applied Microbiology and Biotechnology, vol. 77, Oct. 30, 2007, pp. 751-762.

Milic et al., "Crystallographic Snapshots of Tyrosine Phenol-lyase Show that Substrate Strain Plays a Role in C—C Bond Cleavage", Journal of the American Chemical Society, vol. 133, Sep. 7, 2011, pp. 16468-16476.

Min et al., "Overview on the Biotechnological Production of L-DOPA", Applied Microbiology and Biotechnology, vol. 99, No. 2, Jan. 2015, pp. 575-584.

Murciano-Calles et al., "A Panel of TrpB Biocatalysts Derived from Tryptophan Synthase through the Transfer of Mutations that Mimic Allosteric Activation", Angewandte Chemie International Edition in English, vol. 55, No. 38, Sep. 12, 2016, pp. 11577-11581.

Nagasawa et al., "Syntheses of L-Tyrosine-Related Amino Acids by Tyrosine Phenol-lyase of Citrobacter Intermedius", European Journal of Biochemistry, vol. 117, No. 1, Jun. 1981, pp. 33-40.

Olson et al., "Development of a Single Culture *E.Coli* Expression System for the Enzymatic Synthesis of Fluorinated Tyrosine and its Incorporation into Proteins", Journal of Fluorine Chemistry, vols. 261-262, Sep. 2022, pp. 1-8.

(Continued)

*Primary Examiner* — Aaron J Kosar
*Assistant Examiner* — Andrew T Moehlman
(74) *Attorney, Agent, or Firm* — Kilpatrick Townsend & Stockton LLP

(57) ABSTRACT

Provided herein is an engineered tryptophan synthase β-subunit (TrpB) that catalyzes the synthesis of tyrosine, tyrosine analogs, or salts thereof. Also provided herein are methods for preparing tyrosine, tyrosine analogs, or a salt thereof using the engineered TrpB described herein.

27 Claims, 15 Drawing Sheets

Specification includes a Sequence Listing.

(56) References Cited

OTHER PUBLICATIONS

PCT/US2022/049617, "International Search Report and Written Opinion", Jun. 23, 2023, 12 pages.
PCT/US2022/049617, "Invitation to Pay Additional Fees and, Where Applicable, Protest Fee", Apr. 21, 2023, 2 pages.
Phillips et al., "Aminoacrylate Intermediates in the Reaction of Citrobacter freundii Tyrosine Phenol-Lyase", Biochemistry, vol. 45, No., 31, Jul. 15, 2006, pp. 9575-9583.
Romney et al., "Nitroalkanes as Versatile Nucleophiles for Enzymatic Synthesis of Noncanonical Amino Acids", ACS Catalysis, vol. 9, Aug. 20, 2019, pp. 8726-8730.
Romney et al., "Unlocking Reactivity of TrpB: A General Biocatalytic Platform for Synthesis of Tryptophan Analogues", Journal of the American Chemical Society, vol. 139, No. 31, Aug. 9, 2017, pp. 10769-10776.
Ruvinov et al., "Monovalent Cations Partially Repair a Conformational Defect in a Mutant Tryptophan Synthase α2β2 Complex (β-E109A)", The Journal of Biological Chemistry, vol. 270, No. 29, Jul. 21, 1995, pp. 17333-17338.
Watkins et al., "Direct Enzymatic Synthesis of a Deep-Blue Fluorescent Noncanonical Amino Acid from Azulene and Serine", ChemBioChem, vol. 20, Nos. 1-2, Jan. 15, 2020, pp. 80-83.
Watkins-Dulaney et al., "Asymmetric Alkylation of Ketones Catalyzed by Engineered TrpB", Available online at: https://europepmc.org/backend/ptpmcrender.fcgi?accid=PMC8440449&blobtype=pdf, Sep. 20, 2021, pp. 1-13.
Watkins-Dulaney et al., "Tryptophan Synthase: Biocatalyst Extraordinaire", ChemBioChem, vol. 22, No. 1, Jan. 5, 2021, pp. 5-16.
Won et al., "In Vivo Biosynthesis of Tyrosine Analogs and their Concurrent Incorporation into a Residue-Specific Manner for Enzyme Engineering", Chemical Communications, vol. 55, No. 100, Dec. 28, 2019, pp. 15133--15136.
Zhou et al., "Probing the Function of the Tyr-Cys Cross-Link in Metalloenzymes by the Genetic Incorporation of 3-Methylthiotyrosine", Angewandte Chemie International Edition, vol. 52, No. 4, Jan. 21, 2013, pp. 1203-1207.

* cited by examiner

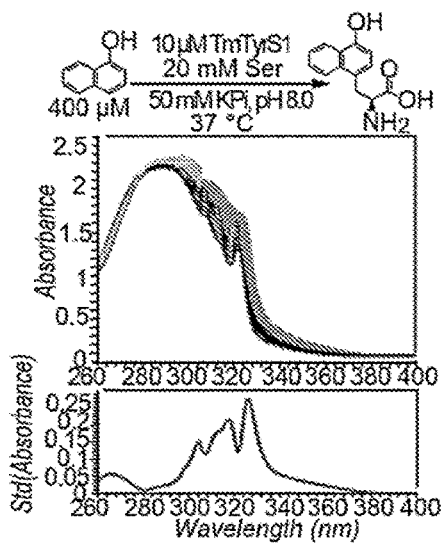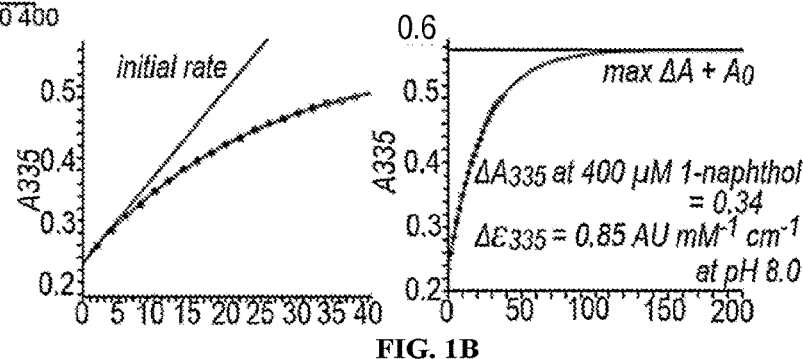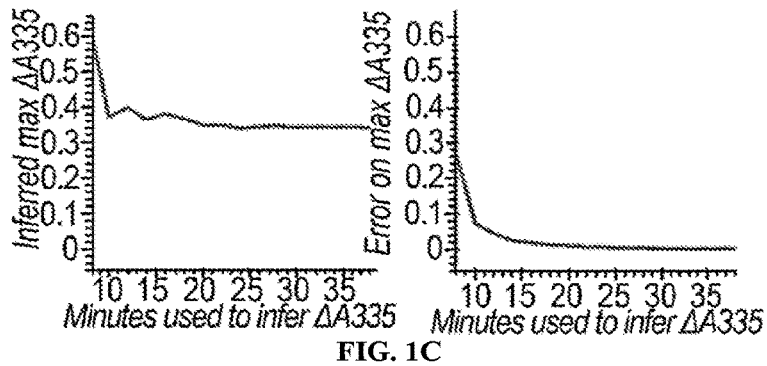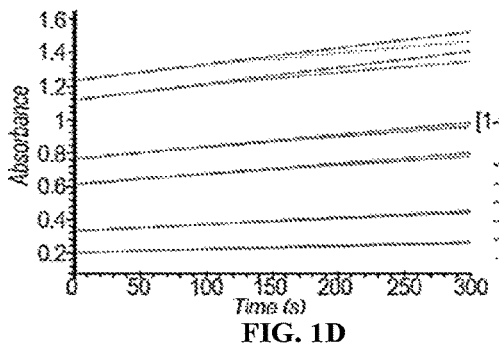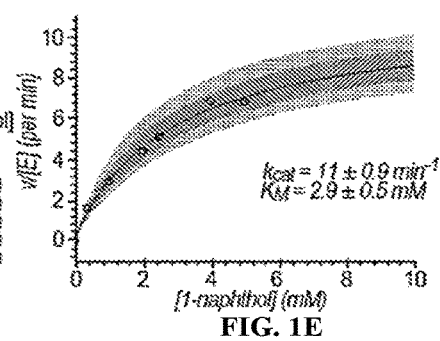
FIG. 1A
FIG. 1B
FIG. 1C
FIG. 1D
FIG. 1E

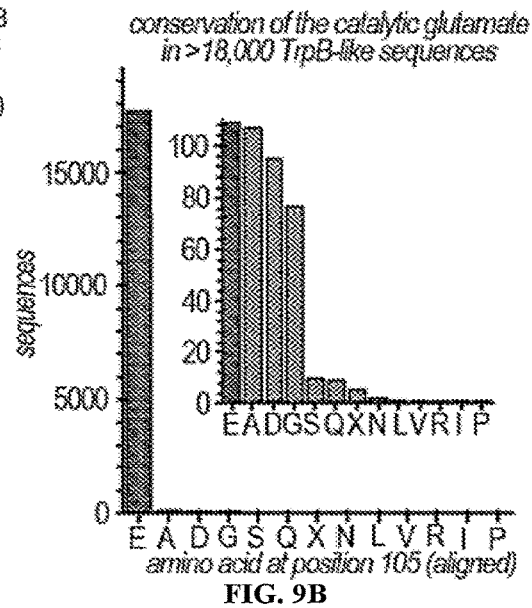
FIG. 9A
FIG. 9B
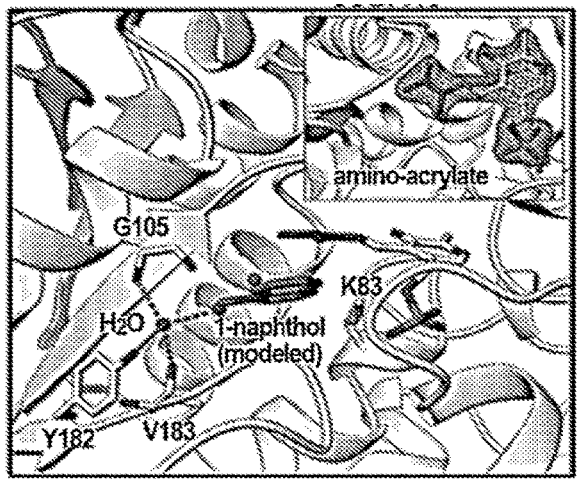
FIG. 9C
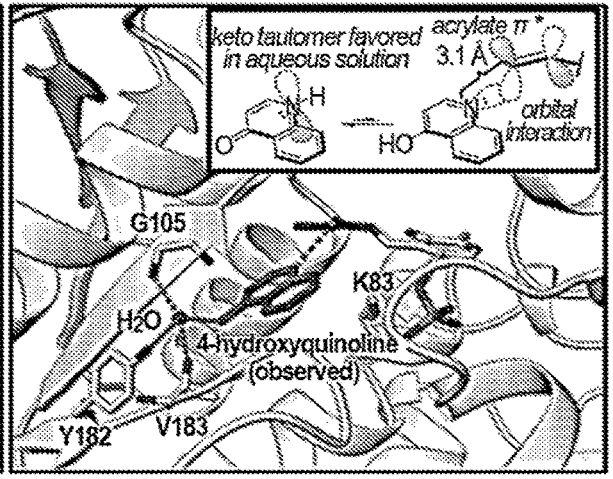
FIG. 9D

ENGINEERED ENZYMES AND METHOD FOR THE SYNTHESIS OF DIVERSE TYROSINE ANALOGS

CROSS-REFERENCE TO RELATED APPLICATIONS

This application claims priority to U.S. Provisional Application No. 63/277,804, filed Nov. 10, 2021, the disclosure of which is incorporated herein by reference in its entirety.

STATEMENT AS TO RIGHTS TO INVENTIONS MADE UNDER FEDERALLY SPONSORED RESEARCH AND DEVELOPMENT

This invention was made with government support under Grant No. GM125887 awarded by the National Institutes of Health. The government has certain rights in the invention.

REFERENCE TO A SEQUENCE LISTING

A Sequence Listing conforming to the rules of WIPO Standard ST.26 is hereby incorporated by reference. Said Sequence Listing has been filed as an electronic document via Patent Center encoded as XML in UTF-8 text. The electronic document, created on Jun. 10, 2024, is entitled "086544-1329842-024010US_ST26" and is 29,831 bytes in size.

BACKGROUND

The aromatic amino acids (aroAAs) L-phenylalanine (Phe), L-tyrosine (Tyr), and L-tryptophan (Trp) are required for all life as fundamental building blocks of proteins. These aroAAs also appear in secondary metabolites and pharmaceuticals, where they are often derivatized to make noncanonical amino acids (ncAAs) that take on a variety of important functional roles. See, Parmeggiani et al., Synthetic and therapeutic applications of ammonia-lyases and aminomutases. Chem. Rev. 118, 73-118 (2018); Almhjell et al., Engineering enzymes for noncanonical amino acid synthesis. Chem. Soc. Rev. 47, 8980-8997 (2018); Lütke-Eversloh et al., Perspectives of biotechnological production of L-tyrosine and its applications. Appl. Microbiol. Biotechnol. 77, 751-762 (2007). These ncAAs resemble the building blocks of natural proteins but are not themselves used in canonical protein synthesis. Derivatives of Tyr, for example, include the Parkinson's medication L-DOPA, the neurotransmitter dopamine, the structural elements of lignin, precursors to more complex natural products, and common biological probes, among many others. See, Cheng et al., Fluorescent amino acids as versatile building blocks for chemical biology. Nat. Rev. Chem. 4, 275-290 (2020); Kim et al., Tyrosine analogues as alternative substrates for protein tyrosine kinase Csk: Insights into substrate selectivity and catalytic mechanism. Bioorg. Med. Chem. 8, 1263-1268 (2000); Rubini et al., Selecting better biocatalysts by complementing recoded bacteria. bioRxiv (2022); Seyedsayamdost et al., Mono-, di-, tri-, and tetra-substituted fluorotyrosines: New probes for enzymes that use tyrosyl radicals in catalysis. J. Am. Chem. Soc. 128, 1569-1579 (2006); Knör et al., Efficient enantioselective synthesis of condensed and aromatic-ring-substituted tyrosine derivatives. J. Org. Chem. 71, 5625-5630 (2006).

The abundance of such ncAAs in natural and unnatural compounds belies the difficulty of their synthesis. See, Ager, Synthesis of unnatural/nonproteinogenic α-amino acids in Amino Acids, Peptides, and Proteins in Organic Chemistry, Vol. 1-Origins and Synthesis of Amino Acids, A. B. Hughes, Ed. (WILEY-VCH, 2009), pp. 495-526. In all known organisms, de novo biosynthesis of the aroAAs occurs through a universally conserved set of chemistries that convert the common precursor chorismate into Phe, Tyr, or Trp, and their derivatization to ncAAs occurs by the action of a diverse array of enzymes. See, Caspi et al., The MetaCyc database of metabolic pathways and enzymes and the BioCyc collection of Pathway/Genome Databases. Nucleic Acids Res. 42 D459-D471 (2014); Lynch et al., Aromatic amino acids: A complex network ripe for future exploration. Trends Plant Sci. 25, 670-681 (2020). These pathways are often inefficient when used for other biosynthetic and biocatalytic purposes, as they have evolved to function well under specific biological conditions. See, Rodriguez et al., Engineering Escherichia coli to overproduce aromatic amino acids and derived compounds. Microb. Cell Fact. 13 (2014). For example, aroAA biosynthesis is tightly regulated and uses complex substrates, which makes it generally unsuitable for the over-production of ncAAs. Furthermore, although the enzymes that biosynthesize ncAAs from aroAA precursors can do so with high efficiencies and selectivities, they lack generality and can be difficult to express in heterologous organisms. Chemical synthesis can provide a more general and modular framework for ncAA preparation, where using serine-derived electrophiles or Negishi cross-couplings is particularly effective. See, Arnold et al., Conversion of serine to stereochemically pure β-substituted α-amino acids via β-lactones. J. Am. Chem. Soc. 107, 7105-7109 (1985); Tanner, Chiral aziridines-Their synthesis and use in stereoselective transformations. Angew. Chem. Int. Ed. 33, 599-619 (1994); Brittain et al., Negishi cross-couplings in the synthesis of amino acids. Org Biomol. Chem. 16, 10-20 (2017). However, these strategies require strictly anaerobic and anhydrous conditions as well as multiple protection and deprotection steps. Furthermore, organic synthesis is not suitable when in vivo ncAA production is beneficial or required, as in many synthetic biology applications. See, Olson et al., Development of a single culture E. coli expression system for the enzymatic synthesis of fluorinated tyrosine and its incorporation into proteins. J. Fluor. Chem. 261-262, 110014 (2022); Won et al., In vivo biosynthesis of tyrosine analogs and their concurrent incorporation into a residue-specific manner for enzyme engineering. Chem. Commun. 55, 15133-15136 (2019); Liu et al., Toward an orthogonal central dogma. Nat. Chem. Biol. 14, 103-106 (2018). Thus, a preparation method that marries the benefits of enzymatic and traditional catalysis applications would be useful across chemical synthesis and synthetic biology.

Biocatalytic Friedel-Crafts alkylation has shown potential for ncAA synthesis, particularly via pyridoxal 5'-phosphate (PLP)-derived electrophilic amino-acrylate intermediates. One such PLP-dependent enzyme, tyrosine phenol lyase (TPL), can accept phenols as nucleophiles to construct Tyr analogs. See, Kumar et al., Review on recent developments in biocatalysts for Friedel-Crafts reactions. ACS Catal. 12, 10742-10763 (2022); Nagasawa et al., Syntheses of L-tyrosine-related amino acids by tyrosine phenol-lyase of Citrobacter intermedius. Eur. J. Biochem. 117, 33-40 (1981). Although this is one of the preferred methods to access valuable Tyr analogs, TPL is constrained by its native function, the degradation of Tyr to phenol, pyruvate, and ammonia through a transient amino-acrylate intermediate. See, Phillips et al., Aminoacrylate intermediates in the reaction of Citrobacter freundii tyrosine phenol-lyase. Biochemistry. 45, 9575 9583 (2006). This activity reduces TPL efficiency in vitro and presents strong equilibrium limitations in vivo. A homolog of TPL, tryptophanase, exists for reversible Trp degradation. The use of tryptophanase for Trp synthesis from indole, however, has been extremely limited, because the β-subunit of tryptophan synthase (TrpB) has proven far more useful.

TrpB catalyzes the final step of all known de novo Trp biosynthesis. See, Watkins-Dulaney et al., Tryptophan synthase: Biocatalyst extraordinaire. *ChemBioChem.* 22, 5-16 (2021). Unlike TPL, TrpB generates a stable amino-acrylate intermediate via β-elimination of L-serine (Ser), which helps it perform the reaction irreversibly. TrpB is used widely for synthesis of Trp analogs and more diverse ncAAs, as well as for synthetic biology applications. See, Buller et al., Directed evolution of the tryptophan synthase β-subunit for stand-alone function recapitulates allosteric activation. *Proc. Natl. Acad. Sci. U.S.A.* 112, 14599-14604 (2015); Herger et al., Synthesis of β-branched tryptophan analogues using an engineered subunit of tryptophan synthase. *J. Am. Chem. Soc.* 138, 8388-8391 (2016); Romney et al., Unlocking reactivity of TrpB: A general biocatalytic platform for synthesis of tryptophan analogues. *J. Am. Chem. Soc.* 139, 10769-10776 (2017); Romney et al., Nitroalkanes as versatile nucleophiles for enzymatic synthesis of noncanonical amino acids. *ACS Catal.* 9, 8726-8730 (2019); Dick et al., Tailoring tryptophan synthase TrpB for selective quaternary carbon bond formation. *J. Am. Chem. Soc.* 141, 19817-19822 (2019); Watkins et al., Direct enzymatic synthesis of a deep-blue fluorescent noncanonical amino acid from azulene and serine. *ChemBioChem.* 21, 80-83 (2019); Goss et al., A convenient enzymatic synthesis of L-halotryptophans. *Chem. Commun.,* 4924-4925 (2006); Smith et al., The first one-pot synthesis of L-7-iodotryptophan from 7-iodoindole and serine, and an improved synthesis of other L-7-halotryptophans. *Org. Lett.* 16, 2622-2625 (2014); Rix et al., Scalable continuous evolution for the generation of diverse enzyme variants encompassing promiscuous activities. *Nat. Commun.* 11, 5644 (2020). Despite over half a century of intense study, however, no TrpB has been shown to react with phenols to generate Tyr derivatives, nor is there is an equivalent "tyrosine synthase" in native Tyr synthesis. See, Tatum et al., Indole and serine in the biosynthesis and breakdown of tryptophane. *Proc. Natl. Acad. Sci. U.S.A.* 30, 30-37 (1944); Hall et al., The behaviour of the Bz-methylindoles as substrates and inhibitors for *Neurospora crassa* tryptophan synthase. *Biochem. J.* 84, 12-16 (1962); Brzovic et al., Substitution of glutamic acid 109 by aspartic acid alters the substrate specificity and catalytic activity of the β-subunit in the tryptophan synthase bienzyme complex from *Salmonella typhimurium. Biochemistry.* 31, 1180-1190 (1992); Ruvinov et al., Monovalent cations partially repair a conformational defect in a mutant tryptophan synthase α2β2 complex (β-E109A). *J. Biol. Chem.* 270, 17333-17338 (1995). Herein, the problem is addressed through directed evolution of TrpB to form a tyrosine synthase (TyrS), capable of noncanonical Tyr synthesis via the irreversible, regioselective Friedel-Crafts alkylation of phenols, both in vitro and in vivo.

BRIEF SUMMARY

The present disclosure provides polypeptide compositions and methods for the synthesis of tyrosine and tyrosine derivatives. In some embodiments, the present disclosure provides an engineered tryptophan synthase β-subunit (TrpB) comprising an amino acid substitution at a position corresponding to amino acid residue E105 of SEQ ID NO: 1. In some embodiments, the engineered TrpB catalyzes the synthesis of a compound, wherein the compound is tyrosine or a tyrosine analog or a salt thereof. In some embodiments, the compound is at least 90% regioselective for para alkylation. In some embodiments, the compound is at least 95% regioselective for para alkylation. In some embodiments, the compound is at least 99% regioselective for para alkylation.

In some embodiments, the tyrosine is L-tyrosine. In some embodiments, the tyrosine analog is selected from the group consisting of 2-amino-3-(4-hydroxy-3-(methylthio)phenyl)propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl)propanoic acid, 2-amino-3-(3-fluoro-4-hydroxyphenyl)propanoic acid, 2-amino-3-(4-hydroxy-3-methoxyphenyl)propanoic acid, 2-amino-3-(3-bromo-4-hydroxyphenyl)propanoic acid, 2-amino-3-(3,5-dichloro-4-hydroxyphenyl)propanoic acid, 2-amino-3-(4-hydroxy-3,5-dimethylphenyl)propanoic acid, 2-amino-3-(2-fluoro-4-hydroxyphenyl)propanoic acid, 2-amino-3-(2-chloro-4-hydroxyphenyl)propanoic acid, 2-amino-3-(4-hydroxy-2-methylphenyl)propanoic acid, 2-amino-3-(2,3,5,6-tetrafluoro-4-hydroxyphenyl)propanoic acid, and 2-amino-3-(4-hydroxynaphthalen-1-yl)butanoic acid.

Also disclosed herein is an engineered tryptophan synthase β-subunit (TrpB) comprising the amino acid sequence of any one of SEQ ID NOS: 4-11.

Disclosed herein are methods for preparing a compound with the engineered TrpB, wherein the compound is tyrosine or a tyrosine analog or a salt thereof, the method comprising combining: (i) a first substrate; (ii) a second substrate; and (iii) the engineered TrpB in a reaction mixture; and maintaining the reaction mixture under conditions sufficient to form the compound. In some embodiments, the tyrosine is L-tyrosine. In some embodiments, the first substrate is a donor amino acid. In some embodiments, the donor amino acid is a β-hydroxy amino acid. In some embodiments, the second substrate is a phenol or phenol analog.

Also disclosed herein are methods of preparing a compound of Formula I:

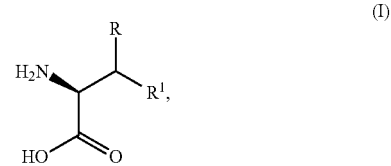

or a salt thereof,
wherein R is (A), (B), or (C):

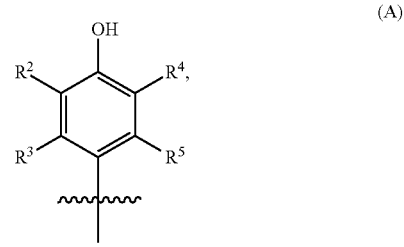

-continued

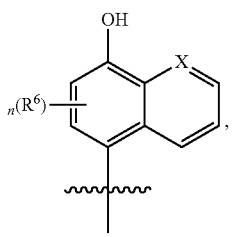
(B)

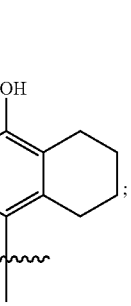
(C)

the method comprising:
combining: (i) a β-hydroxy amino acid; (ii) phenol or a phenol analog; and (iii) the engineered TrpB in a reaction mixture; and maintaining the reaction mixture under conditions sufficient to form the compound according to Formula I;
wherein:
$R^1$ is hydrogen or $C_{1-8}$ alkyl, which is optionally substituted with one or more $R^{1a}$;
each $R^{1a}$ is independently selected from the group consisting of hydrogen, halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{1b}$)$_2$, —C(O)$R^{1c}$, —C(O)N($R^{1b}$)$_2$, —N$R^{1b}$C(O)$R^{1c}$, and —OC(O)$R^{1c}$;
each $R^{1b}$ is independently selected from the group consisting of hydrogen and $C_{1-6}$ alkyl;
each $R^{1c}$ is independently selected from the group consisting of hydrogen, —OH, halogen, $C_{1-6}$ alkyl, $C_{1-6}$ alkoxy;
$R^2$, $R^3$, $R^4$, and $R^5$ are independently selected from the group consisting of hydrogen, halogen, $C_{1-8}$ alkyl, which is optionally substituted with one or more $R^{2a}$;
each $R^{2a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{2b}$)$_2$, —C(O)$R^{2c}$, —C(O)N($R^{2b}$)$_2$, —N$R^{2b}$C(O)$R^{2c}$, and —OC(O)$R^{2c}$;
each $R^{2b}$ is independently selected from the group consisting of hydrogen and $C_{1-6}$ alkyl;
each $R^{2c}$ is independently selected from the group consisting of hydrogen, —OH, halogen, $C_{1-6}$ alkyl, $C_{1-6}$ alkoxy;
$R^6$ is hydrogen or $C_{1-8}$ alkyl, which is optionally substituted with one or more $R^{3a}$;
each $R^{3a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{3b}$)$_2$, —C(O)$R^{3c}$, —C(O)N($R^{3b}$)$_2$, —N$R^{3b}$C(O)$R^{3c}$, and —OC(O)$R^{3c}$;
each $R^{3b}$ is independently selected from the group consisting of hydrogen and $C_{1-6}$ alkyl;
each $R^{3c}$ is independently selected from the group consisting of hydrogen, —OH, halogen, $C_{1-6}$ alkyl, $C_{1-6}$ alkoxy;
n is selected from 0, 1, 2, 3, 4, or 5;
m is selected from 0, 1, 2, 3, 4, 5, or 6;
X is —C($R^7$) or —N;
wherein $R^7$ is hydrogen or $C_{1-8}$ alkyl, which is optionally substituted with one or more $R^{4a}$;
each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{4b}$)$_2$, —C(O)$R^{4c}$, —C(O)N($R^{4b}$)$_2$, —N$R^{4b}$C(O)$R^{4c}$, and —OC(O)$R^{4c}$;
each $R^{4b}$ is independently selected from the group consisting of hydrogen and $C_{1-6}$ alkyl; and
each $R^4$ is independently selected from the group consisting of hydrogen, —OH, halogen, $C_{1-6}$ alkyl, $C_{1-6}$ alkoxy.

Further disclosed herein are methods of preparing a compound of Formula II:

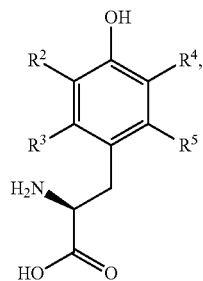
(II)

or a salt thereof,
the method comprising:
combining: (i) a β-hydroxy amino acid; (ii) phenol or a phenol analog; and (iii) the engineered TrpB in a reaction mixture; and maintaining the reaction mixture under conditions sufficient to form the compound according to Formula II;
wherein:
$R^2$, $R^3$, $R^4$, and $R^5$ are independently selected from the group consisting of hydrogen, halogen, $C_{1-8}$ alkyl, which is optionally substituted with one or more $R^{2a}$;
each $R^{2a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{2b}$)$_2$, —C(O)$R^{2c}$, —C(O)N($R^{2b}$)$_2$, —N$R^{2b}$C(O)$R^{2c}$, and —OC(O)$R^{2c}$;
each $R^{2b}$ is independently selected from the group consisting of hydrogen and $C_{1-6}$ alkyl; and
each $R^{2c}$ is independently selected from the group consisting of hydrogen, —OH, halogen, $C_{1-6}$ alkyl, $C_{1-6}$ alkoxy.

Further disclosed herein are methods of preparing a compound of Formula III:

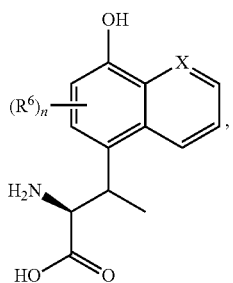

(III)

or a salt thereof, the method comprising:

combining: (i) a β-hydroxy amino acid; (ii) phenol or a phenol analog; and (iii) the engineered TrpB in a reaction mixture; and maintaining the reaction mixture under conditions sufficient to form the compound according to Formula III;

wherein:

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{3b}$)$_2$, —C(O)$R^{3c}$, —C(O)N($R^{3b}$)$_2$, —N$R^{3b}$C(O)$R^{3c}$, and —OC(O)$R^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C($R^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{4b}$)$_2$, —C(O)$R^{4c}$, —C(O)N($R^{4b}$)$_2$, —N$R^{4b}$C(O)$R^{4c}$, and —OC(O)$R^{4c}$;

each $R^{4b}$ is independently selected from the group consisting of hydrogen and $C_{1-6}$ alkyl; and each $R^4$ is independently selected from the group consisting of hydrogen, —OH, halogen, $C_{1-6}$ alkyl, $C_{1-6}$ alkoxy.

The present disclosure also provides a compound of Formula I:

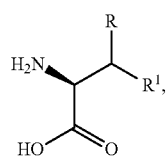

(I)

or a salt thereof, wherein:

R is (B) or (C):

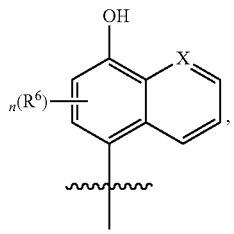

(B)

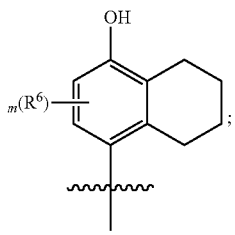

(C)

$R^1$ is hydrogen or $C_{1-8}$ alkyl, which is optionally substituted with one or more $R^{1a}$;

each $R^{1a}$ is independently selected from the group consisting of hydrogen, halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{1b}$)$_2$, —C(O)$R^{1c}$, —C(O)N($R^{1b}$)$_2$, —N$R^{1b}$C(O)$R^{1c}$, and —OC(O)$R^{1c}$;

each $R^{1b}$ is independently selected from the group consisting of hydrogen and $C_{1-6}$ alkyl;

each $R^{1c}$ is independently selected from the group consisting of hydrogen, —OH, halogen, $C_{1-6}$ alkyl, $C_{1-6}$ alkoxy;

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{3b}$)$_2$, —C(O)$R^{3c}$, —C(O)N($R^{3b}$)$_2$, —N$R^{3b}$C(O)$R^{3c}$, and —OC(O)$R^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C($R^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{4b}$)$_2$, —C(O)$R^{4c}$, —C(O)N($R^{4b}$)$_2$, —N$R^{4b}$C(O)$R^{4c}$, and —OC(O)$R^4$;

each $R^{4b}$ is independently selected from the group consisting of hydrogen and $C_{1-6}$ alkyl; and each $R^4$ is independently selected from the group consisting of hydrogen, —OH, halogen, $C_{1-6}$ alkyl, $C_{1-6}$ alkoxy.

The present disclosure further provides a compound of Formula III:

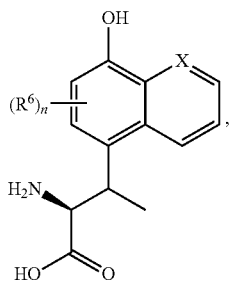

(III)

or a salt thereof, wherein:
R$^6$ is hydrogen or C$_{1-8}$ alkyl, which is optionally substituted with one or more R$^{3a}$;
each R$^{3a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;
each R$^{3b}$ is independently selected from the group consisting of hydrogen and C$_{1-6}$ alkyl;
each R$^{3c}$ is independently selected from the group consisting of hydrogen, —OH, halogen, C$_{1-6}$ alkyl, C$_{1-6}$ alkoxy;
n is selected from 0, 1, 2, 3, 4, or 5;
m is selected from 0, 1, 2, 3, 4, 5, or 6;
X is —C(R$^7$) or —N;
wherein R$^7$ is hydrogen or C$_{1-8}$ alkyl, which is optionally substituted with one or more R$^{4a}$;
each R$^{4a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^{4c}$;
each R$^{4b}$ is independently selected from the group consisting of hydrogen and C$_{1-6}$ alkyl; and
each R$^4$ is independently selected from the group consisting of hydrogen, —OH, halogen, C$_{1-6}$ alkyl, C$_{1-6}$ alkoxy.

In some embodiments, the compound has a structure selected from the group consisting of

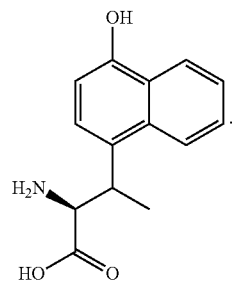

BRIEF DESCRIPTION OF THE DRAWINGS

FIG. 1 shows the steps of development of a continuous colorimetric assay for NaphAla production. FIG. 1A shows a schematic of the conversion of 1-naphthol to NaphAla. The absorbance graph shows a change in the absorbance spectrum of 1-naphthol from dark to light, with an increase in absorbance at wavelengths>290 nm and an isosbestic point between 280-284 nm (284 nm is used for this study), as shown by the standard deviation for each wavelength in the absorbance graph (lower standard deviation=less absorbance change). FIG. 1B shows a set of graphs depicting the reaction progress curve for 400 µM 1-naphthol at 335 nm, fit to an exponential function. The fit and estimated initial rate are plotted as lines. The horizontal line represents the predicted maximum change in absorbance (max ΔA) over the starting absorbance (A$_0$). As this represents the full colorimetric change at 335 nm for the conversion of 400 µM 1-naphthol, the molar change in absorptivity (Δε$_{335}$) for the conversion of 1-naphthol to NaphAla can be inferred to be 0.85 AU mM$_{-1}$ cm$^{-1}$ at pH 8.0 to convert absorbance units to real concentrations. FIG. 1C shows a set of graphs depicting estimates and errors of max ΔA with increasing data used. FIG. 1D shows a graph depicting the full absorbance time courses at 335 nm at varying 1-naphthol concentrations, with initial rates as gray lines. FIG. 1E shows a graph representing a Michaelis-Menten model of initial rates obtained from time course data (blue points). 70% and 95% confidence intervals are shown, colored from dark to light, respectively.

FIG. 3 shows pictures outlining the process of multi-gram-scale NaphAla preparation and characterization.

FIG. 4 is data representing the biocatalytic utility of TyrS variants for Tyr analog synthesis.

FIG. 5 is a picture of gram-scale 3-methyl-Tyr preparation.

FIG. 8 are schematics and data representing the directed evolution of a tyrosine synthase.

FIG. 9 shows how removal of the conserved catalytic glutamate in TrpB unlocks regioselective tyrosine synthase activity. FIG. 9A is a graph showing the rates of conversion of different substrates in two TrpB variants with the catalytic glutamate sidechain (residue=E) or without it (residue=G). Tm9D8*(SEQ ID NO: 3) was tested at 37° C.; Pf2B9 (SEQ ID NO: 12) was tested at 75° C. $^a$Rate of indole conversion was calculated using both Trp and isoTrp formation. $^b$Performed with 50 mM substrate. FIG. 9B is a graph of the conservation of the catalytic glutamate in 18,051 TrpB-like sequences. Inset: An axis-adjusted view for the sequences with a different residue. X=unidentified. FIG. 9C is a cartoon of the crystal structure of amino-acrylate bound TmTyrS1 (SEQ ID NO: 6) with 1-naphthol naïvely modeled in a productive binding pose. Inset: amino-acrylate polder omit map contoured at 5σ. FIG. 9D is a cartoon of the crystal structure of amino-acrylate-bound TmTyrS1 (SEQ ID NO: 6) in complex with the non-reactive 1-naphthol analog 4-hydroxylquinoline coordinated to an active-site water in place of E105. Inset: The keto tautomer is favored in aqueous solution while the enol tautomer is observed in the enzyme interacting with the electrophilic amino-acrylate CB.

FIG. 10 is a set of graphs showing the conservation of E105 and G229 in aligned TrpB-like sequences.

FIG. 11 are cartoons of crystal structures of TmTyrS1 (SEQ ID NO: 6).

DETAILED DESCRIPTION

Figure 2:
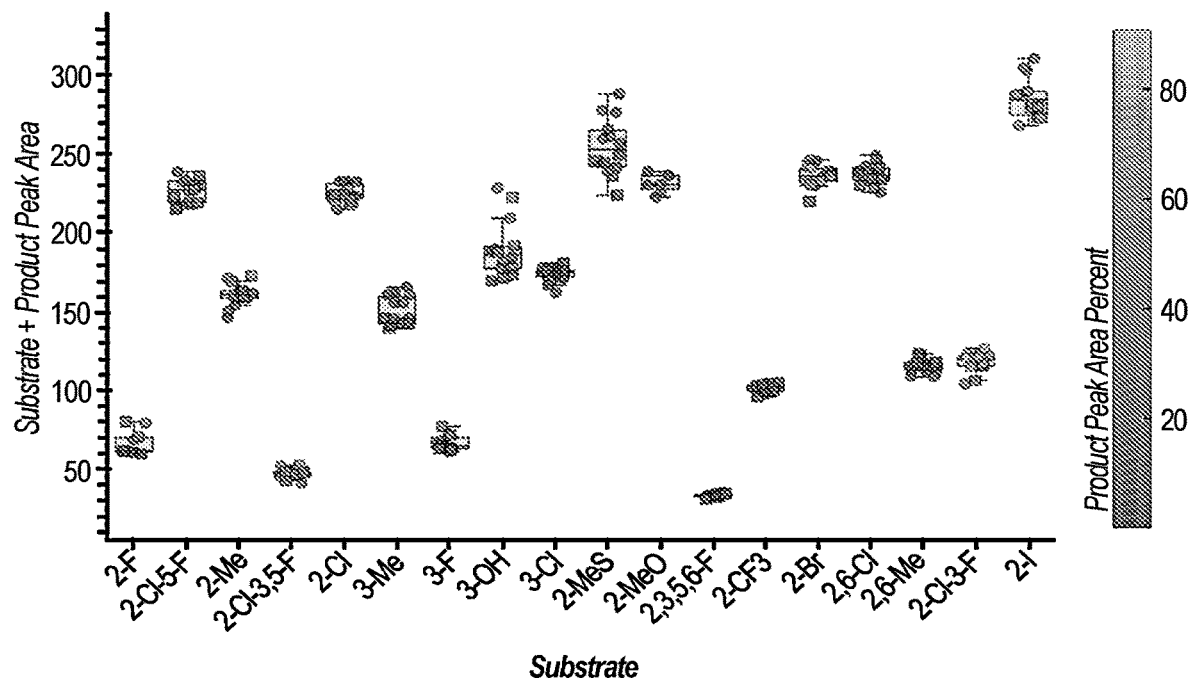
FIG. 2 shows a graph comparing total HPLC areas from unique reactions with different substrates. The squares indicate the first replicate of each reaction. The circles are the second replicate. The substrate and product peak areas are summed for each reaction for each substrate and differentiated by product peak area percent, as used to prepare FIG. 4A.

Provided herein are compositions and methods for the synthesis of tyrosine and tyrosine analogs using engineered variants of β-subunit of tryptophan synthases (TrpBs). The engineered TrpB enzymes are named tyrosine synthases (TyrS). TyrS is capable of Tyr synthesis via the irreversible, regioselective Friedel-Crafts alkylation of phenols, both in vitro and in vivo. TrpB was selected as the basis for engineering new enzymes to make tyrosine analogs because certain variants of TrpB can accept phenol and phenol analogs as nucleophiles to form L-tyrosine (Tyr) and Tyr analogs from L-serine (Ser), in most cases with perfect enantio- and regio-selectivity.

Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications, patents, published patent applications, GenBank accession numbers and UniProt reference numbers mentioned herein are incorporated herein by reference to disclose and describe the methods and/or materials in connection with which the publications are cited.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the reagent" includes reference to one or more reagents known to those skilled in the art, and so forth.

The term "about" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximately unless stated otherwise, meaning that the term "about" or "approximately" can be inferred when not expressly stated.

The terms "tryptophan synthase β-subunit" and "TrpB" refer to a polypeptide (EC 4.2.1.20) that catalyzes the formation of tryptophan from serine (unsubstituted or substituted) and indole (unsubstituted or substituted). Tryptophan synthases are absent in animals, but they are expressed in a variety of species of plants, eubacteria, archaebacteria, protista, and fungi. The β-subunit catalyzes the condensation of indole and serine to form tryptophan in a PLP-dependent reaction.

The term "indole," by itself or as part of another functional group, refers to 2,3-benzopyrrole and analogs thereof.

The term "serine," by itself or as part of another functional group, refers to 2-amino-3-hydroxypropanoic acid. Serines include L-serine ((2S)-2-amino-3-hydroxypropanoic acid) and derivatives thereof, as well as D-serine ((2R)-2-amino-3-hydroxypropanoic acid) and derivatives thereof. In some embodiments, the serine is L-serine or a derivative thereof. The term "β-substituted serine" refers to a 2-amino-3-hydroxypropanoic acid having an alkyl substituent covalently bonded to the 3-carbon (i.e., in the position with respect to the carboxylate functional group). The alkyl substituent can be further substituted as described below.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can refer to alkyl groups having up to 20 carbons atoms, such as, but not limited to heptyl, octyl, nonyl, decyl, etc. Alkyl groups can be unsubstituted or substituted. Unless otherwise specified, "substituted alkyl" groups can be substituted with one or more moieties selected from halo, hydroxy, amino, alkylamino, alkoxy, haloalkyl, carboxy, amido, nitro, oxo, and cyano.

As used herein, the term "alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be unsubstituted or substituted. Unless otherwise specified, "substituted alkenyl" groups can be substituted with one or more moieties selected from halo, hydroxy, amino, alkylamino, alkoxy, haloalkyl, carboxy, amido, nitro, oxo, and cyano.

As used herein, the term "alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be unsubstituted or substituted. Unless otherwise specified, "substituted alkynyl" groups can be substituted with one or more moieties selected from halo, hydroxy, amino, alkylamino, alkoxy, haloalkyl, carboxy, amido, nitro, oxo, and cyano.

As used herein, the term "aryl" refers to an aromatic carbon ring system having any suitable number of ring atoms and any suitable number of rings. Aryl groups can include any suitable number of carbon ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be unsubstituted or substituted. Unless otherwise specified, "substituted aryl" groups can be substituted with one or more moieties selected from halo, hydroxy, amino, alkylamino, alkoxy, haloalkyl, carboxy, amido, nitro, oxo, and cyano.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, and $C_{6-8}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2]bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. Cycloalkyl groups can be unsubstituted or substituted. Unless otherwise specified, "substituted cycloalkyl" groups can be substituted with one or more moieties selected from halo, hydroxy, amino, alkylamino, alkoxy, haloalkyl, carboxy, amido, nitro, oxo, and cyano.

As used herein, the term "heterocyclyl" refers to a saturated ring system having from 3 to 12 ring members and from 1 to 4 heteroatoms selected from N, O and S. Additional heteroatoms including, but not limited to, B, Al, Si and P can also be present in a heterocycloalkyl group. The heteroatoms can be oxidized to form moieties such as, but not limited to, —S(O)— and —S(O)$_2$—. Heterocyclyl groups can include any number of ring atoms, such as, 3 to 6, 4 to 6, 5 to 6, 4 to 6, or 4 to 7 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. Examples of heterocyclyl groups include, but are not limited to, aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. Heterocyclyl groups can be unsubstituted or substituted. Unless otherwise specified, "substituted heterocyclyl" groups can be substituted with one or more moieties selected from halo, hydroxy, amino, alkylamino, alkoxy, haloalkyl, carboxy, amido, nitro, oxo, and cyano.

As used herein, the term "alkoxy" refers to an alkyl group having an oxygen atom that connects the alkyl group to the point of attachment: i.e., alkyl-O—. As for alkyl group, alkoxy groups can have any suitable number of carbon atoms, such as $C_{1-6}$ or $C_{1-4}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. Alkoxy groups can be unsubstituted or substituted. Unless otherwise specified, "substituted alkoxy" groups can be substituted with one or more moieties selected from halo, hydroxy, amino, alkylamino, alkoxy, haloalkyl, carboxy, amido, nitro, oxo, and cyano.

As used herein, the terms "halo" and "halogen" refer to fluorine, chlorine, bromine and iodine.

As used herein, the term "haloalkyl" refers to an alkyl moiety as defined above substituted with at least one halogen atom.

As used herein, the term "acyl" refers to a moiety —C(O)R, wherein R is an alkyl group.

As used herein, the term "oxo" refers to an oxygen atom that is double-bonded to a compound (i.e., O=).

As used herein, the term "carboxy" refers to a moiety —C(O) OH. The carboxy moiety can be ionized to form the carboxylate anion. "Alkyl carboxylate" refers to a moiety —C(O) OR, wherein R is an alkyl group as defined herein.

As used herein, the term "amino" refers to a moiety —NR$^3$, wherein each R group is H or alkyl.

As used herein, the term "amido" refers to a moiety —NRC(O)R or —C(O)NR$^2$, wherein each R group is H or alkyl.

As used herein, the term "protecting group" refers to a chemical moiety that renders a functional group such as an amine or carboxylic acid unreactive, but is also removable so as to restore the reactive functional group. Examples of protecting groups include, but are not limited to, benzyloxycarbonyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis,* 4th Ed 2007, Wiley-Interscience, New York).

The terms "protein," "peptide," and "polypeptide" are used interchangeably herein to refer to a polymer of amino acid residues, or an assembly of multiple polymers of amino acid residues. The terms apply to amino acid polymers in which one or more amino acid residues are an artificial chemical mimic of a corresponding naturally occurring amino acid, as well as to naturally occurring amino acid polymers and non-naturally occurring amino acid polymers.

The term "amino acid" includes genetically-encoded α-amino acids and their stereoisomers, as well as other amino acids as described herein, and their stereoisomers. "Stereoisomers" of amino acids refers to mirror image isomers of the amino acids, such as L-amino acids or D-amino acids. For example, a stereoisomer of an L-amino acid refers to the mirror image isomer, i.e., the D-amino acid.

Amino acids include those encoded by the genetic code, as well as those amino acids that are later modified, e.g., hydroxyproline, γ-carboxyglutamate and O-phosphoserine. Genetically encoded α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), praline (Pro), glutamine (Gln), serine (Ser), threonine (Thr), valine (Val), tryptophan (Trp), tyrosine (Tyr), and combinations thereof. Stereoisomers of genetically-encoded α-amino acids include, without limitation, D-alanine (D-Ala), D-cysteine (D-Cys), D-asparticacid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. Stereoisomers of genetically-encoded α-amino acids include, without limitation, L-alanine (L-Ala), L-cysteine (L-Cys), L-asparticacid (L-Asp), L-glutamic acid (L-Glu), L-phenylalanine (L-Phe), L-histidine (L-His), L-isoleucine (L-Ile), L-arginine (L-Arg), L-lysine (L-Lys), L-leucine (L-Leu), L-methionine (L-Met), L-asparagine (L-Asn), L-proline (L-Pro), L-glutamine (L-Gln), L-serine (L-Ser), L-threonine (L-Thr), L-valine (L-Val), L-tryptophan (L-Trp), L-tyrosine (L-Tyr), and combinations thereof.

Amino acids also include, without limitation, amino acid analogs, amino acid mimetics, synthetic amino acids, N-substituted glycines, and N-methyl amino acids in either the L- or D-configuration that function in a manner similar to the genetically-encoded aminoacids. For example, "amino acid analogs" have the same basic chemical structure as genetically encoded amino acids, i.e., a carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a genetically-encoded amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a genetically-encoded amino acid such as an L-aminoacid, a stereoisomer of a genetically-encoded amino acid such as a D-amino acid, an amino acid analog, an amino acid mimetic, a synthetic amino acid, an N-substituted glycine, and an N-methyl amino acid.

The term "oligonucleotide," "nucleic acid," "nucleotide," or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991), Ohtsuka et al., J Biol. Chem. 260:2605-2608 (1985), and Rossolini et al., Mol. Cell. Probes 8:91-98 (1994)). The term nucleic acid is used interchangeably with gene, cDNA, and mRNA encoded by a gene.

The term "donor amino acid" refers to an amino acid having a good leaving group. A "good leaving group" refers to a conjugate base of a strong acid. In the context of this disclosure, a "donor amino acid" may refer to a β-hydroxy amino acid (with $H_2O$ as the leaving group), a β-chloroalanine (with HCl is the leaving group), or a S-(o-nitrothiophenyl)-L-cysteine (with o-nitrothiophenol as the leaving group). Phillips et al., Synthesis of L-tyrosine from phenol and S-(o-nitrophenyl)-L-cysteine catalyzed by tyrosine phenol-lyase. Enzym. Microb. Technol. 11, 80-83 (1989).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, for example, BLAST and BLAST 2.0 algorithms can be used, which are described in Altschul et al., (1990) *J Mol. Biol.* 215:403-410 and Altschul et al. (1977)*Nucleic Acids Res.* 25:3389-3402, respectively. Software for performing BLAST analyses is publicly available at the National Center for Biotechnology Information website, ncbi.nlm.nih.gov. The BLAST algorithms provide a statistical analysis of the similarity between two sequences (see, e.g., Karlin & Altschul, *Proc. Nat'l. Acad. Sci. USA,* 90:5873-5787 (1993)). One measure of similarity provided by the BLAST algorithm is the smallest sum probability (P(N)), which provides an indication of the probability by which a match between two nucleotide or amino acid sequences would occur by chance.

The term "site-directed mutagenesis" refers to various methods in which specific changes are intentionally made introduced into a nucleotide sequence (i.e., specific nucleotide changes are introduced at pre-determined locations). Known methods of performing site-directed mutagenesis include, but are not limited to, PCR site-directed mutagenesis, cassette mutagenesis, whole plasmid mutagenesis, and Kunkel's method.

The term "site-saturation mutagenesis," also known as "saturation mutagenesis," refers to a method of introducing random mutations at predetermined locations with a nucleotide sequence, and is a method commonly used in the context of directed evolution (e.g., the optimization of proteins (e.g., in order to enhance activity, stability, and/or stability), metabolic pathways, and genomes). In site-saturation mutagenesis, artificial gene sequences are synthesized using one or more primers that contain degenerate codons; these degenerate codons introduce variability into the position(s) being optimized. Each of the three positions within a degenerate codon encodes a base such as adenine (A), cytosine (C), thymine (T), or guanine (G), or encodes a degenerate position such as K (which can be G or T), M (which can be A or C), R (which can be A or G), S (which can be C or G), W (which can be A or T), Y (which can be C or T), B (which can be C, G, or T), D (which can be A, G, or T), H (which can be A, C, or T), V (which can be A, C, or G), or N (which can be A, C, G, or T). Thus, as a non-limiting example, the degenerate codon NDT encodes an A, C, G, or T at the first position, an A, G, or T at the second position, and a T at the third position. This particular combination of 12 codons represents 12 amino acids (Phe, Leu, Ile, Val, Tyr, His, Asn, Asp, Cys, Arg, Ser, and Gly). As another non-limiting example, the degenerate codon VHG encodes an A, C, or G at the first position, an A, C, or T at the second position, and G at the third position. This particular combination of 9 codons represents 8 amino acids (Lys, Thr, Met, Glu, Pro, Leu, Ala, and Val). As another non-limiting example, the "fully randomized" degenerate codon NNN includes, but is not limited to, all 64 codons for the 20 canonical amino acids.

In some instances, a mixture of degenerate primers is used. A mixture of degenerate primers can contain any number of different degenerate primers in any ratio. As anon-limiting example, a mixture of primers containing the NDT, VHG, and TGG primers can be used. Such a mixture can contain, for example, an amount of each primer in a 12:9:1 ratio (e.g., a NDT:VHG:TGG ratio of 12:9:1). Based on various considerations, non-limiting examples being desired redundancy, the desired presence of stop codons, and/or desired amino acid characteristics (e.g., the presence of nonpolar residues, charged residues, or small side chain residues), different combinations of degenerate primers can be used. Considerations and methods for choosing optimal combinations of degenerate primers will be known to one of skill in the art.

The term "nucleotide sequence encoding a peptide" means the segment of DNA involved in producing a peptide chain. The term can include regions preceding and following the coding region (leader and trailer) involved in the transcription/translation of a gene product and the regulation of the transcription/translation, as well as intervening sequences (introns) between individual coding segments (exons).

The term "corresponding to" or "relative to", when used in the context of the identification of a given amino acid residue in a polypeptide sequence, refers to the position of the residue of a specified reference sequence when the given amino acid sequence is maximally aligned and compared to the reference sequence. Thus, for example, an amino acid residue in a polypeptide (e.g., an engineered TrpB) "corresponds to" amino acid residue E105 of SEQ ID NO: 1 when the residue aligns with E105 of SEQ ID NO: 1 when optimally aligned to SEQ ID NO: 1. The polypeptide that is aligned to the reference sequence need not be the same length as the reference sequence (e.g., SEQ ID NO: 1).

The term "natural E105A" or "A105" and "natural E105G" or "G105" means sequences that naturally have alanine (A) at a position corresponding to the 105 position of SEQ ID NO: 1 or glycine (G) at a position corresponding to the 105 position of SEQ ID NO: 1, respectively.

The term "homolog," as used herein with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the function of the protein is similar to the function of the second protein, and/or if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences and/or similar functions. In particular embodiments, the homology between two proteins is indicative of its shared ancestry, related by evolution.

Engineered TrpB ("TyrS") for Synthesis of Tyrosine Analogs

Provided herein is an engineered tryptophan synthase β-subunit (TrpB) comprising an amino acid substitution at a position corresponding to amino acid residue E105 of SEQ ID NO: 1. In some embodiments, the engineered TrpB catalyzes the synthesis of tyrosine or a tyrosine analog. In some embodiments, the engineered TrpB comprises an amino acid sequence at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 1.

In some embodiments, the engineered TrpB is a TrpB that is a natural E105A or A105 enzyme relative to SEQ ID NO: 1. In some embodiments, the engineered TrpB is a TrpB that is a natural E105G or G105 enzyme relative to SEQ ID NO: 1. In some embodiments, the natural E105A enzyme is SEQ ID NO: 14. In some embodiments, the natural E105G enzyme is SEQ ID NO: 15.

In some embodiments, exemplary sequences of natural E105A or A105 TrpB enzymes include Uniprot Reference IDs: A0A7J7C4H8_TRIWF, A0A5C7GRA8_9ROSI, A0A1S2YX36_CICAR, A0A1U8PTG1_GOSHI, A0A7G2RM00_BETVV, A0A5A7R654_STRAF, A0A1Q3CYB6_CEPFO, A0A6A3AT34_HIBSY, A0A2N9ITW1_FAGSY, A0A022QGH7_ERYGU, A0A2J6JVN6_LACSA, A0A3P6GFR5_BRAOL, A0A6D2KSF8_9BRAS, A0A438EE28_VITVI, M4DK02_BRARP, A0A830CMF6_9LAMI, A0A3N7HDA6_POPTR, A0A7J8MVX1_9ROSI, A0A6A1W9A7_9ROSI, A0A5D3BJR8_CUCME, A0A4D8Y7U9_SALSN, A0A6P4AIV3_ZIZJJ, A0A1H9V630_9PSEU, A0A6P9EDV5_JUGRE, A0A7J6HWK0_CANSA, A0A0A0LS28_CUCSA, A0A7J7NVR3_9MAGN, A0A067GJM3_CITSI, A0A4D9BKT0_SALSN, A0A1S4CYK7_TOBAC, A0A6P6VR98_COFAR, A0A4D6LTH5_VIGUN, A0A2K3LEX3_TRIPR, A0A0S3T6G8_PHAAN, A0A443PVW3_9MAGN, A0A2G9FZN5_9LAMI, A0A1U8PR79_GOSHI, A0A6A6LX90_HEVBR, R0ICU6_9BRAS, A0A059CGB0_EUCGR, A0A087HMT0_ARAAL, A0A834D1Z4_JUGRE, V4MUL2_EUTSA, A0A2Z7AWR4_9LAMI, A0A6J1KOT4_CUCMA, A0A6D2K4G2_9BRAS, A0A6P4DEJ8_ARADU, A0A0D3DP49_BRAOL, A0A2Z6MG01_TRISU, A0A2R6QLR8_ACTCC, A0A2G2YJR6_CAPAN, W9S4J5_9ROSA, A0A0K9QVL8_SPIOL, A0A2P5EH62_TREOI, M4DK01_BRARP, A0A6A3CHP7_HIBSY, A0A0A0LUA1_CUCSA, A0A7J7GAQ8_CAMSI, A0A1J7HEA2_LUPAN, A0A6P5X977_DURZI, E4N8H2_KITSK, A0A1R3I2E8_COCAP, A0A067JAJ5_JATCU, A0A5B7BXG5_DAVIN, A0A5N6LCY2_9ASTR, A0A6A5MFA3_LUPAL, A0A061GGU3_THECC, A0A5J4ZAS9_9ASTE, A0A2G9GCR3_9LAMI, A0A0L9T8D7_PHAAN, A0A078IFW1_BRANA, F4K727_ARATH, A0A6A4M2C2_9ERIC, A0A2G9GCI8_9LAMI, A0A5N5KTU7_9ROSI, A0A0D3E3B6_BRAOL, A0A059CES8_EUCGR, I1LFR5_SOYBN, B9RXQ0_RICCO, A0A1G9VXW7_9FIRM, A0A3G2COM3_9LAMI, A0A078GYI7_BRANA, A0A2C9U7S3_MANES, A0A2I4H103_JUGRE, A0A7N2LS18_QUELO, A0A3N6TVX5_BRACR, A0A2U1L430_ARTAN, A0A538HDB3_9ACTN, A0A6D2L898_9BRAS, A0A803M210_CHEQI, and G7K113_MEDTR.

In some embodiments, exemplary sequences of natural E105G or G105 TrpB enzymes include Uniprot Reference IDs: A0A1Y2ES69_9FUNG, A0A3G2JB62_9ACTN, A0A497LHY2_9ARCH, A0A372JIS3_9ACTN, A0A4R2JTW3_9PSEU, A0A2G4DUKO_9PSED, A0A495XM74_9PSEU, A0A5B2WXY5_9PSEU, A0A2R4JYN6_9ACTN, A0A7X0HM14_9ACTN, A0A3M2M7Q1_9ACTN, A0A2Z5JNA3_STRAR, A0A1D2I6R8_9ACTN, A4X2Q5_SALTO, A8M857_SALAI, A0A2Z6MHK3_TRISU, A0A2Z6LYX2_TRISU, A0A2N3YOW9_SACSN, A0A3M2LT27_9ACTN, A0A1Y2BZ46_9FUNG, A0A7XOFYK7_9ACTN, A0A6G9YC57_9NOCA, A0A0M8Y7G9_9PSEU, A0A3N6FU51_9ACTN, A0A2E8ECVO_9ARCH, A0A1ROKQZ8_9PSEU, A0A6HOCF22_9ACTN, A0A1Q7C2E5_9ACTN, A0A3BOBZ99_9ACTN, A0A1I5FKD1_9PSEU, S5V8Y4_STRC3, A0A5DOTYB6_9ACTN, A0A2W2CSIO_9ACTN, A0A7J3BCK0_9ARCH, A0A524MXN4_9ARCH, A0A250J5N8_9DELT, A0A059W1L0_STRA9, A0A231PSJ6_9ACTN, A0A1Q5G5Y6_9ACTN, A0A428WWG2_AMYBA, A0A7Y6XJ27_9DELT, A0A239HBT6_9ACTN, A0A810N257_9ACTN, A0A1Y3NJG2_PIRSE, A0A0K3BQJ8_9PSEU, A0A0N0MMZ3_9ACTN, A0A169PRX3_STRLU, A0A4Y8Q7I8_9BACL, A0A5C6J162_9ACTN, A0A4R4QIN3_9ACTN, A0A1C4NQE4_9ACTN, A0A7C7QDZ0_9ARCH, A0A1Y1VNX0_9FUNG, A0A118HX14_9BURK, A0A7Y9BJN1_9ACTN, R1I7Z1_9PSEU, A0A1I6RW19_9ACTN, A0A640S584_9ACTN, A0A7K3HEY3_9ACTN, W5WN33_9PSEU, A0A7Y9EB40_9ACTN, A0A4R5BHL3_9ACTN, and A0A1B2HMU5_9PSEU.

Mutational methods of generating diversity include, for example, error-prone PCR mutagenesis (Cadwell & Joyce (1992) *Genome Res.*, 2:28-33); site-directed mutagenesis (Ling et al. (1997) *Anal Biochem.* 254 (2): 157-178; Dale et al. (1996) *Methods Mal. Biol.* 57:369-374; Smith (1985) *Ann. Rev. Genet.* 19:423-462; Botstein & Shortle (1985) *Science* 229:1193-1201; Carter (1986) *Biochem. J* 237:1-7; and Kunkel (1987) in *Nucleic Acids & Molecular Biology* (Eckstein, F. and Lilley, D. M. J. eds., Springer Verlag, Berlin)); mutagenesis using uracil containing templates (Kunkel (1985) *Proc. Natl. Acad Sci. USA* 82:488-492; Kunkel et al. (1987) *Methods in Enzymol.* 154, 367-382; and Bass et al. (1988) *Science* 242:240-245); oligonucleotide-directed mutagenesis (*Methods in Enzymol.* 100:468-500 (1983); *Methods in Enzymol.* 154:329-350 (1987); Zoller & Smith (1982) *Nucleic Acids Res.* 10:6487-6500; Zoller & Smith (1983) *Methods in Enzymol.* 100:468-500; and Zoller & Smith (1987) *Methods in Enzymol.* 154:329-350); phosphorothioate-modified DNA mutagenesis (Taylor et al. (1985) *Nucl. Acids Res.* 13:8749-8764; Taylor et al. (1985) *Nucl. Acids Res.* 13:8765-8787; Nakamaye & Eckstein (1986) *Nucl. Acids Res.* 14:9679-9698; Sayers et al. (1988) *Nucl. Acids Res.* 16:791-802; and Sayers et al. (1988) *Nucl. Acids Res.* 16:803-814); mutagenesis using gapped duplex DNA (Kramer et al. (1984) *Nucl. AcidsRes.* 12:9441-9456; Kramer & Fritz (1987) *Methods in Enzymol.* 154:350-367; Kramer et al. (1988) *Nucl. Acids Res.* 16:7207; and Fritz et al. (1988) *Nucl. Acids Res.* 16:6987-6999).

Additional suitable methods include point mismatch repair (Kramer et al. (1984) *Cell* 38:879-887), mutagenesis using repair-deficient host strains (Carter et al. (1985) *Nucl. Acids Res.* 13:4431-4443; and Carter (1987) *Methods in Enzymol.* 154:382-403), deletion mutagenesis (Eghtedarza- deh & Henikoff (1986) *Nucl. Acids Res.* 14:5115), restriction-selection and restriction-purification (Wells et al. (1986) *Phil. Trans. R. Soc. Land A* 317:415-423), mutagenesis by total gene synthesis (Nambiar et al. (1984) *Science* 223:1299-1301; Sakamar and Khorana (1988) *Nucl. Acids Res.* 14:6361-6372; Wells et al. (1985) *Gene* 34:315-323; and Grundstrom et al. (1985) *Nucl. Acids Res.* 13:3305-3316); double-strand break repair (Mandecki (1986); *Arnold* (1993) *Current Opinion in Biotechnology* 4:450-455; and *Proc. Natl. Acad. Sci. USA*, 83:7177-7181).

Additional details regarding various diversity generating methods can be found in the following U.S. patents, PCT publications, and EPO publications: U.S. Pat. No. 5,605,793 to Stemmer (Feb. 25, 1997), U.S. Pat. No. 5,811,238 to Stemmer et al. (Sep. 22, 1998) U.S. Pat. No. 5,830,721 to Stemmer et al. (Nov. 3, 1998), U.S. Pat. No. 5,834,252 to Stemmer, et al. (Nov. 10, 1998) U.S. Pat. No. 5,837,458 to Minshull, et al. (Nov. 17, 1998), WO 95/22625, Stemmer and Crameri, WO 96/33207 by Stemmer and Lipschutz, WO 97/20078 by Stemmer and Crameri; WO 97/35966 by Minshull and Stemmer, WO 99/41402 by Punnonen et al., WO 99/41383 by Punnonen et al., WO 99/41369 by Punnonen et al., WO 99/41368 by Punnonen et al., EP 752008 by Stemmer and Crameri, EP 0932670 by Stemmer, WO 99/23107 by Stemmer et al., WO 99/21979 by Apt et al., WO 98/31837 by del Cardayre et al., WO 98/27230 by Patten and Stemmer, WO 98/13487 by Stemmer et al., WO 00/00632, WO 00/09679, WO 98/42832 by Arnold et al., WO 99/29902 by Arnold et al., WO 98/41653 by Vind, WO 98/41622 by Borchert et al., WO 98/42727 by Pati and Zarling, WO 00/18906 by Patten et al., WO 00/04190 by del Cardayre et al., WO 00/42561 by Crameri et al., WO 00/42559 by Selifonov and Stemmer, WO 00/42560 by Selifonov et al., WO 01/23401 by Welch et al., and WO 01/64864 by Affuolter.

Engineered TrpBs can include additional mutations, including but not limited to amino acid mutations that promote the formation and/or persistence of the amino-acrylate intermediate in the TrpB catalytic cycle. As used herein, the terms "amino-acrylate intermediate" and "E(A-A) intermediate" refer to a 4-substituted (E)-2-(((E)-(2-methyl-3-oxido-5-((phosphonooxy)-methyl)pyridin-4-yl)methylene)ammonia)but-2-enoate species according to Formula A-A:

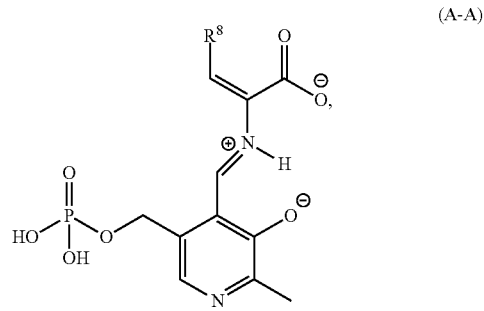

(A-A)

wherein $R^8$ is $C_{2-8}$ alkyl, which is optionally substituted with one or more $R^{8a}$, wherein each $R^{8a}$ is independently selected from the group consisting of halogen-OH, —CN, —N$_3$, —NO$_2$, $C_{1-12}$ alkyl, $C_{6-14}$ aryl, $C_{2-12}$ $C_{1-12}$ alkynyl, alkenyl, $C_{1-12}$ alkoxy, $C_{1-12}$ thioalkoxy, —N($R^{8b}$)$_2$, —C(O)$R^{8c}$, —C(O)N($R^{8b}$)$_2$, —NR$^{8b}$C(O)$R^{8c}$, and —OC(O)$R^{8c}$, wherein each $R^{8b}$ is independently selected from the group consisting of hydrogen and $C_{1-6}$ alkyl and wherein each $R^{8c}$ is independently selected from the group consisting of hydrogen, —OH, and halogen. One of skill in the art will appreciate that the amino-acrylate intermediate can exist in different tautomeric forms, where the ionizable functional groups (i.e., carboxylate, phosphate, phenolate, iminium) are protonated or deprotonated.

The effects of a particular mutation can be assessed spectroscopically as described in detail below. For example, incubation of TrpB with a serine substrate leads to formation of the amino-acrylate intermediate and a detectable absorbance at 350 nm. Hydrolysis of the-amino-acrylate intermediate can result in a partial or complete loss of the absorbance at 350 nm. Deamination of the hydrolyzed amino-acrylate, in turn, results in the formation of an α keto acid having a distinct, detectable absorbance at 320 nm. Accordingly, the effects of a particular mutation in promoting product formation (e.g., via formation of the amino-acrylate intermediate and/or its persistence during the TrpB catalytic cycle) can be readily determined by assessing the absorbance spectrum of a mixture containing the TrpB and the serine substrate. This can include measuring the absorbance at 350 nm (e.g., observing an increase in absorbance at 350 nm) and/or measuring the absorbance at 320 nm (e.g., finding that the absorbance at 320 nm does not increase with time).

TyrS Compositions

Described in the present disclosure is an engineered tryptophan synthase β-subunit (TrpB) comprising an amino acid substitution at a position corresponding to amino acid residue E105 of SEQ ID NO: 1. In some embodiments, the engineered TrpB catalyzes the synthesis of tyrosine or a tyrosine analog. In some embodiments, the engineered TrpB comprises an amino acid sequence at least 60% identical to SEQ ID NO: 1. In some embodiments, the engineered TrpB comprises an amino acid sequence at least 65% identical to SEQ ID NO: 1. In some embodiments, the engineered TrpB comprises an amino acid sequence at least 70% identical to SEQ ID NO: 1. In some embodiments, the engineered TrpB comprises an amino acid sequence at least 75% identical to SEQ ID NO: 1. In some embodiments, the engineered TrpB comprises an amino acid sequence at least 80% identical to SEQ ID NO: 1. In some embodiments, the engineered TrpB comprises an amino acid sequence at least 85% identical to SEQ ID NO: 1. In some embodiments, the engineered TrpB comprises an amino acid sequence at least 90% identical to SEQ ID NO: 1. In some embodiments, the engineered TrpB comprises an amino acid sequence at least 95% identical to SEQ ID NO: 1. In some embodiments, the engineered TrpB comprises an amino acid sequence at least 98% identical to SEQ ID NO: 1.

In some embodiments, the amino acid substitution of the engineered TrpB at the position corresponding to amino acid residue E105 of SEQ ID NO: 1 is selected from the group consisting of glycine (G), alanine (A), serine(S), and proline (P). In some embodiments, the engineered TrpB further comprises one or more amino acid substitutions at a position corresponding to an amino acid residue selected from the group consisting of Y4, Y12, P19, E30, F41, I69, A87, K96, I103, I128, K139, P140, L147, A150, N167, L170, I174, Y181, I184, H191, L213, V227, G228, G229, S265, W286, V291, T292, S302, and R389 of SEQ ID NO: 1.

In some embodiments, the amino acid substitution at the position corresponding to amino acid residue Y4 is N. In some embodiments, the amino acid substitution at the position corresponding to amino acid residue Y12 is N. In some embodiments, the amino acid substitution at the position corresponding to amino acid residue P19 is G. In some embodiments, the amino acid substitution at the position corresponding to amino acid residue E30 is G. In some embodiments, the amino acid substitution at the position corresponding to amino acid residue F41 is Y. In some embodiments, the amino acid substitution at the position corresponding to amino acid residue I69 is V. In some embodiments, the amino acid substitution at the position corresponding to amino acid residue A87 is T. In some embodiments, the amino acid substitution at the position corresponding to amino acid residue K96 is L. In some embodiments, the amino acid substitution at the position corresponding to amino acid residue I103 is T. In some embodiments, the amino acid substitution at the position corresponding to amino acid residue I128 is V. In some embodiments, the amino acid substitution at the position corresponding to amino acid residue K139 is R. In some embodiments, the amino acid substitution at the position corresponding to amino acid residue P140 is L. In some embodiments, the amino acid substitution at the position corresponding to amino acid residue L147 is Q. In some embodiments, the amino acid substitution at the position corresponding to amino acid residue A150 is V. In some embodiments, the amino acid substitution at the position corresponding to amino acid residue N167 is D. In some embodiments, the amino acid substitution at the position corresponding to amino acid residue L170 is F. In some embodiments, the amino acid substitution at the position corresponding to amino acid residue I174 is T. In some embodiments, the amino acid substitution at the position corresponding to amino acid residue Y181 is H. In some embodiments, the amino acid substitution at the position corresponding to amino acid residue I184 is F, P, or A. In some embodiments, the amino acid substitution at the position corresponding to amino acid residue H191 is Y. In some embodiments, the amino acid substitution at the position corresponding to amino acid residue L213 is P. In some embodiments, the amino acid substitution at the position corresponding to amino acid residue V227 is M. In some embodiments, the amino acid substitution at the position corresponding to amino acid residue G228 is S. In some embodiments, the amino acid substitution at the position corresponding to amino acid residue G229 is A. In some embodiments, the amino acid substitution at the position corresponding to amino acid residue S265 is P. In some embodiments, the amino acid substitution at the position corresponding to amino acid residue W286 is G. In some embodiments, the amino acid substitution at the position corresponding to amino acid residue V291 is A. In some embodiments, the amino acid substitution at the position corresponding to amino acid residue T292 is S. In some embodiments, the amino acid substitution at the position corresponding to amino acid residue S302 is P. In some embodiments, the amino acid substitution at the position corresponding to amino acid residue R389 is H.

In some embodiments, the engineered TrpB comprises the following amino acid substitutions relative to SEQ ID NO: 1: P19G, E30G, I69V, K96L, E105G, P140L, N167D, I184F, L213P, G228S, and T292S. In some embodiments, the engineered TrpB comprises SEQ ID NO: 1 having the following amino acid substitutions: P19G, E30G, I69V, K96L, E105G, P140L, N167D, I184F, L213P, G228S, and T292S ("Tm9D8*E105G"; Table 1).

In some embodiments, the engineered TrpB comprises the following amino acid substitutions relative to SEQ ID NO: 1: Y4N, Y12N, P19G, E30G, F41Y, I69V, K96L, I103T, E105G, P140L, N167D, I184P, L213P, G228S, V291A, T292S, S302P, and R389H. In some embodiments, the engineered TrpB comprises SEQ ID NO: 1 having the following amino acid substitutions: Y4N, Y12N, P19G, E30G, F41Y, I69V, K96L, I103T, E105G, P140L, N167D, I184P, L213P, G228S, V291A, T292S, S302P, and R389H ("TmTyrS1"; Table 1).

In some embodiments, the engineered TrpB comprises the following amino acid substitutions relative to SEQ ID NO: 1: Y4N, Y12N, P19G, E30G, F41Y, I69V, A87T, K96L, I103T, E105G, I128V, P140L, N167D, I184P, H191Y, L213P, G228S, V291A, T292S, S302P, and R389H. In some embodiments, the engineered TrpB comprises SEQ ID NO: 1 having the following amino acid substitutions: Y4N, Y12N, P19G, E30G, F41Y, I69V, A87T, K96L, I103T, E105G, I128V, P140L, N167D, I184P, H191Y, L213P, G228S, V291A, T292S, S302P, and R389H ("TmTyrS2"; Table 1).

In some embodiments, the engineered TrpB comprises the following amino acid substitutions relative to SEQ ID NO: 1: Y4N, Y12N, P19G, E30G, F41Y, I69V, A87T, K96L, I103T, E105G, I128V, P140L, L147Q, N167D, I184P, H191Y, L213P, V227M, G228S, V291A, T292S, S302P, and R389H. In some embodiments, the engineered TrpB comprises SEQ ID NO: 1 having the following amino acid substitutions: Y4N, Y12N, P19G, E30G, F41Y, I69V, A87T, K96L, I103T, E105G, I128V, P140L, L147Q, N167D, I184P, H191Y, L213P, V227M, G228S, V291A, T292S, S302P, and R389H ("TmTyrS3"; Table 1).

In some embodiments, the engineered TrpB comprises the following amino acid substitutions relative to SEQ ID NO: 1: Y4N, Y12N, P19G, E30G, F41Y, I69V, A87T, K96L, I103T, E105G, I128V, P140L, L147Q, N167D, I174T, I184A, H191Y, L213P, V227M, G228S, S265P, V291A, T292S, S302P, and R389H. In some embodiments, the engineered TrpB comprises SEQ ID NO: 1 having the following amino acid substitutions: Y4N, Y12N, P19G, E30G, F41Y, I69V, A87T, K96L, I103T, E105G, I128V, P140L, L147Q, N167D, I174T, I184A, H191Y, L213P, V227M, G228S, S265P, V291A, T292S, S302P, and R389H ("TmTyrS4"; Table 1).

In some embodiments, the engineered TrpB comprises the following amino acid substitutions relative to SEQ ID NO: 1: Y4N, Y12N, P19G, E30G, F41Y, I69V, A87T, K96L, I103T, E105G, I128V, P140L, L147Q, A150V, N167D, I174T, Y181H, I184A, H191Y, L213P, V227M, G228S, G229A, V291A, T292S, S302P, and R389H. In some embodiments, the engineered TrpB comprises SEQ ID NO: 1 having the following amino acid substitutions: Y4N, Y12N, P19G, E30G, F41Y, I69V, A87T, K96L, I103T, E105G, I128V, P140L, L147Q, A150V, N167D, I174T, Y181H, I184A, H191Y, L213P, V227M, G228S, G229A, V291A, T292S, S302P, and R389H ("TmTyrS5"; Table 1).

In some embodiments, the engineered TrpB comprises the following amino acid substitutions relative to SEQ ID NO: 1: Y4N, Y12N, P19G, E30G, F41Y, I69V, A87T, K96L, I103T, E105G, I128V, K139R, P140L, L147Q, A150V, N167D, L170F, I174T, Y181H, I184A, H191Y, L213P, V227M, G228S, G229A, W286G, V291A, T292S, S302P, and R389H. In some embodiments, the engineered TrpB comprises SEQ ID NO: 1 having the following amino acid substitutions: Y4N, Y12N, P19G, E30G, F41Y, I69V, A87T, K96L, I103T, E105G, I128V, K139R, P140L, L147Q, A150V, N167D, L170F, I174T, Y181H, I184A, H191Y, L213P, V227M, G228S, G229A, W286G, V291A, T292S, S302P, and R389H ("TmTyrS6"; Table 1).

TABLE 1

Summary of amino acid substitutions in exemplary engineered TrpB enzymes.

| Variant | Reference Variant | Amino acid substitutions |
|---|---|---|
| Tm9D8* (SEQ ID NO: 3) | WT TmTrpB (SEQ ID NO: 1) | P19G, E30G, I69V, K96L, P140L, N167D, I184F, L213P, G228S, T292S |
| Tm9D8* E105G (SEQ ID NO: 4) | Tm9D8* | E105G |
| TmTyrS1 (SEQ ID NO: 6) | Tm9D8* E105G | Y4N, Y12N, F41Y, I103T, F184P, V291A, S302P, R389H |
| TmTyrS2 (SEQ ID NO: 7) | TmTyrS1 | A87T, I128V, H191Y |
| TmTyrS3 (SEQ ID NO: 8) | TmTyrS2 | L147Q, V227M |
| TmTyrS4 (SEQ ID NO: 9) | TmTyrS3 | I174T, P184A, S265P |
| Tm TyrS5 (SEQ ID NO: 10) | TmTyrS4 | A150V, Y181H, G229A, P265S |
| Tm TyrS6 (SEQ ID NO: 11) | TmTyrS5 | K139R, L170F, W286G |

Also described in the present disclosure is an engineered tryptophan synthase β-subunit (TrpB) comprising the amino acid sequence of any one of SEQ ID NOS: 4-11. In some embodiments, the present disclosure provides an isolated polynucleotide comprising a nucleotide sequence encoding the engineered TrpB.

In some embodiments, the engineered TrpB associates with the substrate at a temperature of at least 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In some embodiments, the first substrate is (a) donor amino acid and the second substrate is (b) a phenol or phenol analog. In some embodiments, the donor amino acid is a β-hydroxy amino acid. In some embodiments, the β-hydroxy amino acid is threonine or serine. In some embodiments, the β-hydroxy amino acid is L-threonine. In some embodiments, the β-hydroxy amino acid is L-serine. In some embodiments, the donor amino acid is a β-chloroalanine. In some embodiments, the donor amino acid is S-(o-nitrophenyl)-L-cysteine.

In some embodiments, the compound is a tyrosine or a tyrosine analog. In some embodiments, the tyrosine is L-tyrosine. In some embodiments, the tyrosine analog is selected from the group consisting of 2-amino-3-(4-hydroxy-3-(methylthio)phenyl)propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl)propanoic acid, 2-amino-3-(3-fluoro-4-hydroxyphenyl)propanoic acid, 2-amino-3-(4-hydroxy-3-methoxyphenyl)propanoic acid, 2-amino-3-(3-bromo-4-hydroxyphenyl)propanoic acid, 2-amino-3-(3,5-dichloro-4-hydroxyphenyl)propanoic acid, 2-amino-3-(4-hydroxy-3,5-dimethylphenyl)propanoic acid, 2-amino-3-(2-fluoro-4-hydroxyphenyl)propanoic acid, 2-amino-3-(2-chloro-4-hydroxyphenyl)propanoic acid, 2-amino-3-(4-hydroxy-2-methylphenyl)propanoic acid, 2-amino-3-(2,3,5,6-tetrafluoro-4-hydroxyphenyl)propanoic acid, and 2-amino-3-(4-hydroxynaphthalen-1-yl)butanoic acid.

Also provided herein are methods for preparing a compound with the engineered TrpB, wherein the compound is tyrosine or a tyrosine analog or a salt thereof, the method comprising combining: (i) a donor amino acid; (ii) phenol or a phenol analog; and (iii) the engineered TrpB in a reaction mixture; and maintaining the reaction mixture under conditions sufficient to form the compound. In some embodiments, the donor amino acid is a β-hydroxy amino acid.

In some embodiments, the compound is a tyrosine or a tyrosine analog. In some embodiments, the tyrosine is L-tyrosine. In some embodiments, the tyrosine analog is selected from the group consisting of 2-amino-3-(4-hydroxy-3-(methylthio)phenyl)propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl)propanoic acid, 2-amino-3-(3-fluoro-4-hydroxyphenyl)propanoic acid, 2-amino-3-(4-hydroxy-3-methoxyphenyl)propanoic acid, 2-amino-3-(3-bromo-4-hydroxyphenyl)propanoic acid, 2-amino-3-(3,5-dichloro-4-hydroxyphenyl)propanoic acid, 2-amino-3-(4-hydroxy-3,5-dimethylphenyl)propanoic acid, 2-amino-3-(2-fluoro-4-hydroxyphenyl)propanoic acid, 2-amino-3-(2-chloro-4-hydroxyphenyl)propanoic acid, 2-amino-3-(4-hydroxy-2-methylphenyl)propanoic acid, 2-amino-3-(2,3,5,6-tetrafluoro-4-hydroxyphenyl)propanoic acid, and 2-amino-3-(4-hydroxynaphthalen-1-yl)butanoic acid.

In some embodiments, the β-hydroxy amino acid is threonine or serine. In some embodiments, the β-hydroxy amino acid is L-threonine. In some embodiments, the β-hydroxy amino acid is L-serine. In some embodiments, the phenol analog is selected from the group consisting of 2-(methylthio) phenol, 2-iodophenol, 2-chlorophenol, o-cresol, 2-fluorophenol, 2-bromophenol, 2-methoxyphenol, 2,6-dichlorophenol, 3-fluorophenol, 3-chlorophenol, m-cresol, 2,3,5,6-tetrafluorophenol, naphthalen-1-ol, and 2,6-dimethylphenol.

Methods for Preparing Compounds Using TYRS

Provided herein are methods for preparing a compound of Formula I:

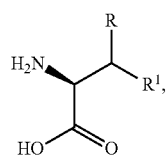
(I)

or a salt thereof,
wherein R is (A), (B), or (C):

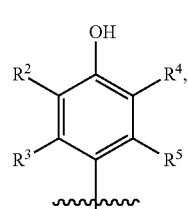
(A)

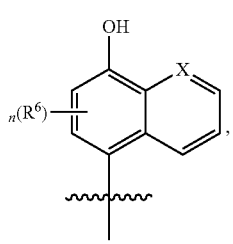
(B)

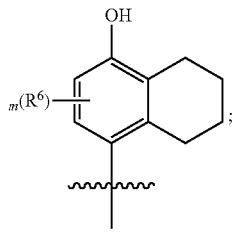
(C)

The methods include combining: (i) a β-hydroxy amino acid; (ii) phenol or a phenol analog; and (iii) the engineered TrpB in a reaction mixture; and maintaining the reaction mixture under conditions sufficient to form the compound according to Formula I.

In some embodiments, the substrate concentration may be 5 mM. In some embodiments, the substrate concentration may be 100 mM. In some embodiments, the substrate concentration may be 5, 10, 15, 20, 25, 30, 35, 40, 45, 50, 55, 60, 65, 70, 75, 80, 85, 90, 95, and 100 mM. In some embodiments, the substrate concentration may range from 5-10 mM, 10-15 mM, 15-20 mM, 20-25 mM, 25-30 mM, 30-35 mM, 35-40 mM, 40-45 mM, 45-50 mM, 50-55 mM, 55-60 mM, 60-65 mM, 65-70 mM, 70-75 mM, 75-80 mM, 80-85 mM, 85-90 mM, 90-95 mM, and 95-100 mM. In some embodiments, the substrate concentration may range from 4-9 mM, 9-14 mM, 14-19 mM, 19-24 mM, 24-29 mM, 29-34 mM, 34-39 mM, 39-44 mM, 44-49 mM, 49-54 mM, 54-59 mM, 59-64 mM, 64-69 mM, 69-74 mM, 74-79 mM, 79-84 mM, 84-89 mM, 89-94 mM, 94-99 mM. In some embodiments, the substrate concentration may be at least 100 mM.

For compounds of Formula I:
$R^1$ is hydrogen or $C_{1-8}$ alkyl, which is optionally substituted with one or more $R^{1a}$;
each $R^{1a}$ is independently selected from the group consisting of hydrogen, halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{1b}$)$_2$, —C(O)$R^{1c}$, —C(O)N($R^{1b}$)$_2$, —N$R^{1b}$C(O)$R^{1c}$, and —OC(O)$R^{1c}$;
each $R^{1b}$ is independently selected from the group consisting of hydrogen and $C_{1-6}$ alkyl;
each $R^{1c}$ is independently selected from the group consisting of hydrogen, —OH, halogen, $C_{1-6}$ alkyl, $C_{1-6}$ alkoxy;
$R^2$, $R^3$, $R^4$, and $R^5$ are independently selected from the group consisting of hydrogen, halogen, $C_{1-8}$ alkyl, which is optionally substituted with one or more $R^{2a}$;
each $R^{2a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{2b}$)$_2$, —C(O)$R^{2c}$, —C(O)N($R^{2b}$)$_2$, —N$R^{2b}$C(O)$R^{2c}$, and —OC(O)$R^{2c}$;
each $R^{2b}$ is independently selected from the group consisting of hydrogen and $C_{1-6}$ alkyl;
each $R^{2c}$ is independently selected from the group consisting of hydrogen, —OH, halogen, $C_{1-6}$ alkyl, $C_{1-6}$ alkoxy;
$R^6$ is hydrogen or $C_{1-8}$ alkyl, which is optionally substituted with one or more $R^{3a}$;
each $R^{3a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

- each R$^{3b}$ is independently selected from the group consisting of hydrogen and C$_{1-6}$ alkyl;
- each R$^{3c}$ is independently selected from the group consisting of hydrogen, —OH, halogen, C$_{1-6}$ alkyl, C$_{1-6}$ alkoxy;
- n is selected from 0, 1, 2, 3, 4, or 5;
- m is selected from 0, 1, 2, 3, 4, 5, or 6;
- X is —C(R$^7$) or —N;
- wherein R$^7$ is hydrogen or C$_{1-8}$ alkyl, which is optionally substituted with one or more R$^{4a}$;
- each R$^{4a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^4$;
- each R$^{4b}$ is independently selected from the group consisting of hydrogen and C$_{1-6}$ alkyl; and
- each R$^4$ is independently selected from the group consisting of hydrogen, —OH, halogen, C$_{1-6}$ alkyl, C$_{1-6}$ alkoxy.

In some embodiments, the engineered TrpB is a thermophilic TrpB. In some embodiments, the thermophilic TrpB is selected from the group consisting of T. maritima TrpB, a P. furiosis TrpB, an A. fulgidus Trp. B, a T. naphthophila TrpB, a T. petrophila TrpB, a T. neapolitana TrpB, a C. subterraneus TrpB, a D. tunisiensi TrpB, a D. kuznetsovii TrpB, a P. mobilis TrpB, an A. aeolicus TrpB, an S. azorense TrpB, a T. pseudethanolicus TrpB, a T. thermophilus TrpB, a P. abyssi TrpB, an M. jannaschii TrpB, a T. kodakarensis TrpB, and an M. aeolicus TrpB.

In some embodiments, the reaction mixture is maintained at a temperature ranging from about 20° C. to about 80° C.

In some embodiments of Formula I, R$^1$ is hydrogen. In some embodiments of Formula I, R$^1$ is C$_{1-8}$ alkyl.

Further provided herein are methods for preparing a compound of Formula II:

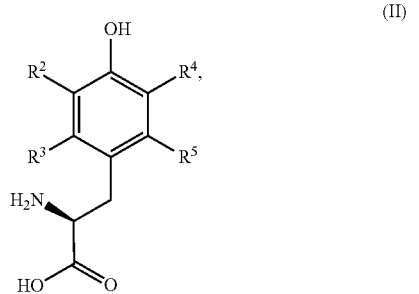

(II)

or a salt thereof.

The methods include combining: (i) a β-hydroxy amino acid; (ii) phenol or a phenol analog; and (iii) the engineered TrpB in a reaction mixture; and maintaining the reaction mixture under conditions sufficient to form the compound according to Formula II.

For compounds of Formula II:
- R$^2$, R$^3$, R$^4$, and R$^5$ are independently selected from the group consisting of hydrogen, halogen, C$_{1-8}$ alkyl, which is optionally substituted with one or more R$^{2a}$;
- each R$^{2a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{2b}$)$_2$, —C(O)R$^{2c}$, —C(O)N(R$^{2b}$)$_2$, —NR$^{2b}$C(O)R$^{2c}$, and —OC(O)R$^{2c}$;
- each R$^{2b}$ is independently selected from the group consisting of hydrogen and C$_{1-6}$ alkyl; and
- each R$^{2c}$ is independently selected from the group consisting of hydrogen, —OH, halogen, C$_{1-6}$ alkyl, C$_{1-6}$ alkoxy.

In some embodiments, the engineered TrpB is a thermophilic TrpB. In some embodiments, the thermophilic TrpB is selected from the group consisting of T. maritima TrpB, a P. furiosis TrpB, an A. fulgidus Trp. B, a T. naphthophila TrpB, a T. petrophila TrpB, a T. neapolitana TrpB, a C. subterraneus TrpB, a D. tunisiensi TrpB, a D. kuznetsovii TrpB, a P. mobilis TrpB, an A. aeolicus TrpB, an S. azorense TrpB, a T. pseudethanolicus TrpB, a T. thermophilus TrpB, a P. abyssi TrpB, an M. jannaschii TrpB, a T. kodakarensis TrpB, and an M. aeolicus TrpB.

In some embodiments, the reaction mixture is maintained at a temperature ranging from about 20° C. to about 80° C.

Also provided herein are methods of preparing a compound of Formula III:

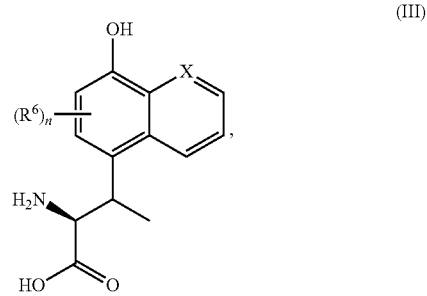

(III)

or a salt thereof.

The methods include combining: (i) a β-hydroxy amino acid; (ii) phenol or a phenol analog; and (iii) the engineered TrpB in a reaction mixture; and maintaining the reaction mixture under conditions sufficient to form the compound according to Formula III.

For compounds of Formula III:
- R$^6$ is hydrogen or C$_{1-8}$ alkyl, which is optionally substituted with one or more R$^{3a}$;
- each R$^{3a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;
- each R$^{3b}$ is independently selected from the group consisting of hydrogen and C$_{1-6}$ alkyl;
- each R$^{3c}$ is independently selected from the group consisting of hydrogen, —OH, halogen, C$_{1-6}$ alkyl, C$_{1-6}$ alkoxy;
- n is selected from 0, 1, 2, 3, 4, or 5;
- m is selected from 0, 1, 2, 3, 4, 5, or 6;
- X is —C(R$^7$) or —N;
- wherein R$^7$ is hydrogen or C$_{1-8}$ alkyl, which is optionally substituted with one or more R$^{4a}$;
- each R$^{4a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^{4c}$;
- each R$^{4b}$ is independently selected from the group consisting of hydrogen and C$_{1-6}$ alkyl; and each R[4] is independently selected from the group consisting of hydrogen, —OH, halogen, $C_{1-6}$ alkyl, $C_{1-6}$ alkoxy.

In some embodiments, the engineered TrpB is a thermophilic TrpB. In some embodiments, the thermophilic TrpB is selected from the group consisting of *T. maritima* TrpB, a *P. furiosis* TrpB, an *A. fulgidus* Trp. B, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T. thermophilus* TrpB, a *P. abyssi* TrpB, an *M. jannaschii* TrpB, a *T. kodakarensis* TrpB, and an *M. aeolicus* TrpB.

In some embodiments, the reaction mixture is maintained at a temperature ranging from about 20° C. to about 80° C.

In some embodiments, the compounds formed by the methods of the present disclosure are selected from the group consisting of:

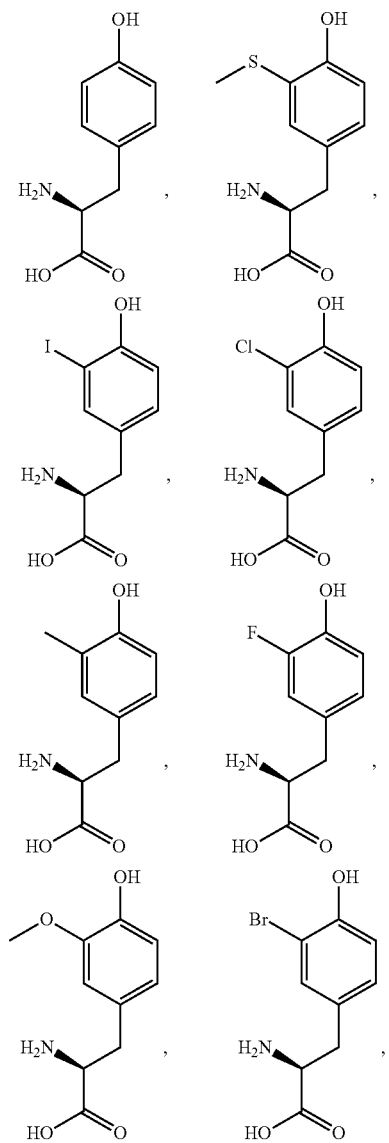

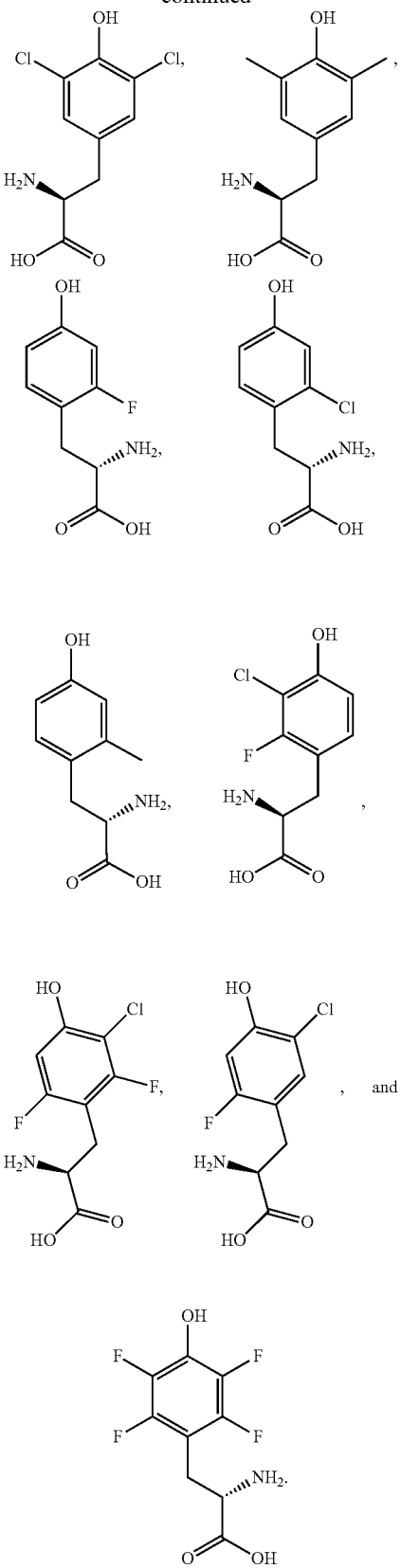

In some embodiments, the compound formed by the methods of the present disclosure has a structure of:

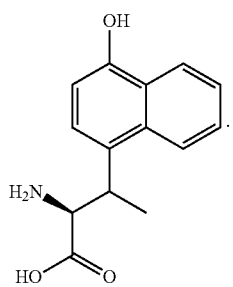 [SMILES: CC(c1ccc(O)c2ccccc12)[C@H](N)C(=O)O]

The methods provided herein generally include forming reaction mixtures that comprise a phenol substrate or phenol analog substrate, a serine substrate, and a engineered TrpB as described above. In some embodiments, the method is carried out in vitro. In other embodiments, the engineered TrpB is localized within a whole cell and the method is carried out in vivo. In some embodiments, the engineered TrpB is expressed in a bacterial, archaeal, yeast or fungal host organism. In some embodiments, the method is carried out under anaerobic conditions. In other embodiments, the process is carried out under aerobic conditions.

Reaction mixtures can contain additional reagents. As non-limiting examples, the reaction mixtures can contain buffers (e.g., M9-N buffer, 2-(N-morpholino) ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, isopropanol, glycerol, tetrahydrofuran, acetone, acetonitrile, and acetic acid), salts (e.g., NaCl, KCl, $CaCl_2$), and salts of $Mn^{2+}$ and $Mg^{2+}$), denaturants (e.g., urea and guanadinium hydrochloride), detergents (e.g., sodium dodecylsulfate and Triton-X 100), chelators (e.g., ethylene glycol-bis (2-aminoethylether)-N,N,N',N'-tetraacetic acid (EGTA), 2-({2-[Bis(carboxymethyl)amino]ethyl}(carboxymethyl)amino) acetic acid (EDTA), and 1,2-bis (o-aminophenoxy)ethane-N,N,N',N'-tetraacetic acid (BAPTA)), sugars (e.g., glucose, sucrose, and the like), and reducing agents (e.g., sodium dithionite, NADPH, dithiothreitol (DTT), β-mercaptoethanol (BME), and tris(2-carboxyethyl)phosphine (TCEP)). Buffers, cosolvents, salts, denaturants, detergents, chelators, sugars, and reducing agents can be used at any suitable concentration, which can be readily determined by one of skill in the art. In general, buffers, cosolvents, salts, denaturants, detergents, chelators, sugars, and reducing agents, if present, are included in reaction mixtures at concentrations ranging from about 1 µM to about 1 M. For example, a buffer, a cosolvent, a salt, a denaturant, a detergent, a chelator, a sugar, or a reducing agent can be included in a reaction mixture at a concentration of about 1 µM, or about 10 µM, or about 100 µM, or about 1 mM, or about 10 mM, or about 25 mM, or about 50 mM, or about 100 mM, or about 250 mM, or about 500 mM, or about 1 M. In some embodiments, a reducing agent is used in a sub-stoichiometric amount with respect to the olefin substrate and the diazo reagent. Cosolvents, in particular, can be included in the reaction mixtures in amounts ranging from about 1% v/v to about 75% v/v, or higher. A cosolvent can be included in the reaction mixture, for example, in an amount of about 5, 10, 20, 30, 40, or 50% (v v).

Reactions are conducted under conditions sufficient to catalyze the formation of the amino acid product. The reactions can be conducted at any suitable temperature. In general, the reactions are conducted at a temperature of from about 4° C. to about 80° C. The reactions can be conducted, for example, at about 25° C., or about 37° C., or about 50° C., or about 75° C. In some embodiments, the reactions are conducted at a temperature of from about 20° C. to about 80° C. (e.g., 25-75° C., or 25-50° C., or 25-40° C.). The engineered TrpBs can be heat treated. In some embodiments, heat treatment occurs at a temperature of at least about 75° C. The reactions can be conducted at any suitable pH. In general, the reactions are conducted at a pH of from about 6 to about 10. The reactions can be conducted, for example, at a pH of from about 6.5 to about 9 (e.g., about 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0). The reactions can be conducted for any suitable length of time. In general, the reaction mixtures are incubated under suitable conditions for anywhere between about 1 minute and several days. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours, or about 48 hours, or about 72 hours. The reactions can be conducted for about 1 to 4 hours (e.g., 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3,3.1, 3.2, 3.3, 3.4, 3.5, 3.6, 3.7, 3.8, 3.9, or 4 hours). Reactions can be conducted under aerobic conditions or anaerobic conditions. Reactions can be conducted under an inert atmosphere, such as a nitrogen atmosphere or argon atmosphere. In some embodiments, a solvent is added to the reaction mixture. In some embodiments, only water miscible solvents are used. In some embodiments, the solvent forms a second phase, and the phenol or phenol analog addition to the amino-acrylate intermediate occurs in the aqueous phase. In some embodiments, the engineered TrpB is located in the aqueous layer whereas the substrates and/or products occur in an organic layer. Other reaction conditions may be employed in the methods, depending on the identity of a particular engineered TrpB, phenol, phenol analog, or serine.

The methods described herein can be assessed in terms of the diastereoselectivity and/or enantioselectivity of phenol and phenol analog addition to the amino-acrylate intermediate, that is, the extent to which the reaction produces a particular isomer, whether a diastereomer or enantiomer. A perfectly selective reaction produces a single isomer, such that the isomer constitutes 100% of the product. As another non-limiting example, a reaction producing a particular enantiomer constituting 90% of the total product can be said to be 90% enantioselective. A reaction producing a particular diastereomer constituting 30% of the total product, meanwhile, can be said to be 30% diastereoselective.

In general, the methods described herein include reactions that are from about 1% to about 99% diastereoselective. The reactions are from about 1% to about 99% enantioselective. The reaction can be, for example, from about 10% to about 90% diastereoselective, or from about 20% to about 80% diastereoselective, or from about 40% to about 60% diastereoselective, or from about 1% to about 25% diastereoselective, or from about 25% to about 50% diastereoselective, or from about 50% to about 75% diastereoselective. The reaction can be about 10%, 15%, 20%, 25%, 30%, 35%, 40%, 45%, 50%, 55%, 60%, 65%, 70%, 75%, 80%, 85%, 90%, or about 95% diastereoselective. The reaction can be from about 10% to about 90% enantioselective, from about 20% to about 80% enantioselective, or from about 40% to about 60% enantioselective, or from about 1% to about 25% enantioselective, or from about 25% to about 50% enantioselective, or from about 50% to about 75% enantioselective. The reaction can be about 10%, 15%, 20%, 25%, 30%, 35%, 40%, 45%, 50%, 55%, 60%, 65%, 70%, 75%, 80%, 85%, 90%, or about 95% enantioselective. Accordingly some embodiments provide methods wherein the reaction is at least 30% to at least 90% diastereoselective. In some embodiments, the reaction is at least 30% to at least 90% enantioselective. Preferably, the reaction is at least 80% (e.g., at least about 80%, 81%, 82%, 83%, 84%, 85%, 86%, 87%, 88%, 89%, 90%, 91%, 92%, 93%, 94%, 95%, 96%, 97%, 98%, 99%, or 100%) enantioselective. More preferably, the reaction is at least 90% (e.g., at least about 90%, 91%, 92%, 93%, 94%, 95%, 96%, 97%, 98%, 99%, or 100%) enantioselective.

Compounds

In some aspects, the present disclosure provides compounds of Formula I:

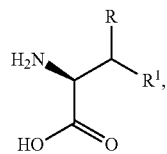

(I)

or a salt thereof, wherein:

R is (B) or (C):

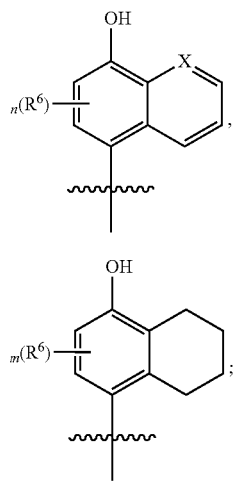

(B)

(C)

$R^1$ is hydrogen or $C_{1-8}$ alkyl, which is optionally substituted with one or more $R^{1a}$;

each $R^{1a}$ is independently selected from the group consisting of hydrogen, halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$)$_2$, —C(O)R$^{1c}$, —C(O)N(R$^{1b}$)$_2$, —NR$^{1b}$C(O)R$^{1c}$, and —OC(O)R$^{1c}$;

each $R^{1b}$ is independently selected from the group consisting of hydrogen and $C_{1-6}$ alkyl;

each $R^{1c}$ is independently selected from the group consisting of hydrogen, —OH, halogen, $C_{1-6}$ alkyl, $C_{1-6}$ alkoxy;

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C(R$^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^{4c}$;

each $R^{4b}$ is independently selected from the group consisting of hydrogen and $C_{1-6}$ alkyl; and each $R^4$ is independently selected from the group consisting of hydrogen, —OH, halogen, $C_{1-6}$ alkyl, $C_{1-6}$ alkoxy.

In some aspects, the present disclosure provides compounds of Formula III:

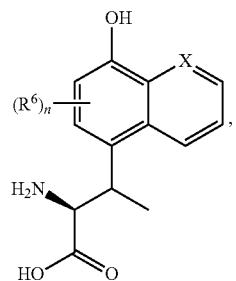

(III)

or a salt thereof, wherein:

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C(R$^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, $-N(R^{4b})_2$, $-C(O)R^{4c}$, $-C(O)N(R^{4b})_2$, $-NR^{4b}C(O)R^{4c}$, and $-OC(O)R^{4c}$;

each $R^{4b}$ is independently selected from the group consisting of hydrogen and $C_{1-6}$ alkyl; and each R is independently selected from the group consisting of hydrogen, $-OH$, halogen, $C_{1-6}$ alkyl, $C_{1-6}$ alkoxy.

In some embodiments, the compound has a structure selected from the group consisting of:

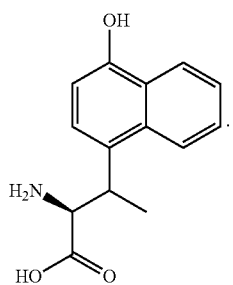 [SMILES: CC(c1ccc(O)c2ccccc12)[C@H](N)C(=O)O]

EXAMPLES

Example 1: Materials and Methods

Chemicals were purchased from commercial sources and used without additional purification. Analytical LCMS was performed on an AGILENT® 1260 Infinity II LC/MSD iQ (Agilent Technologies, Inc., Santa Clara, CA) equipped with a reversed-phase POROSHELL® 120 EC-C18 (Agilent Technologies, Inc., Santa Clara, CA), 4.6×50 mm, 2.7 μm column using a gradient of $H_2O$/MeCN with 0.1% acetic acid by volume. Unless otherwise stated, the gradient applied was 1-95% MeCN over 3 minutes, then held for 0.5 minutes, then immediately dropped to 1% MeCN for 0.5 minutes. NMR spectra were collected on a BRUKER® 400 MHz (100 MHz) spectrometer (Bruker Scientific Instruments, Billerica, MA) equipped with a cryogenic probe. Proton chemical shifts are reported in parts per million (ppm) relative to tetramethylsilane and calibrated using the residual solvent resonance ($H_2O$/HDO in D20, 4.79 ppm). Regioselectivities were determined by LCMS comparison to known standards when they could be chromatographically separated and by performing NMR experiments when sufficient product could be isolated. Preparative reversed-phase chromatography was used to isolate Tyr analog products on a BIOTAGE® ISOLERA™ One purification system (Biotage AB, Uppsala, Sweden) equipped with a C-18 column, using acidified $H_2O$ (0.01% of either HCl by weight when HCl salt was to be isolated, or acetic acid by volume when the pure product was to be isolated) as the weak solvent and MeCN as the strong solvent.

Example 2: Cloning, Expression, and Purification of TyrS Variants

TyrS genes were cloned into pET22b (+) between the NdeI and XhoI restriction sites, in frame with the Lac-inducible T7 promotor and C-terminal 6xHis tag for expression in transformed BL21 (DE3) Escherichia coli cells (E. coli). Single colonies of E. coli harboring TyrS variants were isolated on Lysogeny Broth (LB) agar medium supplemented with 100 μg/mL carbenicillin. For large-scale expression, a single colony was transferred to 5 mL of LB with 100 μg/mL carbenicillin ($LB_{carb}$) and grown to stationary phase at 37° C. and 230 rpm. The culture was then diluted 1:250 into 250 mL Terrific Broth supplemented with 100 μg/mL carbenicillin ($TB_{carb}$) and grown for 6 hours at 37° C. at 250 rpm. Protein expression was induced with 1 mM isopropyl β-D-thiogalactopyranoside (IPTG) and proceeded at 30° C. for 24 hours. Cells were harvested via centrifugation at 5000 g for 10 minutes, the supernatant discarded, and then the cells were stored at −20° C. until needed.

To purify, thawed pellets were resuspended to 10 mL with a lysis buffer containing 25 mM potassium phosphate, 100 mM NaCl, and 20 mM imidazole, pH 8.0 (Buffer A), then supplemented with 100 μM PLP, 0.02 mg/mL DNase I, and BugBuster® at $\frac{1}{10}^{th}$ the manufacturer's recommendation. Cell lysis proceeded at 37° C. for 1 hour, at which point the lysate was heat treated at 75° C. for 1 hour. The lysate was clarified by centrifugation for 15 minutes at 15000 g, and the supernatant was collected. The lysate was then run over a column prepared with 2.5 mL Ni-NTA Agarose (Qiagen) pre-equilibrated with Buffer A. The bound protein was then washed with 10 column volumes (CVs) of Buffer A, and protein was eluted with 50% Buffer A and 50% 25 mM potassium phosphate, 100 mM NaCl, and 500 mM imidazole, pH 8.0 (Buffer B) and collected. An additional 1 mM PLP was added to the collected protein solution ensure full cofactor incorporation and then buffer exchanged into 50 mM potassium phosphate, pH 8.0 (KPi) by dialysis. The purified protein was then flash frozen in 20 μL aliquots in liquid nitrogen and stored at −80° C. Protein concentrations were determined using the Pierce™ BCA Protein Assay Kit (ThermoFisher) according to the manufacturer's recommendations.

Alternatively, protein catalyst could be prepared as a heat-treated lysate and used directly for preparative-scale reactions. In these instances, thawed cell pellets were resuspended in a volume of KPi containing 100 μM PLP that was appropriate for the given reaction, usually 50-100 mL. The dilute resuspension was then heat treated at 75° C. for >1 hour to efficiently lyse the cells and denature the E. coli proteins, and then clarified by centrifugation at 14000 g for 15 minutes. (Note that more concentrated resuspensions result in lower efficiency lysis by heat treatment alone, and should be supplemented with lysozyme or BugBuster® performed similarly to the lysis stages for purifying protein, withholding the further chromatography and buffer exchange steps.) This results in highly pure TyrS lysate by qualitative sodium dodecyl sulfate-polyacrylamide gel electrophoresis (SDS-PAGE).

For plate-based expression, single colonies of a desired variant or library were transferred into the wells of a 96-well plate containing 300 μL $LB_{carb}$. The cultures were covered with a sterile, breathable film and grown to stationary phase at 37° C. and 220 rpm. From these plates, 20 μL of each culture was transferred to new 96-well plates containing 630 μL of $TB_{carb}$ and grown for 6 hours at 37° C. and 220 rpm. Protein expression was induced with the addition of 50 μL of 14 mM IPTG in $TB_{carb}$ for a final concentration of 1 mM IPTG in a total volume of 700 μL of $TB_{carb}$. Expression proceeded for 24 hours at which point cells were harvested by centrifugation at 4500 g for 10 minutes, discarding the supernatant, and, unless preparing lysate immediately, covered with a non-breathable film and frozen at −20° C. until needed. Heat-treated lysate was prepared by resuspending thawed cells in 300 μL of KPi with 100 μM PLP, heat treating for 1.5 hours at 75° C., and clarifying by centrifugation at 4500 g for 10 minutes.

Example 3: Error-prone PCR Mutagenesis

Error-prone PCR (epPCR) was performed by a modified Taq PCR to amplify the gene between the NdeI and XhoI restriction sites using the primers of Table 2 and the thermal cycles of Table 3:

TABLE 2

PCR primers

| Name | Direction | Sequence |
|---|---|---|
| NdeI_f | Forward | GAAATAATTTTGTTTAACTTTAAGAAGGAGATATACATATG |
| XhoI_r | Reverse | GCCGGATCTCAGTGGTGGTGGTGGTGGTGCTCGAG |

TABLE 3

PCR thermal cycles

| Step | Temperature (° C.) | Time |
|---|---|---|
| 1 | 95 | 5 min |
| 2 | 95 | 30 s |
| 3 | 55 | 30 s |
| 4 | 72 | 90 s |
| 5 | Return to 2, 29 x | |
| 6 | 72 | 5 min |
| 7 | 10 | Hold |

Different concentrations of $MnCl_2$ (typically 200, 300, and 400 µM) were added to increase the error rate of the polymerase, resulting in libraries with different error rates. The PCR products were treated with DpnI at 37° C. for 1 hour and then isolated via gel extraction, assembled into the pET22b (+) plasmid vector via GIBSON ASSEMBLY® (1) (Synthetic Genomics, Inc., La Jolla, CA), and used to transform chemically competent E. coli as described above.

To determine which library to screen in more depth, a single plate (88 variants) was screened, looking for which gave the best balance of retention of enzyme function and sufficient genetic diversity. Once selected, additional variants of this library were screened until one or more variants were identified with improved activity, which were then used directly in a subsequent round of mutagenesis and screening or recombined (see below) to identify additive mutations.

Example 4: Site-Saturation Mutagenesis

Site-saturation mutagenesis (SSM) was performed via the "22-codon trick" with a few modifications. Briefly, a forward primer template was designed at the selected site comprising three parts: an assembly region, the mutated site, and an annealing region. The assembly region was located immediately upstream of the mutated site with a $T_m$ of ~55° C. The annealing region was located immediately downstream of the mutated site with a $T_m$ of ~68° C., preferably ending on one or more G or C bases. From this template, three primers were obtained with the codons NDT, VHG, and TGG in place of the native codon at the mutated site, comprising 22 codons that cover all 20 amino acids with leucine and valine sampled twice. A reverse primer was designed completely overlapping the assembly region of the forward primer (immediately adjacent to the mutated site) and extending to a final $T_m$ of ~68° C., again ending on one or more G or C bases. The secondary structures were examined to ensure that no strong monomeric or dimeric primer-primer interactions would interfere with the primer-template interactions and adjusted as necessary. Once ordered, the primers were used in a QuikChange™-like PCR (Agilent Technologies, Inc., Santa Clara, CA) using Phusion® polymerase (New England Biolabs, Ipswich, MA), isolated via gel extraction, and assembled via GIBSON ASSEMBLY® (Synthetic Genomics, Inc., La Jolla, CA). Xia et al., New insights into the QuikChange™ process guide the use of Phusion DNA polymerase for site-directed mutagenesis. *Nucleic Acids Res.* 43, e12 (2015). Alternatively, to reduce the chances for non-specifically assembled constructs, two fragments were generated with the SSM primers, splitting the plasmid template at the resistance cassette (ampicillin (AmpR) in pET22b (+), as used here) using the primers of Table 4:

TABLE 4

Primers used to generate the SSM primers

| Name | Site | Direction | Sequence |
|---|---|---|---|
| AmpR_AmpR_f | | Forward | CCAACTTACTTCTGACAACGATCGGAGGACCGAAGGAGCTAACCGCTTTTTTGC |
| AmpR_AmpR_r | | Reverse | CGATCGTTGTCAGAAGTAAGTTGGCCGCAGTGTTATCACTCATGGTTATGGCAG |

The forward SSM primer were paired with the reverse AmpR primer and the reverse SSM primer were paired with the forward AmpR primer in pET22b (+). The fragments were generated via PCR with PHUSION polymerase (New England Biolabs, Ipswich, MA) and purified by gel extraction, then assembled again via GIBSON ASSEMBLY® (Synthetic Genomics, Inc., La Jolla, CA). Once assembled, the DNA was used for transformation and plate-based expression. For each site targeted, a single plate (88 variants, providing 4-fold oversampling of the 22 codons and a 95% chance of complete library coverage in a unbiased library) was screened (see below) and the identity of improved variants were confirmed by Sanger sequencing. Kille, et al., Reducing codon redundancy and screening effort of combinatorial protein libraries created by saturation mutagenesis. *ACS Synth. Biol.* 2, 83-92 (2013).

Example 5: Recombination Via Staggered Extension Process

When improved variants were identified containing mutations at different sites, recombination via a modification of the Staggered Extension Process (StEP) PCR was performed. H. Zhao, et al., Molecular evolution by staggered extension process (StEP) in vitro recombination. *Nat. Biotechnol.* 16, 258-261 (1998). In all cases, >250 ng of total plasmid DNA (usually 500 ng) was used per 20 µL PCR, with a final concentration of 50 nM forward and reverse primers flanking the gene for amplification using 10× Standard Taq Buffer. For a large number of variants (>20), cultures were grown to saturation in $LB_{carb}$ and combined in equal volumes before isolating all plasmid DNA simultaneously. For a lower number of variants, plasmid DNA was isolated individually and then normalized. To recombine the variant genes, six identical reactions were created and placed along a temperature gradient in an EPPENDORF® MAS- TERCYCLER® X50 (96-well silver block) (Eppendorf AG, Hamburg, Germany) and run on the following thermal cycle:

| Step | Temperature (° C.) | Time |
|---|---|---|
| 1 | 95 | 20 s |
| 2 | 95 | 5 s |
| 3 | 55 | 2 s |
| 4 | Gradient, 50-72 | 2 s |
| 5 | Return to 2, 120 x | |
| 6 | 68 | 5 min |
| 7 | 4 | Hold |

The template plasmid was digested with the addition of 1 µL DpnI at 37° C. for at least 1 hour and analyzed by gel electrophoresis. The reaction with the lowest temperature along the gradient that gave a discrete PCR product (usually, but not always, 50° C.) was then used for a subsequent amplification PCR with PHUSION® polymerase (New England Biolabs, Ipswich, MA). The PCR product containing recombined variants was isolated by gel extraction, assembled into pET22b (+), and used for expression as described above for error-prone PCR mutagenesis, then screened as described below to identify variants with improved activity.

Example 6: Absorbance-based Screening

Enzyme variants were tested for activity by combining heat-treated lysate (prepared as described above) with Ser and an appropriate nucleophile (e.g., indole or a phenol analog), along with 5% EtOH by volume as cosolvent, directly into a UV-transparent assay plate and measuring the change in absorbance over time at a given wavelength that has been validated to increase over the course of the reaction. For example, the absorbance of 1-naphthol increases as it is converted to the ncAA product at wavelengths between 284 nm and ~350 nm (FIG. 1A and FIG. 1B). For reactions containing 5 mM 1-naphthol, the change in absorbance at 335 nm can be observed to increase over the course of the reaction and is directly proportional to product formation. Changes in activity can be quantified by looking at differences in absorbance at a given timepoint in the linear range of the reaction (steady state) if the reaction is continuously monitored, or at the endpoint if it occurs before steady state ends. For continuously monitored reactions, it is also possible to determine the rate of each variant and use this to determine the change in activity.

Example 7: LCMS Screening

Enzyme variants could also be tested for activity via LCMS when conditions could not be optimized for absorbance-based screening, such as for low levels activity or poorly absorbing nucleophiles. In this case, heat-treated lysate was combined with Ser and the phenol analog, along with 5% EtOH by volume as cosolvent, and allowed to react overnight (typically ~18 hours) at 37° C. The reactions were worked up with 300 µL of 1:1 acetonitrile (MeCN)/1 M aq. HCl and then filtered through a 0.2 µm 96-well filter plate (Pall AcroPrep™ #8019, Pall Corp., Port Washington, New York) via centrifugation at 5000 g until the soluble reaction components were collected in the wells of a 96-well LCMS assay plate. This plate was then sealed and run on a suitable LCMS method and column that can separate reaction components sufficiently for quantification by UV and/or MS. For screening for activity with 2-chlorophenol, a C18 guard column used as the stationary phase was sufficient to provide this separation over a 1-minute method, resulting in reasonable throughput for screening ~1000 variants per day.

Example 8: Analytical-Scale Vial Reactions

Analytical reactions were performed in 2-mL glass vials in a total reaction volume of 200 µL. Vials were first charged with 10 µL of 20x stock of the nucleophile in EtOH (final concentration of 5% EtOH by volume), to which 190 µL of a mixture of Ser and purified enzyme in KPi were added. The reactions were generally protected from light (primarily 1-naphthol, which is a photoacid) and allowed to react at 37° C. At the end of the reaction time, the 200-µL reactions were worked up with 800 µL of 1:1 1 M aq. HCl/MeCN, transferred to a microcentrifuge tube, and clarified by centrifugation at 14000 g. A 200-µL aliquot of this mixture was then collected and analyzed via LCMS as described in the general experimental methods.

Example 9: Analytical-Scale Plate Reactions

Analytical reactions were also carried out in plates using a specified volume of heat-treated lysate in place of a known final concentration of purified enzyme. Because screening used heat-treated lysate where the concentration of enzyme was not known or measured, improvements in expression, stability, or other factors were allowed to manifest as improvements in the catalyst. These reactions were performed identically to the vial reaction specified above, without controlling for enzyme concentration. At the end of the reaction time, the 200-µL reactions were worked up with either 300 or 800 µL of 1:1 1 M aq. HCl/MeCN (depending on the expected yield of the reaction) and then filtered through a 0.2 µm 96-well filter plate (Pall AcroPrep™ #8019, Pall Corp., Port Washington, New York) via centrifugation at 5,000 g until the soluble reaction components are collected in the wells of a 96-well LCMS assay plate. This plate was sealed and analyzed via LCMS as described in the general experimental methods.

Examples 10: Preparative-Scale Reactions

Preparation of Tyr analogs for characterization and further experiments was performed using either purified enzyme or a large volume of heat-treated lysate. First, a 1.1 molar equivalent of Ser was weighed into a flask followed by the phenol analog as the limiting reagent. The phenol analog was dissolved in EtOH (5% by volume final concentration), which was then mixed with an appropriate amount of KPi for the reaction volume. Solutions were incubated at the reaction temperature (typically 37° C.) in a water bath, followed by the addition of enzyme, reaching the desired final concentrations of all reaction components. The reactions were protected from light and allowed to react for up to three days, taking small samples as timepoints for reaction progress analysis by LCMS. Reactions were then concentrated in vacuo and the Tyr analog products isolated by reversed-phase chromatography. Collected fractions containing the Tyr analogs were pooled and again concentrated in vacuo to afford the final product.

Example 11: Michaelis-Menten Kinetics

Enzyme kinetic parameters ($k_{cat}$ and $K_M$) for the conversion of 1-naphthol to NaphAla by SEQ ID NO: 6 were inferred from initial rate measurements of a continuous colorimetric screen (FIG. 1). Briefly, a reaction containing 400 μM 1-naphthol and 10 μM 1-naphthol was monitored for 40 minutes, scanning infrequently (once every 2 minutes) to reduce photo-induced oxidation of 1-naphthol (FIG. 1A). An exponential function was used to model the reaction time course at 335 nm (FIG. 1B), and these parameters were used to obtain the total absorptivity change (AA) for the conversion of 400 μM 1-naphthol to 400 μM NaphAla (FIG. 1C). This in turn can be used to determine the molar absorptivity change at 335 nm (AΣ335) for the conversion of 1-naphthol to NaphAla at pH 8.0.

Using this conversion ratio, short time courses (0.2 sec intervals for 300 seconds) could be obtained at varying concentrations of 1-naphthol (400-5000 μM) and 20 mM Ser (FIG. 1D) that correspond to rates of NaphAla formation. Correcting for enzyme concentration and modeling these rates to the Michaelis-Menten equation of enzyme kinetics provided estimations of $k_{cat}$ and $K_M$ (FIG. 1E).

Example 12: Determination of Enantiopurity

Enantiopurity was assessed using Na-(5-fluoro-2,4-dinitrophenyl)-L-alaninamide (Marfey's reagent), a common chiral derivatization agent. Bhushan et al., Use of Marfey's reagent and analogs for chiral amino acid analysis: Assessment and applications to natural products and biological systems. *J. Chromatogr. B Analyt. Technol. Biomed. Life Sci.* 879, 3148-3161 (2011). To assess the enantiopurity of an enzymatic reaction without purification, a small-scale analytical reaction was first carried out as described above. After the reaction time, 100 μL of 1 M aq. NaHCO₃ were added. Alternatively, for purified product, a ~10 mM solution in KPi was prepared which was then mixed 2:1 with 1 M aq. NaHCO₃. From these solutions, 125 μL were transferred into a new 2-mL vial along with 33 μL of a 33 mM solution of Marfey's reagent in acetone. This mixture was incubated at 37° C. and 220 rpm for 2 hours, and then the mixture was diluted with 600 μL 1:1 1 M aq HCl/MeCN.

The products of the reaction were analyzed by LCMS using the following gradient of MeCN: 25-45% over 7 minutes. Products were monitored by MS in single-ion mode selected for the expected molecular ion of the $S_NAr$ product (e.g., 434 m/z for the Tyr product). The absorbance spectra of most substrates change only slightly upon alkylation, allowing reasonably accurate estimations of conversion by using the substrate and product HPLC peak areas as a proxy for relative substrate and product concentrations. Summing the substrate and product peak areas results in minimal difference across all reactions, even when the reactions are high yielding. Possible exceptions are 3-OH (3-hydroxyphenol) and 2-I (2-iodophenol), which result in an increase and decrease in total area with higher product formation, respectively. This provided baseline separation of DL-tyrosine peaks (FIG. 2). Only one of these peaks (with the shorter retention time) was seen for L-tyrosine, along with the enzymatic product of SEQ ID NO: 10 and phenol (FIG. 2). Putative O-alkylation product of the tyrosine and Marfey's reagent, with the same mass as the desired N-alkylation product, was seen as an early single peak. A similar O-alkylation product of unreacted phenol and Marfey's reagent was also seen in enzymatic reactions with leftover phenolic substrate. In all cases, enzymatic products derivatized with Marfey's reagent were identified to have only a single peak.

To confirm enantiopurity in the absence of accessible D) enantiomers of these compounds, the D) enantiomer of Marfey's reagent was used to prepare a racemic mixture of this reagent. Enzymatic Tyr products were derivatized with racemic and enantiopure Marfey's reagent mixtures which resulted in two or one peaks, respectively, and confirmed the L configuration as the only observable enzymatic product.

Example 13: Measuring Kinetic Isotope Effects

Kinetic isotope effects (KIEs) were measured from reactions as described in Example 8 with a few minor changes. The cosolvent used was DMSO rather than EtOH for long-term storage. KIEs were measured in direct competition with equimolar concentrations of the standard and deuterated substrate at a total concentration of 5 mM phenolic substrate and 50 mM Ser. Reactions were analyzed by LCMS, extracting the ions corresponding to the appropriate product masses and comparing their ratios. Ser KIEs were measured with Ser-d₃ using 2-chlorophenol as the phenolic substrate. (Note: the +2 isotope of chlorine yielded a 30% relative abundance of a 218 m/z product for 3-chloro-Tyr, which also corresponded with the di-deuterated product of Ser-d₃ and 2-chlorophenol. Ratios of 216/218 ion counts were therefore not exactly the 3-chloro-Tyr 216 m/z ion over the deuterated 3-chloro-Tyr 218 m/z ion, which would give a value of slightly lower than 1 for a true KIE of 1.)

Example 14: Preparation of Lyophilized Enzyme Catalyst for Large-Scale Reactions Heat-treated lysate was prepared as in Example 2. For the large-scale reactions reported, dialysis of the lysate into KPi was performed to remove small-molecule impurities from the *E. coli* host cell. However, in many instances this step was not explicitly needed, as these impurities were removed during the washing steps when isolating the ncAA product (see below). Once prepared, the lysate was transferred into a tared 50-mL Falcon® conical tube (Corning Inc., Corning, NY) and flash-frozen in liquid nitrogen while agitating. Once completely frozen, the tube was topped with a Kimtech Science™ Kimwipe™ (Kimberly-Clark, Irving, Texas) and lyophilized to dryness, resulting in a benchtop-stable powder. The mass of the powder was recorded (typically ~1 gram).

To quantify the activity of the powder, a small portion was removed and resuspended to a final concentration of 2 mg/mL in deionized water. The rate of conversion (mM/mg) of the desired substrate at concentrations similar to those to be used for the large-scale reactions was obtained at 1, 0.5, and 0.25 mg/mL powder. The expected amount of product produced per gram of powder was determined, and reaction conditions were scaled accordingly. The specific activities in these analytical reactions were uniformly comparable to the large-scale reactions.

Example 15: Multi-Gram-Scale Synthesis of NaphAla

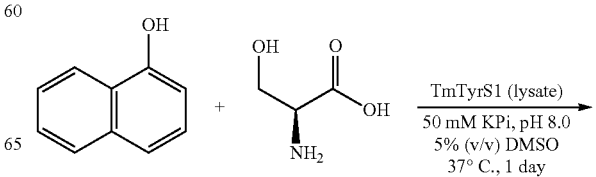

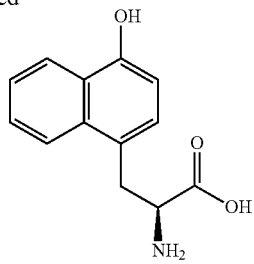

Figure 3A:
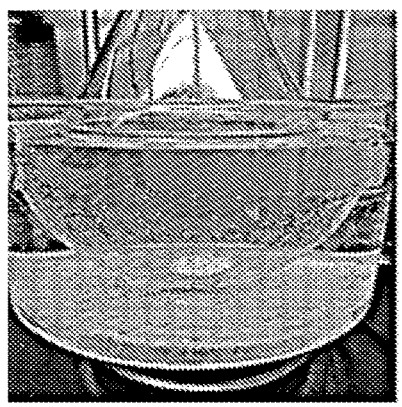
FIG. 3A is a picture of the solution of TmTyrS1 (SEQ ID NO: 6) and Ser in KPi, prior to the addition of 1-naphthol.
Figure 3B:
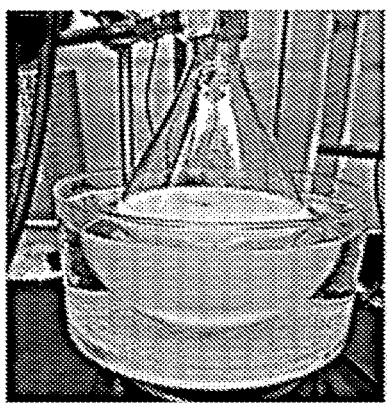
FIG. 3B is a picture of the reaction after 1 day of continuous 1-naphthol addition, at which point the NaphAla product has crashed out of solution.
Figure 3C:
FIG. 3C is a picture of the isolated product after filtration. The product was washed with ice-cold water and ethyl acetate, then dried.

In an oven-dried 1-L 1-N round-bottom flask (RBF) equipped with a magnetic stir bar, Ser (8.02 g, 76.3 mmol) was dissolved in 510 mL of KPi (50 mM, pH=8.0) and 30 mL of DMSO. The solution was sparged with argon for 30 minutes and a balloon of argon was placed over the reaction mixture. In a separate 50-mL Falcon® conical tube, lysate derived from SEQ ID NO: 6 (1.2 g powder from 1 L culture, which had a previously quantified activity per mg of powder) was gently dissolved in 60.0 mL of deionized water and added to the reaction while stirring. During addition, a liquid funnel was used as an argon dispersion funnel and the lysate solution was added by pouring directly into the flask. The RBF was then dropped into a pre-warmed water bath at 37° C. and allowed to stir at 500 rpm, starting as a clear yellow-green solution (FIG. 3A). Meanwhile, 1-naphthol (5.00 g, 34.7 mmol) was dissolved in 45.0 mL of DMSO (resulting in a 50.0 mL solution) and added dropwise to the reaction mixture using a syringe pump (rate=2 mL/hour). Following the addition of ~46.3 mL (~23 hours of dropwise addition) of the 1-naphthol solution, a white solid had crashed out of the solution (FIG. 3B and FIG. 4C). The reaction mixture was then filtered through filter paper using a Buchner funnel (FIG. 3C) and washed with 500 mL of cold, deionized water followed by 500 mL of EtOAc. A white solid was collected from the filter pad, transferred to a 125-mL RBF, and dried under reduced pressure (on high vacuum) for 48 hours with mild heating (40° C.) to yield 5.5 g (74% yield) of NaphAla as a white solid (>99% HPLC purity over 1-naphthol).

An aliquot for $^1$H NMR spectroscopy was prepared by dissolving ~5 mg of NaphAla in ~600 μL of $D_2O$ and adding 3-5 drops of DCl. To obtain an aliquot for $^{13}$C NMR spectroscopy, 6 mg of NaphAla were stirred in an ethereal solution of HCl (0.5 mL, 4 M in $Et_2O$) for 30 minutes. The $Et_2O$ was subsequently removed under reduced pressure and the resultant white solid was dissolved in 600 μL of $D_2O$ for NMR analysis.

$^1$H NMR (400 MHZ, $D_2O$) δ 8.07 (dd, J=8.8, 1.4 Hz, 1H), 7.88-7.81 (m, 1H), 7.50 (ddd, J=8.5, 6.8, 1.5 Hz, 1H), 7.44 (ddd, J=8.2, 6.8, 1.2 Hz, 1H), 7.13 (d, J=7.8 Hz, 1H), 6.76 (d, J=7.8 Hz, 1H), 4.24 (dd, J=9.1, 5.7 Hz, 1H), 3.64 (dd, J=14.8, 5.7 Hz, 1H), 3.26 (dd, J=14.9, 9.2 Hz, 1H).

$^{13}$C NMR (101 MHZ, $D_2O$) δ 172.00, 151.78, 132.25, 128.78, 127.33, 125.59, 124.96, 123.06, 122.45, 121.88, 108.22, 53.70, 32.96.

HRMS (FD+) Calculated for $C_{13}H_{13}NO_3$ (M+): 231.08954; Found: 231.08980.

Determination of Enantiopurity by Chemical Derivatization with Marfey's Reagent.

Enantiopurity was determined by derivatization with enantiopure (L) and racemic Marfey's reagent. Specifically, in a 1.5-mL Eppendorf tube, NaphAla (0.5 μmol) was dissolved in 1 M aq. $NaHCO_3$ (100 μL), to which 10 μL of a 33-mM solution of Marfey's reagent in acetone (0.33 μmol) were added. The vial was shaken for 2 hours at 500 rpm, 37° C. The reaction was allowed to cool to room temperature, then diluted with 1:1 1 M aq. HCl/MeCN (600 μL). The solution was analyzed via LCMS (25% to 45% MeCN, monitored by using single-ion mode for the molecular ion of the $S_NAr$ product of 483 m/z). Absolute stereochemistry for NaphAla was inferred by analogy to L-tyrosine and determined to have >99.5% enantiomeric excess. Determination of Chemical Purity Using Quantitative $^1$H NMR Spectroscopy.

NaphAla (4.82 mg, 20.85 μmol) and dimethyl sulfone (1.63 mg, 17.32 μmol) were weighed into a 2-mL Eppendorf tube and dissolved in 1.5 mL of $D_2O$ and 200 μL of DCl. An aliquot was removed and a $^1$H NMR was obtained with a relaxation delay of 30 s. The chemical purity was determined to be 93% (relevant portion of $^1$H NMR shown below). This procedure was performed in duplicate, and the reported chemical purity (91%) is an average of duplicate procedures. Not intending to be bound by theory, weight impurities may include water and/or salts from the buffer/lysate. NaphAla was determined to be >99% pure of UV-absorbing chemical species (e.g., 1-naphthol) by HPLC analysis.

Example 16: Gram-Scale Synthesis of 3-Methyl-Tyr

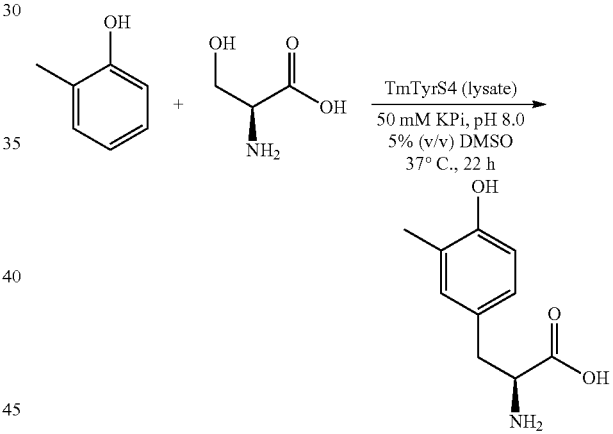

Figure 5A:
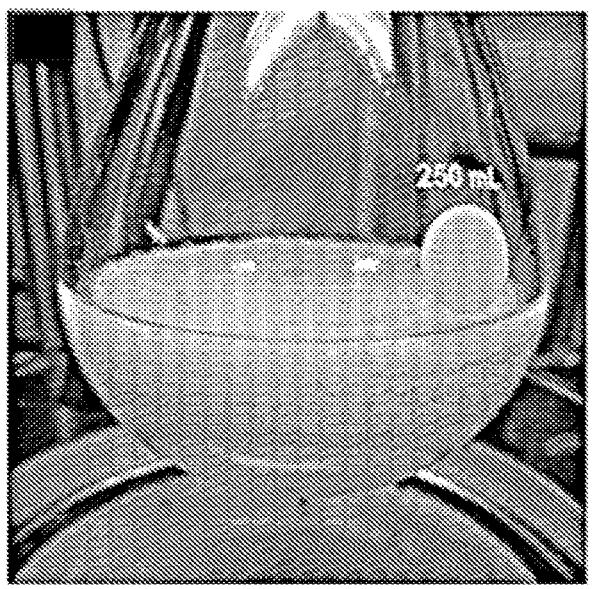
FIG. 5A shows the product crashing out of solution after a second addition of 50 mM 2-methylphenol and 10 hours.
Figure 5B:
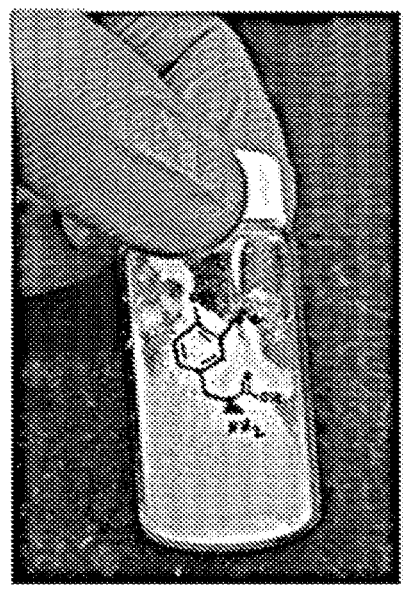
FIG. 5B is a picture of 1.13 g of the pure isolated product (3-methyl-Tyr).

To an oven-dried 250-mL 1-N RBF equipped with a magnetic stir bar, Ser (2.08 g, 19.8 mmol) was added. Subsequently, o-cresol (2-methylphenol, 0.659 g, 6.00 mmol, solution in 6.00 mL DMSO) was added, followed by 100 mL of KPi (50 mM, pH=8.0). The RBF was then dropped into a pre-warmed oil bath at 37° C. In a separate 50-mL Falcon® conical tube, lysate derived from SEQ ID NO: 9 (1.2 g powder from a 1-L culture, which had a previously quantified activity per mg of powder) was gently dissolved in 14.0 mL of deionized water and added to the reaction mixture using a Pasteur pipette. The reaction mixture was allowed to stir at 37° C. After a 12-hour reaction time, an aliquot was removed and analyzed by LCMS, which indicated ~90% conversion to 3-methyl-Tyr relative to o-cresol. A second batch of o-cresol (0.6456 g, 5.878 mmol, solution in 6.00 mL DMSO) was then added and the reaction was allowed to continue stirring at 37° C. After approximately 10 hours, a white solid crashed out of solution (FIG. 5A). The reaction mixture was filtered through filter paper using a Buchner funnel and washed with 75.0 mL of cold, deionized water followed by 75.0 mL of EtOAc. A white solid was collected from the filter pad, transferred to a 20-mL scintillation vial, and dried under reduced pressure (on high vacuum) for 24 hours with mild heating (40° C.) to yield 1.13 g (48.7% yield) of 3-methyl-Tyr as a white solid (FIG. 5B) with >99% HPLC purity over o-cresol.

An aliquot for $^1$H NMR spectroscopy was prepared by dissolving ~5 mg of 3-Me-Tyr in ~600 µL of $D_2O$ and adding 3-5 drops of DCl. To obtain an aliquot for $^{13}$C NMR spectroscopy, 6 mg of 3-Me-Tyr were stirred in an ethereal solution of HCl (0.5 mL, 4 M in $Et_2O$) for 30 minutes. The $Et_2O$ was subsequently removed under reduced pressure and the resultant white solid was dissolved in 600 µL of $D_2O$ for NMR analysis.

$^1$H NMR (400 MHZ, $D_2O$) δ 6.97-6.92 (m, 1H), 6.87 (dd, J=8.2, 2.4 Hz, 1H), 6.71 (d, J=8.1 Hz, 1H), 4.17 (dd, J=7.5, 5.6 Hz, 1H), 3.10 (dd, J=14.7, 5.6 Hz, 1H), 2.98 (dd, J=14.7, 7.5 Hz, 1H), 2.03 (s, 3H).

$^{13}$C NMR (101 MHZ, $D_2O$) δ 171.78, 153.21, 131.99, 127.92, 125.78, 125.64, 115.49, 54.38, 34.79, 15.17.

HRMS (FD+) Calculated for $C_{10}H_{13}NO_3$ (M): 195.08954; Found: 195.08901.

Determination of Enantiopurity by Chemical Derivatization with Marfey's Reagent.

Enantiopurity was determined by derivatization with enantiopure (L) and racemic Marfey's reagent. Specifically, in a 1.5 mL Eppendorf tube, 3-Me-Tyr (0.5 µmol) was dissolved in 1 M aq. $NaHCO_3$ (100 µL), to which 10 µL of a 33-mM solution of Marfey's reagent in acetone (0.33 µmol) was added. The vial was shaken for 2 hours at 500 rpm, 37° C. The reaction was allowed to cool to room temperature, then diluted with 1:1 1 M aq. HCl/MeCN (600 µL). The solution was analyzed via LCMS (25% to 45% MeCN, monitored by using single-ion mode for the molecular ion of the $S_NAr$ product of 447 m/z). Absolute stereochemistry for 3-Me-Tyr was inferred by analogy to L-tyrosine and determined to have >99.5% enantiomeric excess.

Determination of Chemical Purity Using Quantitative $^1$H NMR Spectroscopy.

3-Me-Tyr (4.31 mg, 22.09 µmol) and dimethyl sulfone (2.02 mg, 21.46 µmol) were weighed into a 2-mL Eppendorf tube and dissolved in 1.5 mL of $D_2O$ and 200 µL of DCl. An aliquot was removed and a $^1$H NMR was obtained with a relaxation delay of 30 s. The chemical purity was determined to be 92% (relevant portion of $^1$H NMR shown below). The dimethylsulfone peak overlapped with one of the benzylic protons; therefore, 1.0 was subtracted from the integration of the standard. This procedure was performed in duplicate, and the reported chemical purity (89%) is an average of duplicate procedures. Not intending to be bound by theory, the weight impurities may include water and/or salts from the buffer/lysate. 3-Me-Tyr is >99% pure of UV-absorbing chemical species (e.g., o-cresol) by HPLC analysis.

Example 17: Crystallization of SEQ ID NO: 6

For the crystallization of SEQ ID NO: 6, protein was purified as described above. For initial screening, protein was thawed from −80° C. to room temperature and diluted to 10 and 20 mg/mL in storage buffer (KPi). Using a Crystal Gryphon robot (Art Robbins Instruments, Sunnyvale, CA), sparse matrix screening was performed using the Wizard HT 1 & 2 (Rigaku, Tokyo, Japan), JCSG-plus™ (Molecular Dimensions (Anatrace Products LLC, Shefield, England)), Index and PEGRx (Hampton Research, Aliso Viejo, CA) crystallization screens in Intelli-Plate 96-2 drop crystallization plates (Art Robbins Instruments, Sunnyvale, CA) using 0.2 µL drops of precipitant followed by 0.2 µL of protein solution. Plates were sealed with transparent adhesive covers and incubated at room temperature. After 2 days, crystals were observed in well $C_3$ of the Wizard Screen (1.2 M $NaH_2PO_4$/0.8 M $K_2HPO_4$, 0.1 M N-cyclohexyl-3-aminopropanesulfonic acid (CAPS), 0.2 M $Li_2SO_4$), which served as the precipitant for all crystallization presented here.

These crystals were then optimized by drop ratio variation in 24-well CrysChem M Plates (Hampton Research, Aliso Viejo, CA) using 1-6 µL protein drops and 2-5 µL precipitant drops. Yellow crystals with an atypical morphology (FIG. 6) appeared in all wells after 1-3 days, with larger crystals generally observed at higher protein and lower precipitant concentrations.

Example 18: Crystal Soaking and Cryoprotection

For crystals of the SEQ ID NO: 6 holoenzyme, a cryoprotectant solution was prepared by mixing 80 µL of equilibrated reservoir solution with 20 µL of ethylene glycol. This solution was then added to the crystal drop, sequentially adding and removing equivalent volumes until no schlieren was observed.

To trap the amino-acrylate intermediate E(A-A) state of SEQ ID NO: 6, a solution was prepared that consisted of the precipitant supplemented with 100 mM Ser. This was serially added and removed from the crystallization drop in 2-µL aliquots until no schlieren was observed. Crystals were incubated for 30 minutes, during which they turned from yellow to colorless, indicating that the amino-acrylate had formed. At this point, the serine-containing precipitant was further supplemented with 20% ethylene glycol and used as a cryoprotectant as stated above.

To obtain structures containing 1-naphthol mimics 4-hydroxyquinoline (QOH) and quinoline N-oxide (QOX), the amino-acrylate-containing crystals were first prepared as stated above. The cryoprotectant solution (20% ethylene glycol) was then further supplemented with 20 mM QOH or QOX, then applied to the crystals. The only addition to the cryoprotection procedure described above is the incubation of crystals in the cryoprotectant for 2-10 minutes. Following cryoprotection, all crystals were mounted in nylon loops, cooled in liquid nitrogen, and stored in liquid nitrogen prior to data collection.

Example 19: Crystal Structure Determination

Diffraction data were collected at the Stanford Synchrotron Radiation Laboratory (SSRL) beamline 12-2. Data reduction and integration were carried out using XDS and scaled using Aimless in the CCP4 suite of programs. Kabsch, XDS. *Acta Crystallogr. D Biol. Crystallogr.* 66, 125-132 (2010); Winn et al., Overview of the CCP4 suite and current developments. *Acta Crystallogr. D Biol. Crystallogr.* 67, 235-242 (2011). For the structure of holo SEQ ID NO: 6, molecular replacement (MR) was performed using the structure of a holo TrpB from *Pyrococcus furiosus* (PfTrpB; PDB 5DVZ) as a search model in Phaser. Buller et al., Directed evolution of the tryptophan synthase β-subunit for stand-alone function recapitulates allosteric activation. *Proc. Natl. Acad. Sci. U.S.A.* 112, 14599-14604 (2015); McCoy et al., Phaser crystallographic software. *J. Appl. Crystallogr.* 40, 658-674 (2007). For all other structures, the protein chain of holo SEQ ID NO: 6 was used for MR. Model building and modification in the electron density was performed using Coot and structure refinement was performed using Phenix. Emsley et al., Features and development of Coot. *Acta Crystallogr. D Biol. Crystallogr.* 66, 486-501 (2010); Adams et al., PHENIX: A comprehensive Python-based system for macromolecular structure solution. *Acta Crystallogr. D Biol. Crystallogr.* 66, 213-221 (2010). Other ligands, specifically QOX and QOH, as well as water molecules and ethylene glycol were added during later stages of refinement. Occasionally, spurious electron density peaks were present in the active site, dimer interface, and COMM domain that could not be unambiguously modeled by alternative protein conformations, solvent, or other additives applied during the procedure, so these were left uninterpreted. The quality of the final models was evaluated with MolProbity and PROCHECK. Chen et al., MolProbity: All-atom structure validation for macromolecular crystallography. *Acta Crystallogr. D Biol. Crystallogr.* 66, 12-21 (2010); Laskowski et al., PROCHECK: a program to check the stereochemical quality of protein structures. *J. Appl. Crystallogr.* 26, 283-291 (1993). Data collection and refinement statistics are presented in Table 5.

TABLE 5

Data collection and refinement statistics for SEQ ID NO: 6 structures

| Structure | SEQ ID NO: 6-E($A_{in}$) | SEQ ID NO: 6-E(A-A) | SEQ ID NO: 6-E(A-A) + quinoline N-oxide | SEQ ID NO: 6-E(A-A) + 4-hydroxylquinoline |
|---|---|---|---|---|
| Unit cell | | | | |
| Space group | I4 | I4 | I4 | I4 |
| a, b, c (Å) | 164.6, 164.6, 83.1 | 164.6, 164.6, 84.3 | 164.4, 164.4, 84.3 | 164.9, 164.9, 84.06 |
| α, β, γ (°) | 90.0, 90.0, 90.0 | 90.0, 90.0, 90.0 | 90.0, 90.0, 90.0 | 90.0, 90.0, 90.0 |
| Data collection | | | | |
| Wavelength (Å) | 0.97946 | 0.97946 | 0.97946 | 0.97946 |
| Resolution (Å) | 39.15-2.05 | 45.97-1.90 | 38.74-1.70 | 38.86-2.00 |
| Total/unique no. of reflections | 949735/69702 | 1195353/88525 | 1659189/123166 | 1016930/75913 |
| $R_{merge}^{a,b}$ | 0.07 (2.09) | 0.16 (2.43) | 0.09 (1.99) | 0.11 (1.73) |
| $R_{p.i.m}^{a,c}$ | 0.03 (0.58) | 0.04 (0.67) | 0.02 (0.56) | 0.03 (0.48) |
| $CC_{1/2}^{a,d}$ | 1.00 (0.62) | 0.99 (0.58) | 1.00 (0.59) | 0.99 (0.69) |
| $I/\sigma(I)^{a}$ | 21.0 (1.5) | 12.0 (1.4) | 17.6 (1.5) | 15.9 (2.0) |
| Redundancy[a] | 13.6 (14.0) | 13.5 (14.0) | 13.5 (13.6) | 13.4 (13.8) |
| Completeness[a] (%) | 100 (100) | 100 (100) | 100 (100) | 99.8 (99.9) |
| Refinement | | | | |
| No. of reflections used in refinement/test set | 69678/3488 | 88500/4531 | 123151/12284 | 75899/7556 |
| $R_{work}^{a,e}$ | 0.216 (0.342) | 0.170 (0.256) | 0.167 (0.262) | 0.187 (0.260) |
| $R_{free}^{a,e}$ | 0.232 (0.363) | 0.192 (0.294) | 0.186 (0.300) | 0.219 (0.318) |
| No. of nonhydrogen atoms | | | | |
| protein | 5956 | 5924 | 6016 | 5802 |
| ligand | 24 | 68 | 82 | 66 |
| solvent | 221 | 270 | 321 | 172 |
| root-mean-square deviation from ideal geometry | | | | |
| bonds (Å) | 0.002 | 0.019 | 0.018 | 0.003 |
| angles (°) | 0.48 | 1.46 | 1.43 | 0.59 |
| Ramachandran plot[f] (%) | | | | |
| favored | 97.09 | 98.17 | 97.78 | 97.90 |
| allowed | 2.91 | 1.83 | 1.96 | 1.97 |
| disallowed | 0.00 | 0.00 | 0.26 | 0.13 |
| PDB accession code | 8EGY | 8EGZ | 8EH0 | 8EH1 |

[a] Values in parentheses refer to data in the highest shell.

[b] $R_{merge} = \Sigma_{hkl}\Sigma_i |I_{i,hkl} - \langle I \rangle_{hkl}|/\Sigma_{hkl}\Sigma_i I_{i,hkl}$, where $\langle I \rangle_{hkl}$ is the average intensity calculated for reflection hkl from replicate measurements.

[c] $R_{p.i.m.} = (\Sigma_{hkl}(1/(N-1))^{1/2}\Sigma_i |I_{i,hkl} - \langle I \rangle_{hkl}|)/\Sigma_{hkl}\Sigma_i I_{i,hkl}$, where $\langle I \rangle_{hkl}$ is the average intensity calculated for reflection hkl from replicate measurements and N is the number of reflections.

[d] Pearson correlation coefficient between random half-datasets.

[e] $R_{work} = \Sigma ||F_o| - |F_c||/\Sigma |F_o|$ for reflections contained in the working set. $|F_o|$ and $|F_c|$ are the observed and calculated structure factor amplitudes, respectively. $R_{free}$ is calculated using the same expression for reflections contained in the test set held aside during refinement.

[f] Calculated with PROCHECK.

Example 20: Determination of Limit for Detectable Turnover Frequency

The activity of SEQ ID NO: 3 for Tyr formation was sufficiently low that it could not be reliably quantified. As other phenol analogs reacted at lower but more reliable levels, it became important to assign a limit of detection for Tyr to understand the rate enhancement achieved by directed evolution, specifically the E105G mutation.

Figure 7:
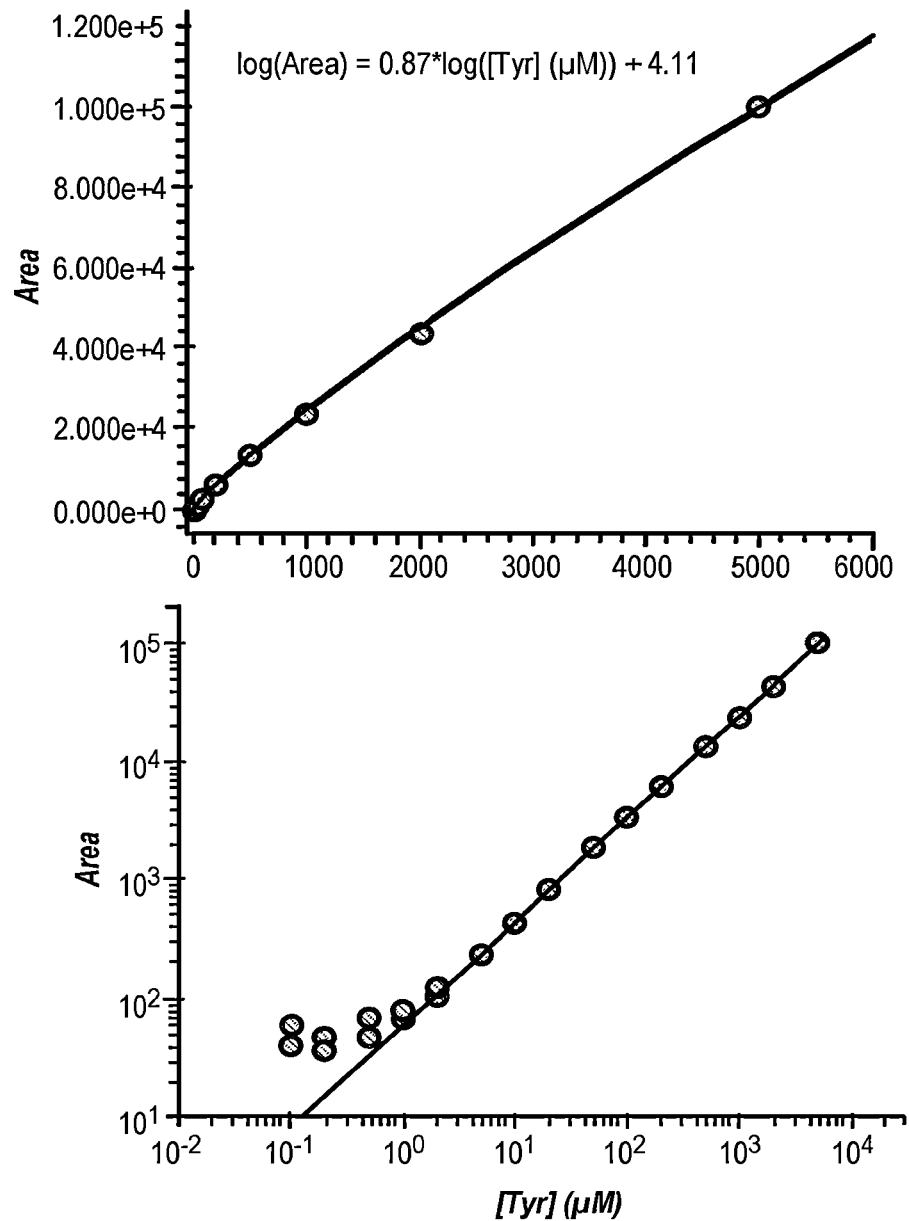
FIG. 7 are graphs representing a calibration curve and analytical detection limit of Tyr. Solutions of Tyr at known concentration were analyzed in duplicate and the MS peaks were integrated. Upper: The concentrations can be related to the peak area by a logarithmic relationship. Lower: The peak areas deviate from the logarithmic relationship below 1 µM Tyr, at which point instrument noise and residual Tyr from non-exhaustive column washing makes quantification impossible and presents a limit of detection.

A series of Tyr solutions in KPi ranging from 5 mM to 100 nM were prepared. These were combined 1:4 with 1:1 1 M aq. HCl/MeCN in the same way as analytical vial reactions and analyzed by LCMS. These data are presented in FIG. 7, showing the integrated peak area for Tyr vs. the known concentration of Tyr from the original solution. On a log-log plot, these data are linear above 1 µM, below which there is a basal level of peak that can be integrated. This likely arises from cross-contamination between samples, with Tyr not being completely washed off the column in all cases. Exhaustive washing failed to provide significant improvements, and thus 1 µM was designated as the lower limit of Tyr detectability.

Given this limit, and the maximum concentration of enzyme used in the reactions (100 µM), the minimum enzymatic turnovers required to detect Tyr is:

$$\frac{1 \ \mu M \ Tyr}{100 \ \mu M \ \text{enzyme}} = 0.01 \ \text{turnovers}$$

Reactions were carried out for exactly 24 hours, resulting in a turnover frequency (TOF, $h^{-1}$) of:

$$\frac{0.01 \ \text{turnovers}}{24 \ \text{hours}} = 0.00042 \ h^{-1}$$

Figure 8A:
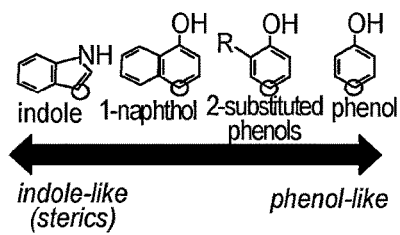
FIG. 8A is a representation of the proposed evolutionary 'substrate walk' from the native substrate of TrpB, indole, to phenol.
Figure 8B:
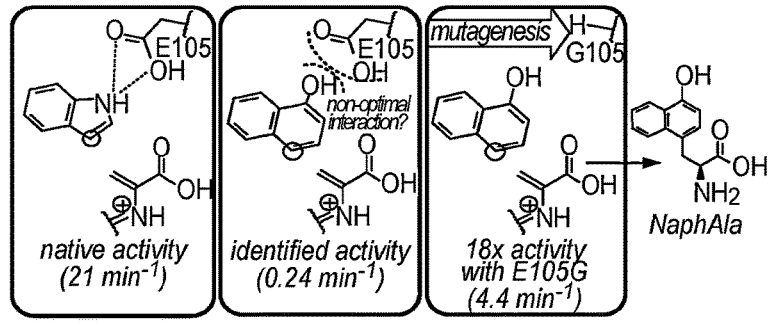
FIG. 8B is a schematic of how the universally conserved catalytic glutamate (E105) side chain participates in interactions important for $C_3$-alkylation of indole, which may not be optimal for para-alkylation of 1-naphthol. The schematic summarizes data showing that mutating the catalytic glutamate to glycine (E105G) enhanced activity 18-fold. The reaction exclusively forms the para-alkylation product β-(1-naphthol-4-yl)-L-alanine (NaphAla).
Figure 8C:
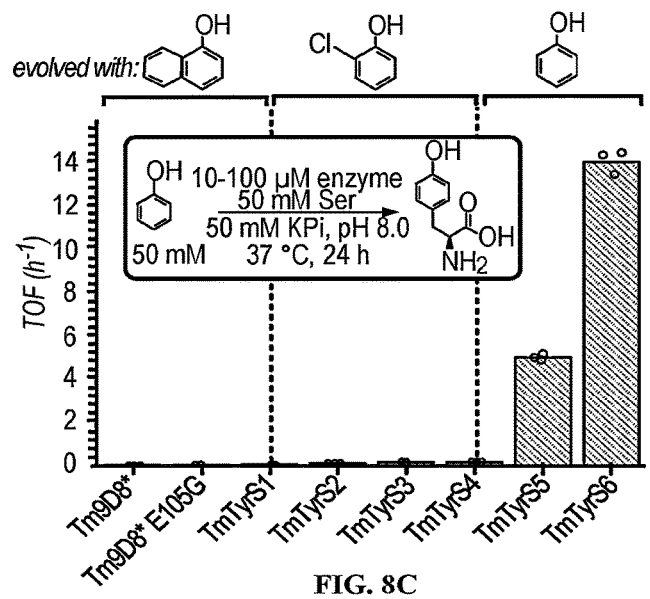
FIG. 8C is a graph showing the approximate turnover frequencies (TOFs, $h^{-1}$) for conversion of 50 mM phenol to Tyr by TyrS lineage. The screening substrate used during evolution is shown above the chart, with substrate change demarcated by vertical dashed lines.
Figure 8D:
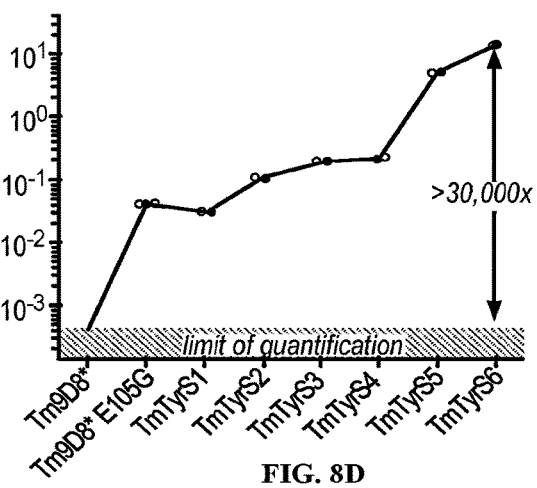
FIG. 8D is a graph showing the TOFs presented on a log scale with a quantified limit for the turnover frequency required to detect Tyr under the presented experimental conditions.

This limit is represented in FIG. 8D. As 100 µM SEQ ID NO: 3 did not exceed 1 µM Tyr in 24 hours this value provides a confident upper bound on its activity. TmTyrS6 reacts at a TOF of 14 $h^{-1}$, this results in a difference of:

$$\frac{14 \ h^{-1}}{0.00042 \ h^{-1}} = 33,300 \times \text{difference.}$$

Example 21: Estimating Product Formation by HPLC Peak Area Percentages

Figure 4A:
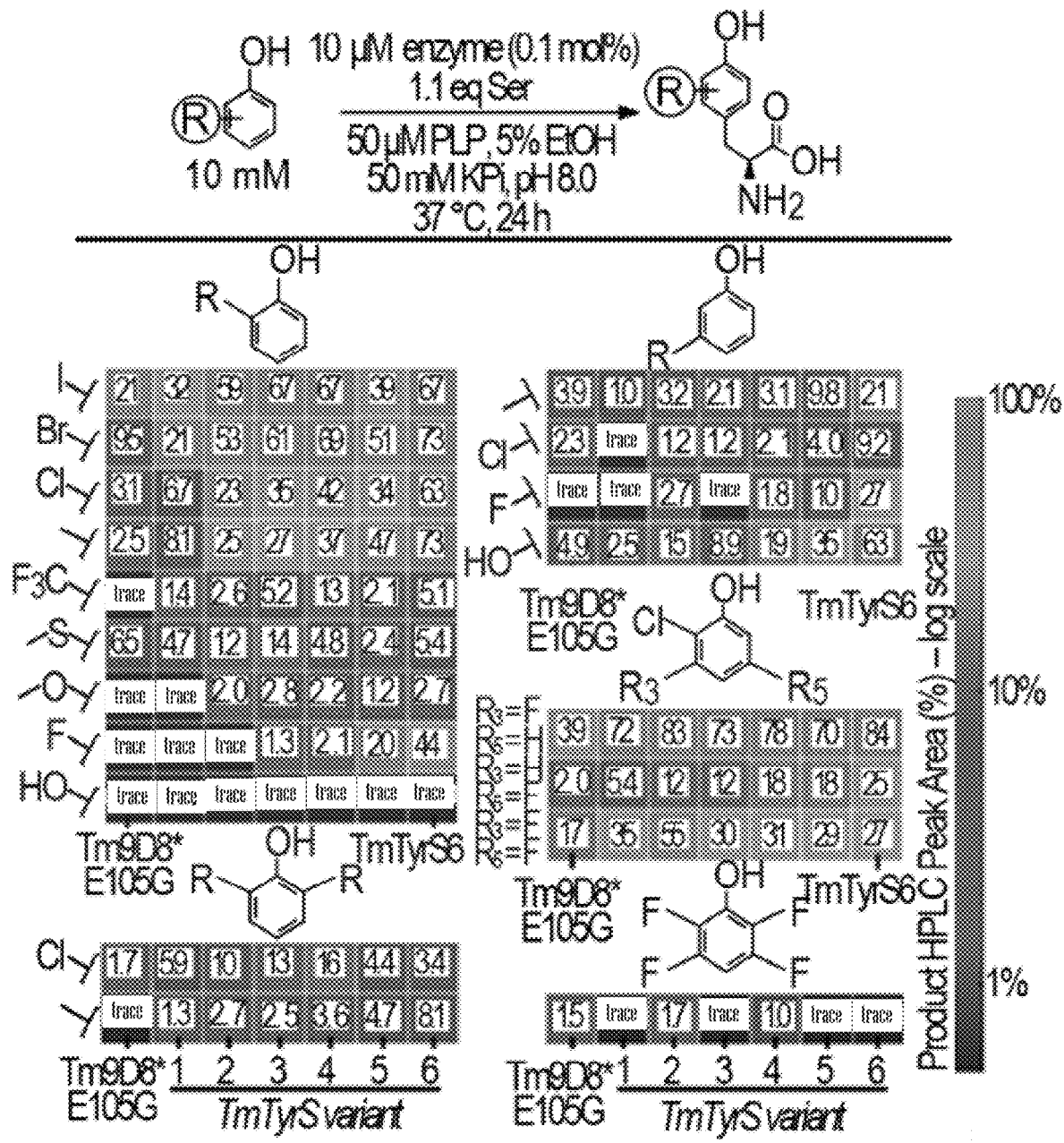
FIG. 4A is a chart representing a summary of the substrate scope of enzymes in the evolutionary lineage. Substrates are grouped by position of substitution(s). Numbers represent the percent HPLC peak area of the product relative to both product and substrate for each reaction as an approximation of product formation. Values are an average of two replicates. Values under 1% are designated as trace.

FIG. 4A shows the activity of each enzyme for each substrate. The percentages listed within the boxes are estimates of HPLC yields/conversions, but are not adjusted with a calibration curve, as many of the standards are commercially inaccessible. Instead, product formation was estimated by assuming that the HPLC peak areas were equally proportional to compound concentration. Formally, this is only true at the isosbestic point between the substrate and the red-shifted product (see FIG. 1A). However, red shifts were generally slight, and still provide a reliable means of estimating product formation among different reactions. Moreover, the relative trends are exactly true within a given substrate row. In other words, in FIG. 4A the effect of evolution on a given substrate can be seen exactly, while the effect of evolution across different substrates can be reasonably approximated.

Where there is an obvious difference in the total absorbance of the substrate and product peaks compared to high- and low-yielding reactions, these values are the least reliable. Thus, if the formation of product significantly changes the total absorbance in the system, then there is an obvious difference in absorbance between the substrate and product peaks at the given wavelength. These data are shown in FIG. 2. Generally, the change in total absorbance is not dependent on the area of the product peak, making these reliable estimates of conversion. All product absorbance peaks were correlated with their respective MS peaks, allowing confident identification of the product peak in even low-conversion reactions.

All reactions were run according to the conditions presented in FIG. 4A (10 µM enzyme, 10 mM phenolic substrate, 11 mM Ser, in KPi at 37° C. for 24 hours) using the methods as described in Example 8. LCMS traces were processed by integrating the absorbance peak of the product and the known substrate absorbance peak. In cases of particularly low activity where a reliable mass peak could not be observed by extracted ion counts (EIC) obtained from the total ion count (TIC) signal, single-ion mode (SIM) was used to observe the product MS peak. If no reliable absorbance peak was observed above background but an MS peak was observed in the EIC or SIM signals, activity was labeled as "trace".

For simplicity and because the enzymatic reactions are generally highly specific (e.g., no side products) only the substrate and product peaks were integrated and processed. Only two substrates showed some deviation. Traces for the (2-MeS-phenol) reactions indicated the presence of an oxidized substrate, presumably to the sulfoxide (2-MeSO-phenol) based on the mass and absorbance difference. However, the peak was relatively minor compared to the substrate peak, had significant differences in its absorbance, and was omitted from the conversion analysis for consistency. Additionally, many peaks were observed for the 2-CF$_3$-phenol substrate. Not intending to be bound by theory, data suggests that this substrate was not of high purity.

Example 22: Identification of a Starting Point for Evolution of Tyrosine Synthase (TyrS) Activity Given that TPL uses an amino-acrylate intermediate to accomplish Tyr analog synthesis (and degradation), it was suspected that TrpB could react with phenols, but differences between the two enzyme reactions highlighted potential challenges. Phenol is a small, symmetric molecule with a single heteroatom and three nucleophilic positions: the carbon atoms ortho and para to the hydroxyl as well as the hydroxyl itself; Tyr synthesis requires a highly para-selective catalyst. In TPL, multiple residues coordinate the phenolic hydroxyl group to facilitate para C—C bond breakage, which also lowers the energy barrier for the reverse reaction, formation of that same bond. A catalytic glutamate present in all characterized TrpB enzymes plays a similar role, to coordinate indole during Trp synthesis. Milić et al., Structures of apo- and holo-tyrosine phenol-lyase reveal a catalytically critical closed conformation and suggest a mechanism for activation by K ions. *Biochemistry.* 45, 7544-7552 (2006); Watkins et al., Direct enzymatic synthesis of a deep-blue fluorescent noncanonical amino acid from azulene and serine. *ChemBioChem.* 21, 80-83 (2019). It was thus considered that a TyrS might need an analogous coordination mechanism to favor para C—C bond formation over ortho or O-alkylation.

When representative engineered TrpB variants were challenged with phenol and Ser, however, none of the three possible amino-acid products were observed, which prompted looking for a substrate that might serve as an evolutionary intermediate between indole and phenol (FIG. 8A). 1-naphthol was selected as an electron-rich phenol analog similar enough to indole to bind in the active site and also be aligned for para C—C bond formation (FIG. 8B). Both TrpB variants tested-T$_m$9D8*(SEQ ID NO: 3), from *Thermotoga maritima* and engineered for 4-cyano-Trp formation at 37° C., and Pf2B9 (SEQ ID NO: 12), from *Pyrococcus furiosus* and engineered for β-methyl-Trp production at 75° C.—reacted with 1-naphthol and Ser to form an amino acid product. SEQ ID NO: 3 was selected for further evolution because it retained high thermostability while also displaying good activity at 37° C., necessary for in vivo applications. Boville et al., Improved synthesis of 4-cyanotryptophan and other tryptophan analogs in aqueous solvent using variants of TrpB from *Thermotoga maritima*. *J. Org. Chem.* 83, 7447-7452 (2018); Herger et al., Synthesis of β-branched tryptophan analogues using an engineered subunit of tryptophan synthase. *J. Am. Chem. Soc.* 138, 8388-8391 (2016).

Example 23: Directed Evolution of a Tyrosine Synthase (TyrS)

Under the presumption that 1-naphthol was binding in a similar orientation to the natural indole substrate of TrpB, it appeared likely that the catalytic glutamate that aligns indole might not be optimal for this non-native substrate (FIG. 8B). Site-saturation mutagenesis and screening at this position identified three highly activating mutations: E105G, E105A, and E105S (all 'small' side chains). The E105G mutation provided the largest rate enhancement (18-fold over SEQ ID NO: 3). The para-alkylation product β-(1-naphthol-4-yl)-L-alanine (NaphAla) was the sole product of this enzymatic reaction.

It was determined that SEQ ID NO: 4 could be evolved for activity on phenol by first increasing activity on 1-naphthol and then moving to other substrates that are more similar to phenol as new activities appear in a 'substrate walk' (FIG. 8A and FIG. 8C). Chen & Zhao, Rapid creation of a novel protein function by in vitro coevolution. *J. Mol. Biol.* 348, 1273-1282 (2005). This approached could yield an enzyme for Tyr synthesis while simultaneously creating a panel of biocatalysts for the synthesis of valuable Tyr analogs. SEQ ID NO: 4 was subjected to sequential rounds of mutagenesis and screening for NaphAla synthesis, eventually producing variant SEQ ID NO: 6 (*T. maritima*-derived tyrosine synthase enzyme 1). Remarkably, this enzyme displays a $k_{cat}$ of 11 min$^{-1}$ for the conversion of 1-naphthol to NaphAla (FIG. 1), roughly half that of SEQ ID NO: 3 for Trp formation (21 min-1, FIG. 8B) and approaching the rates of native TrpB enzymes. Not intending to be bound by theory, data suggests that TyrS enzymes could be evolved to function at a level that supports life. Buller et al., Directed evolution of the tryptophan synthase β-subunit for stand-alone function recapitulates allosteric activation. *Proc. Natl. Acad. Sci. U.S.A.* 112, 14599-14604 (2015).

Continuation of this substrate walk approach required a more 'phenol-like' substrate for further screening. Fortunately, directed evolution for 1-naphthol activity also increased activity toward 2-chlorophenol to form the para-alkylated 3-chloro-Tyr product. Thus, SEQ ID NO: 6 was evolved for activity on 2-chlorophenol to generate variants SEQ ID NO: 7-9 (FIG. 8C, Example 19). The rates of phenol and 2-chlorophenol conversion increased similarly over the course of evolution, but activity on phenol was far lower, suggesting that the 2-chloro substituent has an activating effect.

Comparison of 2-chloro- and 2-methylphenol as substrates revealed similar levels of activity despite the electronic differences between these substituents. This indicated that steric bulk at the 2-position likely plays an important role in the proper orientation of these substrates. Achieving a productive orientation with the unsubstituted phenol substrate is thus potentially challenging in the absence of sterically confining residues. By targeting the active site for further mutagenesis and screening for Tyr synthesis substantially more active variants, SEQ ID NO: 10 and 11, were obtained (FIG. 8C and FIG. 8D). Not intending to be bound by theory, the mutation of an active-site glycine to alanine (G229A) in SEQ ID NO: 10, which adds steric bulk within the active site, proved particularly activating. The final variant, TmTyrS6, synthesizes Tyr at an apparent turnover frequency (TOF) of 14 h$^{-1}$ (0.23 min$^{-1}$, 50 mM each substrate), see Table 6.

TABLE 6

Turnover frequencies (TOFs)

| Variant | [Enzyme] (µM) | [Phenol] (mM) | Time (h) | RT [min] | Area | [Tyr] (µM) | Turnovers | TOF (h$^{-1}$) | Mean TOF (h$^{-1}$) |
|---|---|---|---|---|---|---|---|---|---|
| Tm9D8* | 100.0 | 50 | 24 | 1.102 | 28.7681 | 0.42 | 0.0 | 0.0 | 0.0 |
| (SEQ ID | 100.0 | 50 | 24 | 1.105 | 26.2847 | 0.38 | 0.0 | 0.0 | |
| NO: 3) | 100.0 | 50 | 24 | 1.104 | 21.0719 | 0.29 | 0.0 | 0.0 | |
| Tm9D8* | 100.0 | 50 | 24 | 1.107 | 3217.4171 | 96 | 0.96 | 0.04 | 0.04 |
| E105G | 100.0 | 50 | 24 | 1.104 | 3172.4534 | 95 | 0.95 | 0.04 | |
| (SEQ ID | 100.0 | 50 | 24 | 1.104 | 3301.2609 | 99 | 0.99 | 0.04 | |
| NO: 4) | | | | | | | | | |
| TmTyrS1 | 100.0 | 50 | 24 | 1.101 | 2459.7951 | 70 | 0.70 | 0.03 | 0.03 |
| (SEQ ID | 100.0 | 50 | 24 | 1.098 | 2575.7915 | 74 | 0.74 | 0.03 | |
| NO: 6) | 100.0 | 50 | 24 | 1.103 | 2556.0619 | 74 | 0.74 | 0.03 | |
| TmTyrS2 | 50.0 | 50 | 24 | 1.095 | 3996.225 | 123 | 2.5 | 0.10 | 0.10 |
| (SEQ ID | 50.0 | 50 | 24 | 1.097 | 4038.0278 | 125 | 2.5 | 0.10 | |
| NO: 7) | 50.0 | 50 | 24 | 1.101 | 4148.5208 | 129 | 2.6 | 0.11 | |
| TmTyrS3 | 20.0 | 50 | 24 | 1.098 | 2952.4932 | 87 | 4.4 | 0.18 | 0.19 |
| (SEQ ID | 20.0 | 50 | 24 | 1.102 | 3123.5107 | 93 | 4.6 | 0.19 | |
| NO: 8) | 20.0 | 50 | 24 | 1.098 | 3149.8636 | 94 | 4.7 | 0.2 | |
| TmTyrS4 | 10.0 | 50 | 24 | 1.102 | 1869.0759 | 51 | 5.1 | 0.21 | 0.22 |
| (SEQ ID | 10.0 | 50 | 24 | 1.095 | 1860.3236 | 51 | 5.1 | 0.21 | |

TABLE 6-continued

Turnover frequencies (TOFs)

| Variant | [Enzyme] (µM) | [Phenol] (mM) | Time (h) | RT [min] | Area | [Tyr] (µM) | Turnovers | TOF (h$^{-1}$) | Mean TOF (h$^{-1}$) |
|---|---|---|---|---|---|---|---|---|---|
| NO: 9) | 10.0 | 50 | 24 | 1.098 | 1986.5306 | 55 | 5.5 | 0.23 | |
| TmTyrS5 | 10.0 | 50 | 24 | 1.094 | 28267.4655 | 1170 | 117 | 4.9 | 5.0 |
| (SEQ ID | 10.0 | 50 | 24 | 1.1 | 28779.4787 | 1200 | 120 | 5.0 | |
| NO: 10) | 10.0 | 50 | 24 | 1.098 | 29631.6258 | 1240 | 124 | 5.2 | |
| TmTyrS6 | 10.0 | 50 | 24 | 1.096 | 72206.0343 | 3460 | 346 | 14 | 14 |
| (SEQ ID | 10.0 | 50 | 24 | 1.099 | 71630.5227 | 3430 | 343 | 14 | |
| NO: 11) | 10.0 | 50 | 24 | 1.099 | 67582.34 | 3210 | 321 | 13 | |

These evolved enzymes are at least 99.5% regio- and enantio-selective for Tyr synthesis; no D-Tyr was detected, consistent with the TrpB mechanism, and no ortho-alkylation was detected even when the concentration of enzymatically prepared Tyr was >1000-fold higher than the limit of detection. The approximate turnover frequencies are presented on a log scale in FIG. 8D, along with a conservative lower bound for the detectable amount of Tyr under the given conditions (see Example 20). Because SEQ ID NO: 3 did not make Tyr exceeding this threshold, the evolution presented here represents at least a 30,000-fold increase in activity from SEQ ID NO: 3 to SEQ ID NO: 11.

Example 24: General Description of Evolutionary Strategies

Many different strategies were used to achieve the rate enhancement in TmTyrS6. If not specified, experimental details for each type of mutagenesis (error-prone PCR mutagenesis, StEP recombination, and site-saturation mutagenesis (SSM)) and screening (colorimetric, LCMS) approach is the same as described in the above Examples. General details about what was performed to obtain each variant in the lineage follow.

SEQ ID NO: 4 was identified by generating a saturation mutagenesis library at position 105 and screening enzyme variants against 0.5 mM 1-naphthol for 4 and 18 hours using a colorimetric assay (see FIG. 1A), and wells demonstrating high activity were analyzed by LCMS to confirm product formation. Following this, saturation mutagenesis at position 184—which has been shown to often have a beneficial effect for new substrates—was performed and screened similarly, identifying F184P as a beneficial mutation (~2-fold boost for NaphAla formation).

SEQ ID NO: 6 was identified by subjecting SEQ ID NO: 5 to highly error-prone PCR mutagenesis (>600 µM MnCl$_2$), which generated a library of highly mutated enzyme variants (~8 mutations per variant). Enzymes were prepared as heat-treated lysates (3-hour heat-treatment). A total of eight plates (704 variants) were screened. Activity determination took place via a continuous colorimetric screen against 5 mM 1-naphthol at room temperature using a Tecan® Spark® Spark-Stack™ in kinetics mode (wavelength=335 nm) (Tecan Life Sciences, Switzerland). Variants that retained >50% parent activity (~40 variants) were subjected to StEP recombination. From this recombination library, four plates were screened in a similar way. The most-improved variants were once again subjected to recombination and four plates were again screened. This resulted in a panel of improved variants with groups of common mutations. Variants were compiled in biological replicate into a new plate and screened against 5 mM 1-naphthol (in the same way as previously) as well as 25 mM 2-chlorophenol and 50 mM 2-fluorophenol via LCMS. Mutations were recombined that were general for all substrates, yielding SEQ ID NO: 6. (Incidentally, F184P was identified to be neutral for 2-chlorophenol and deleterious for 2-fluorophenol, despite being highly activating for 1-naphthol.)

Following SEQ ID NO: 6, evolution proceeded using standard error-prone PCR mutagenesis techniques and StEP recombination. SEQ ID NO: 7 was identified by screening against 25 mM 2-chlorophenol using a 0.65-minute LCMS method screening on a C-18 guard column for sufficient separation of substrate and product with a total of 1.2 minutes between injections (2 mL/min flow rate; 0.00 min: 1% MeCN; 0.01 min: 95% MeCN; 0.26 min: 1% MeCN; hold to 0.65 min; post-time: 0.25 min). SEQ ID NO: 8 was identified by screening against 10 mM 2-chlorophenol in the same way.

SEQ ID NO: 8 was sufficiently active and could detect Tyr formation in enzyme lysate, which harbors background Tyr from the cells that previously made such screening impossible. However, such detection required 50 mM phenol loading, long reaction times, and a 4-minute LCMS method to reliably detect the Tyr. A final round of screening against 5 mM 2-chlorophenol was performed, and enzyme variant sequences were determined using the evSeq method. Wittmann et al., evSeq: Cost-Effective Amplicon Sequencing of Every Variant in a Protein Library. ACS Synth. Biol. 11, 1313-1324 (2022). SEQ ID NO: 8 was subjected to SSM within the active site to identify the mutation P184A as highly activating. SEQ ID NO: 8 P184A was subjected to additional rounds of error-prone PCR mutagenesis and recombination and screened via both LCMS and a colorimetric screen (wavelength=310 nm). This resulted in SEQ ID NO: 9.

When the SEQ ID NO: 8 SSM libraries were screened against phenol, the mutation G229A was observed to be highly activating (~3-fold improvement). This mutation was added to SEQ ID NO: 9 but was not observed to have the same effect. SEQ ID NO: 9 and SEQ ID NO: 8 P184A were recombined via StEP, and G229A was found to be activating only in the absence of the S265P mutation, which was kept reverted. This variant was subjected to additional error-prone PCR mutagenesis and recombination, screening against 10 mM phenol on the 0.65-min LCMS method (single-ion mode for 182 m/z) to identify SEQ ID NO: 10. Screening against 5 mM phenol conversion, a final round of SSM (to identify L170F) and error-prone PCR mutagenesis and recombination led to TmTyrS6.

Example 25: TyrS Enzymes are Efficient Biocatalysts

Given that different substrates were targeted over the course of TyrS evolution, variants in this lineage should serve as biocatalysts for efficient synthesis of a variety of noncanonical Tyr analogs. To assess the substrate preferences and efficiencies of these enzymes, a panel of phenolic substrates was tested against each TyrS variant, starting with SEQ ID NO: 4. To provide a consistent means of comparison, each substrate was added at 10 mM. The reactions were performed with 1.1 equivalents of Ser relative to the phenolic substrate. Under these conditions, high yields can only be achieved with excellent conversion of both the phenol and Ser to the Tyr analog. This requires the exertion of kinetic control by the enzyme to avoid reversibility as well as minimal conversion of the amino-acrylate to pyruvate and ammonia, a known side reactivity of some TrpB enzymes. Herger et al., Synthesis of β-branched tryptophan analogues using an engineered subunit of tryptophan synthase. *J. Am. Chem. Soc.* 138, 8388-8391 (2016); Romney et al., Unlocking reactivity of TrpB: A general biocatalytic platform for synthesis of tryptophan analogues. *J. Am. Chem. Soc.* 139, 10769-10776 (2017). A diverse profile of activities was observed, with high conversions achieved in many cases (see Example 21, FIG. 4A and FIG. 2). Selected products were isolated and always identified as the para-alkylation product. Importantly, at least one variant displays reasonable initial activity (>1%) for all but one substrate.

Figure 4B:
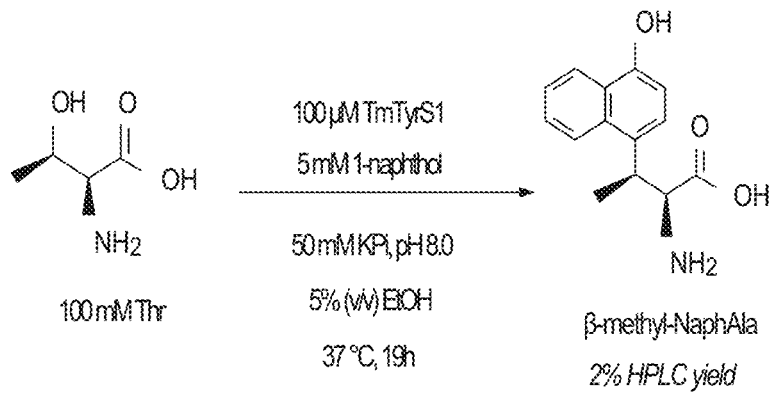
FIG. 4B is a schematic showing that TyrS variants can accept a β-branched Ser analog to synthesize a β-branched Tyr analog in a single step.
Figure 4C:
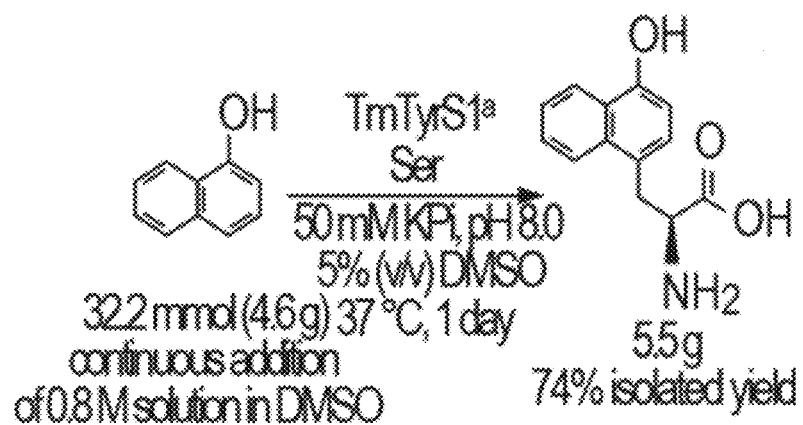
FIG. 4C is a schematic and picture of chromatography-free preparation of NaphAla at multi-gram scale. $^a$Catalyst prepared as a lyophilized powder from heat-treated lysate.
Figure 4C:
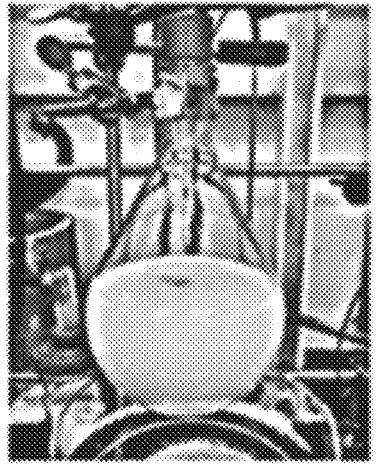

The proficiency of this platform can be demonstrated by altering the reaction conditions. Although the only substrate that consistently showed only trace reactivity was 2-hydroxyphenol, the rate of product formation for this and most other reactions was improved by increasing the concentration of substrate. Product formation as detected by mass spectrometry was increased over the course of evolution. The 1-naphthol analog and metal chelator 8-hydroxyquinoline was accepted as a substrate as well. Activity was also observed using L-threonine (Thr) in place of Ser to furnish β-methyl-Tyr analogs in a single step (FIG. 4B). Consistent with the native activity of TrpB, these enzymes do not degrade their amino acid products. For example, incubation of NaphAla, 3-chloro-Tyr, and 3-iodo-Tyr with 10 µM enzyme for 20 hours resulted in near-complete or complete retention of the amino acid (data not shown). HPLC traces showed the irreversibility of the enzymes. Saturated solutions of NaphAla, 3-iodo-Tyr, and 3-chloro-Tyr were incubated with 10 µM of the enzyme that has the highest activity toward each respective phenol analog. Under thermodynamic control, as with TPL, this would also be the enzyme that best degrades the product. Analysis of approximate areas in which the phenol analogs elute remained flat. Only NaphAla displayed very minor degradation at a rate far less than its rate of NaphAla synthesis, indicating that these reactions remain under kinetic control and are effectively irreversible.

TyrS variants can be used for gram-scale synthesis of valuable Tyr analogs in a manner similar to that described for its progenitor enzyme, TrpB, in the production of other ncAAs at scale. Dick et al., Tailoring tryptophan synthase TrpB for selective quaternary carbon bond formation. *J. Am. Chem. Soc.* 141, 19817-19822 (2019); Watkins et al., Direct enzymatic synthesis of a deep-blue fluorescent noncanonical amino acid from azulene and serine. *ChemBioChem.* 21, 80-83 (2019); Boville et al., Improved synthesis of 4-cyanotryptophan and other tryptophan analogs in aqueous solvent using variants of TrpB from *Thermotoga maritima*. *J. Org. Chem.* 83, 7447-7452 (2018). Although high concentrations of phenolic substrates destabilize the enzyme (e.g., above 50 mM 2-methylphenol, 25 mM 2-chlorophenol, or 10 mM 1-naphthol), this can be overcome by slow addition of the phenolic substrate. The preparation of NaphAla, a commercially unavailable blue-fluorescent ncAA whose applications have been limited by its challenging synthesis, was examined first. Knör et al., Efficient enantioselective synthesis of condensed and aromatic-ring-substituted tyrosine derivatives. *J. Org. Chem.* 71, 5625-5630 (2006). Over the course of 24 hours, 1-naphthol ($0.14/g, Millipore-Sigma, Burlington, MA) was slowly added to a solution of SEQ ID NO: 6 and Ser ($0.77/g) to generate the NaphAla product, which precipitated from solution toward the end of the substrate addition (FIG. 4C, Example 15). The resultant solid was collected over a filter, washed with ice-cold water and ethyl acetate to remove buffer salts and unreacted substrates, and subsequently dried in vacuo, affording 5.5 g of pure NaphAla (74% isolated yield relative to 1-naphthol, 91% weight purity, >99% enantiomeric excess (ee), FIG. 3) without significant reaction optimization. For comparison, the reported chemical synthesis required three steps and an expensive rhodium catalyst to arrive at an enantioenriched, triply protected NaphAla product from 4-hydroxy-1-naphthaldehyde ($30/g), with three more deprotection steps to yield NaphAla. Knör et al., Efficient enantioselective synthesis of condensed and aromatic-ring-substituted tyrosine derivatives. *J. Org. Chem.* 71, 5625-5630 (2006).

A similar approach was used to synthesize 3-methyl-Tyr from 2-methylphenol (<$0.1/g), a Tyr analog made by radical S-adenosyl methionine (SAM)-catalyzed methylation of Tyr in the biosynthesis of saframycin A. Tang et al., Characterization of SfmD as a heme peroxidase that catalyzes the regioselective hydroxylation of 3-methyltyrosine to 3-hydroxy-5-methyltyrosine in saframycin A biosynthesis. *J. Biol. Chem.* 287, 5112-5121 (2012). This simple ncAA is costly (~$1600/g) and is prepared synthetically via cross coupling of tetramethyltin and 3-iodo-Tyr occurring over six days at 70° C. or using TPL followed by chromatographic purification. Schmidt et al., Synthesis of tyrosine derivatives for saframycin MX1 biosynthetic studies. *Tetrahedron Lett.* 45, 3921-3924 (2004); Kim et al., Tyrosine analogues as alternative substrates for protein tyrosine kinase Csk: Insights into substrate selectivity and catalytic mechanism. *Bioorg. Med. Chem.* 8, 1263-1268 (2000); Nagasawa et al., Syntheses of L-tyrosine-related amino acids by tyrosine phenol-lyase of *Citrobacter intermedius*. *Eur. J. Biochem.* 117, 33-40 (1981). Using SEQ ID NO: 9, two sequential additions of 50 mM 2-methylphenol (separated by 12 hours) resulted in compound precipitation at >90% conversion, allowing isolation of 1.13 g of 3-methyl-Tyr without chromatographic purification (49% isolated yield relative to 2-methylphenol, 89% weight purity, >99% ee, FIG. 5). As shown in FIG. 4A, SEQ ID NO: 9 demonstrates moderate conversion of 2-methylphenol (42% product HPLC peak area). Not intending to be bound by theory, this value can serve as a benchmark for the preparation of other compounds at scale.

These gram-scale syntheses are simple and effective. They take place at 37° C. in a ~100 mL volume per gram of product (roughly 10 g $L^{-1}$ day$^{-1}$ space-time yield) using inexpensive reagents and enzyme obtained from a 1-L bacterial culture. The high stability of the TyrS enzymes facilitates their preparation as bench-stable lyophilized powder from heat-treated lysate. The heat treatment removes nearly all mesophilic *E. coli* host proteins.

Example 26: Conservation of the Catalytic Glutamate in TrpB-Like Sequences

Human-annotated TrpB sequences from the SwissProt database were obtained and aligned to obtain a multiple sequence alignment (MSA) referenced to the sequence of SEQ ID NO: 3. The catalytic glutamate was strictly conserved in all characterized TrpB enzymes within the human-annotated SwissProt database (451 sequences).

Figures 10A, 10B, 10C:
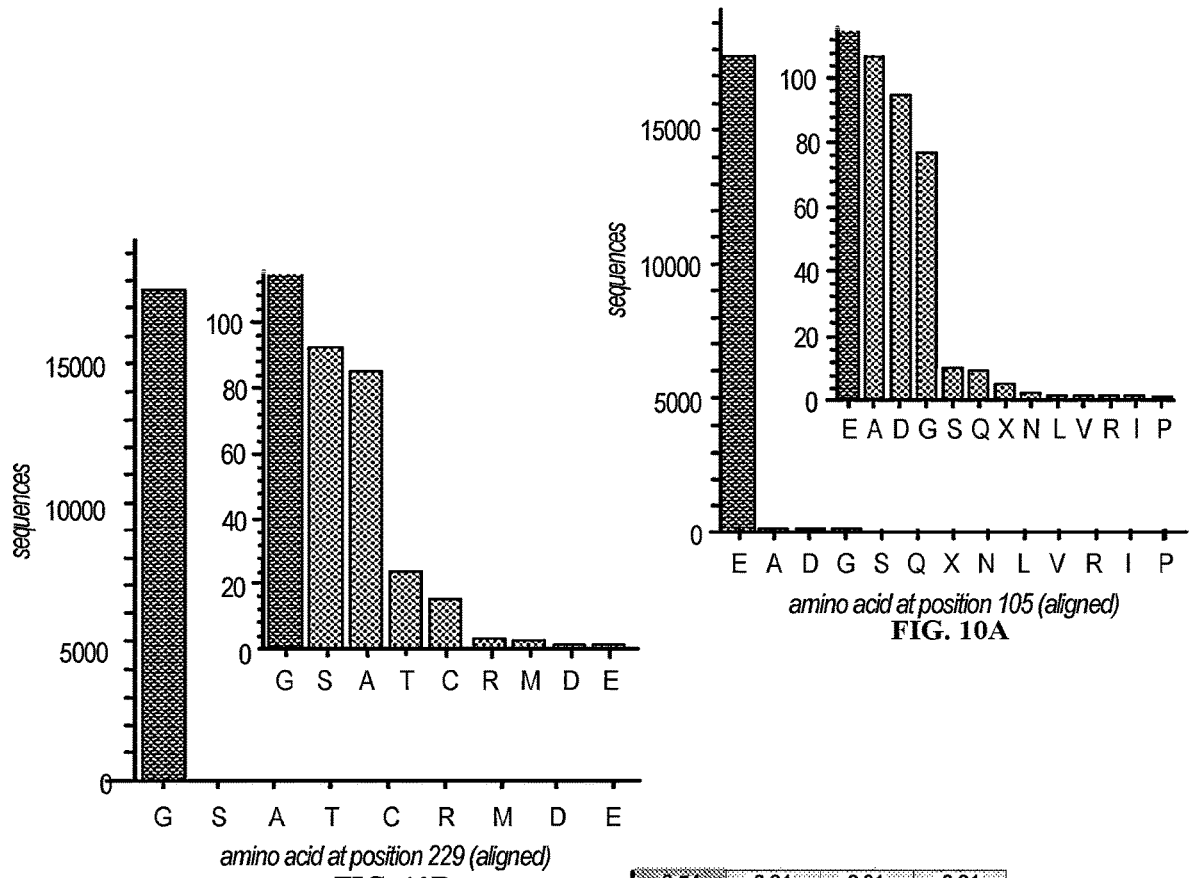
FIG. 10A shows a graph of the number of sequences with a given amino acid at position 105. Inset: Axis-adjusted view. Ala (A), Asp (D), and Gly (G) are the only other amino acids with significant frequencies.
FIG. 10B shows a graph of the number of sequences with a given amino acid at position 229. Inset: Axis-adjusted view. Ser(S), Ala (A), and Thr (T) are the only other amino acids with significant frequencies.
FIG. 10C shows a chart depicting the correlations of amino acids found at position 105 and 229. While the vast majority of sequences contain the residues native to TmTrpB (E105, G229; 97.78%), those with non-carboxylate (e.g., not E or D) sidechains at position 105 are correlated with different amino acid identities at 229: E105A+G229S/T (0.53%); and E105G+G229A (0.35%). The latter are the same mutations identified in this study that proved most beneficial for activity with phenol.

The multiple sequence alignment (MSA) of 18,719 TrpB-like sequences was obtained from the EVcouplings software. Hopf et al., The EVcouplings Python framework for coevolutionary sequence analysis. *Bioinformatics.* 35, 1582-1584 (2019). Of note, 693 variants that did not contain an appropriately positioned catalytic lysine (K83) or had an insertion at position 105 in the MSA (i.e., from an improperly aligned and/or non-TrpB-like sequence) were discarded, leaving 18,051 sequences with 14-93% aligned sequence identity to SEQ ID NO: 3. Of these, 98.28% (17,741) contained the catalytic glutamate (FIG. 9B). Only three other amino acids occurred with a significant frequency, those being alanine (0.59%; 107), aspartate (0.53%; 95), and glycine (0.43%; 77). The residue corresponding to G229, where alanine was found to be activating in SEQ ID NO: 10, was equally conserved (98.20%; 17,726), but differences at this position were notably present in sequences in which the catalytic glutamate was absent (FIG. 7). Thus, the sequences were analyzed based on their amino acids at position 105 (FIG. 4A and FIG. 10A) and 229 (FIG. 10B) as discussed in Example 26. Correlations were observed by examining the identities at these positions within a given sequence (FIG. 10C). Most sequences with the E105A+G229S/T pair were derived from plants, while those with the E105G+G229A pair were found in *Streptomyces* and related soil bacteria from the phylum Actinobacteria.

Example 27: The E105G Mutation is Generally Activating

Because a significant amount of the rate enhancement achieved by directed evolution can be attributed to the single E105G mutation, whether this mutation is activating in other TrpBs was investigated. Installation of the equivalent E104G mutation in SEQ ID NO: 12 (corresponding to E105G of SEQ ID NO: 1), which had previously demonstrated activity with 1-naphthol, increased this activity 7.8-fold at this enzyme's optimal temperature of 75° C. (FIG. 9A). In both TrpBs, these mutations decreased activity toward indole to levels below those on 1-naphthol, and regioselectivity for indole alkylation was no longer >99.5%, as previously observed. Romney et al., Unlocking reactivity of TrpB: A general biocatalytic platform for synthesis of tryptophan analogues. *J. Am. Chem. Soc.* 139, 10769-10776 (2017); Watkins et al., Direct enzymatic synthesis of a deep-blue fluorescent noncanonical amino acid from azulene and serine. *ChemBioChem.* 21, 80-83 (2019).

Removal of the glutamate side chain enhanced activity on simple phenol analogs to an even greater extent under all tested conditions (FIG. 9A). This mutation effected a 30-fold increase in the activity of SEQ ID NO: 12 toward 2-chlorophenol and a 40-fold increase toward 2-iodophenol. SEQ ID NO: 4 saw an even more impressive 400-fold increase over SEQ ID NO: 3 when provided 2-iodophenol. In both $T_m$9D8*(SEQ ID NO: 3) and Pf2B9 (SEQ ID NO: 12) variants, this sole glutamate-to-glycine substitution was sufficient to enable Tyr formation with increased enzyme and substrate concentration (FIG. 9A).

Example 28: Structural and Kinetic Analysis of Regioselective Phenol Alkylation

Figure 6:
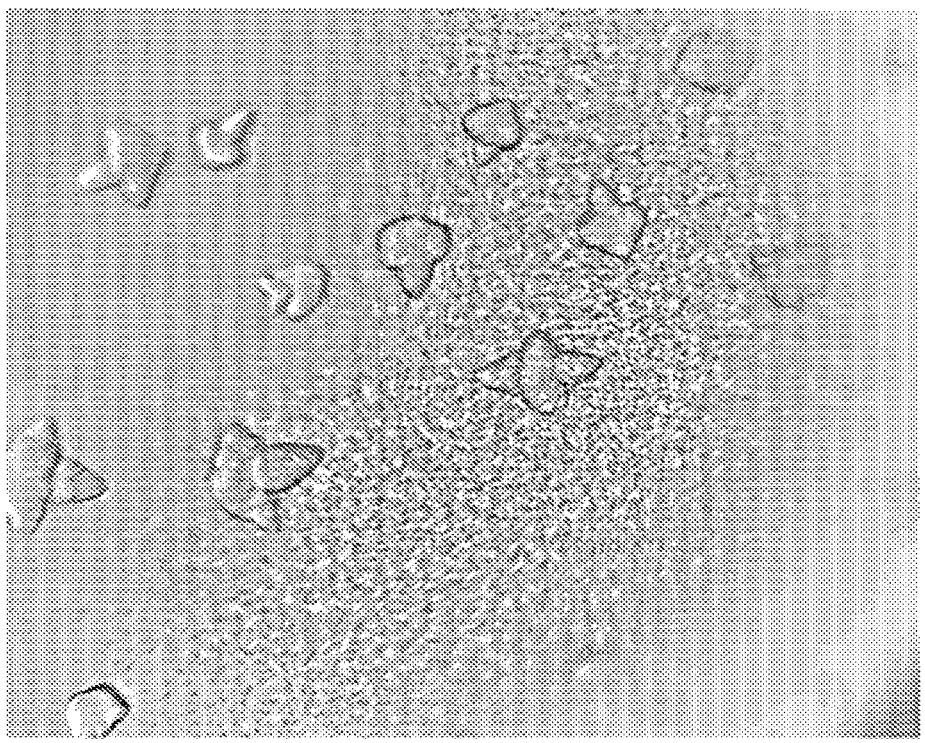
FIG. 6 is a picture of the star-shaped crystals of TmTyrS1 (SEQ ID NO: 6).
Figure 11A:
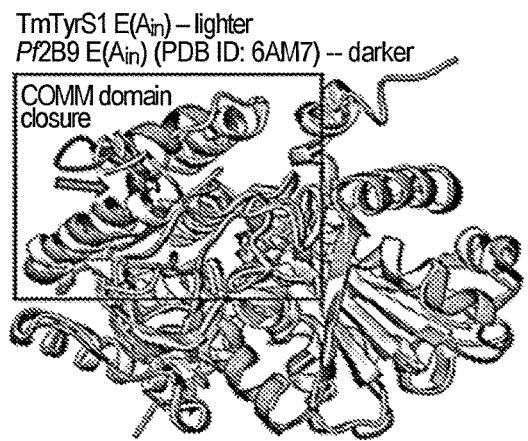
FIG. 11A is a cartoon of the internal aldimine $E(A_{in})$ resting state (lighter) compared to the $E(A_{in})$ state of a different stand-alone TrpB variant, Pf2B9 (SEQ ID NO: 12) (darker).

The enzymatic products were always para-alkylated, leaving ortho- and O-alkylation unobserved during evolution or in the substrate scope analysis. The regioselectivity of TyrS should, at a minimum, be achieved through active-site discrimination between the para-alkylating and ortho-alkylating binding modes, while the discrimination of C- and O-alkylation may be accomplished through other means. Smith et al., Investigation of β-substitution activity of O-acetylserine sulfhydrolase from *Citrullus vulgaris*. *ChemBioChem*, e202200157 (2022). Although steric factors can be used to justify the regioselectivity when alkylating 1-naphthol, the regioselective transformation of phenol to Tyr suggests that the active site interacts with the hydroxyl group. Structural characterization of TyrS enzymes in various catalytically relevant states was pursued, including in complex with substrate analogs, to probe this further. Whereas previous studies of *T. maritima* TrpB (SEQ ID NO: 1) variants had to rely on homology models due to the absence of structural data, experimental X-ray crystal structure of a TyrS were obtained herein (FIG. 6 and FIG. 11A and Table 5). Watkins et al., Direct enzymatic synthesis of a deep-blue fluorescent noncanonical amino acid from azulene and serine. *ChemBioChem.* 21, 80-83 (2019); Boville et al., Improved synthesis of 4-cyanotryptophan and other tryptophan analogs in aqueous solvent using variants of TrpB from *Thermotoga maritima*. *J. Org. Chem.* 83, 7447-7452 (2018).

Figure 11B:
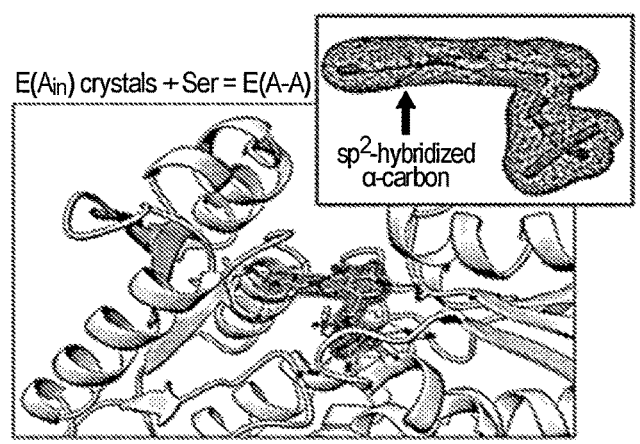
FIG. 11B is a cartoon of the active amino-acrylate-bound E(A-A) state can be obtained by simple soaking of $E(A_{in})$ crystal with Ser. Inset: Head-on view of the amino-acrylate, with the polder omit map contoured at 5σ, demonstrating the planarity of the $sp^2$-hybridized Cα.
Figure 11C:
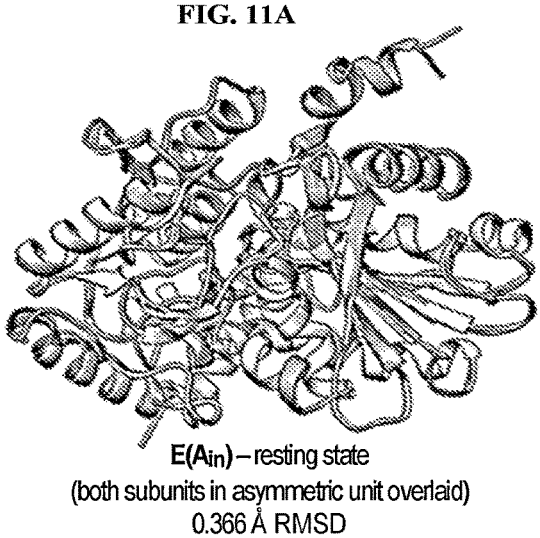
FIG. 11C is a cartoon of the structural changes resulting from the addition of Ser to $E(A_{in})$ crystals, reducing the conformational heterogeneity between the two TmTyrS1 (SEQ ID NO: 6) subunits in the asymmetric unit (each subunit aligned and colored lighter or darker).
Figure 11C:
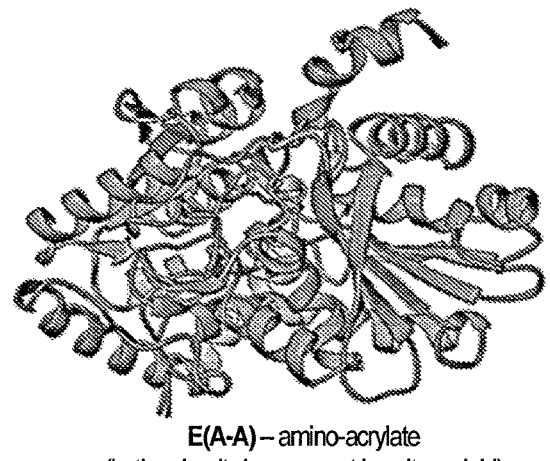

Previous reports have shown that stable amino-acrylate complexes can be formed and observed directly in TrpB crystals that are in the resting internal aldimine $E(A_{in})$ state, which would allow examination of the reactive state of these enzymes. Soaking Ser into the crystals readily formed the amino-acrylate-bound E(A-A) complex in both subunits (FIG. 9C, inset, and FIG. 11B). Buller et al., Directed evolution mimics allosteric activation by stepwise tuning of the conformational ensemble. *J. Am. Chem. Soc.* 120, 7256-7266 (2018). Not intending to be bound by theory, the ability to observe this reactive intermediate so easily highlights its stability within the TrpB scaffold. In contrast, the transient amino-acrylate of TPL could only be assumed to exist until spectroscopic evidence was obtained through kinetic trapping with an inhibitor. Phillips et al., Aminoacrylate intermediates in the reaction of *Citrobacter freundii* tyrosine phenol-lyase. *Biochemistry.* 45, 9575-9583 (2006). In both the $E(A_{in})$ and E(A-A) structures of SEQ ID NO: 6, removal of the E105 sidechain made space for the coordination of a single water molecule in the active site. Furthermore, this coordinated water interacted with a second water molecule in the E(A-A) structure. Based on conserved indole interactions in TrpB, naïve modeling of 1-naphthol in a productive binding mode places the phenolic hydroxyl group in an orientation that would displace the second water molecule (FIG. 9C). Active-site water molecules are well established to enable catalysis through electrostatic interactions with the functional groups of substrates. Not intending to be bound by theory, this may provide a possible rationale for how and why the TyrS enzymes described here perform this non-native reaction with exquisite regioselectivity. Kraut et al., Dissecting the paradoxical effects of hydrogen bond mutations in the ketosteroid isomerase oxyanion hole. *Proc. Natl. Acad. Sci. U.S.A.* 107, 1960-1965 (2010).

Figure 12:
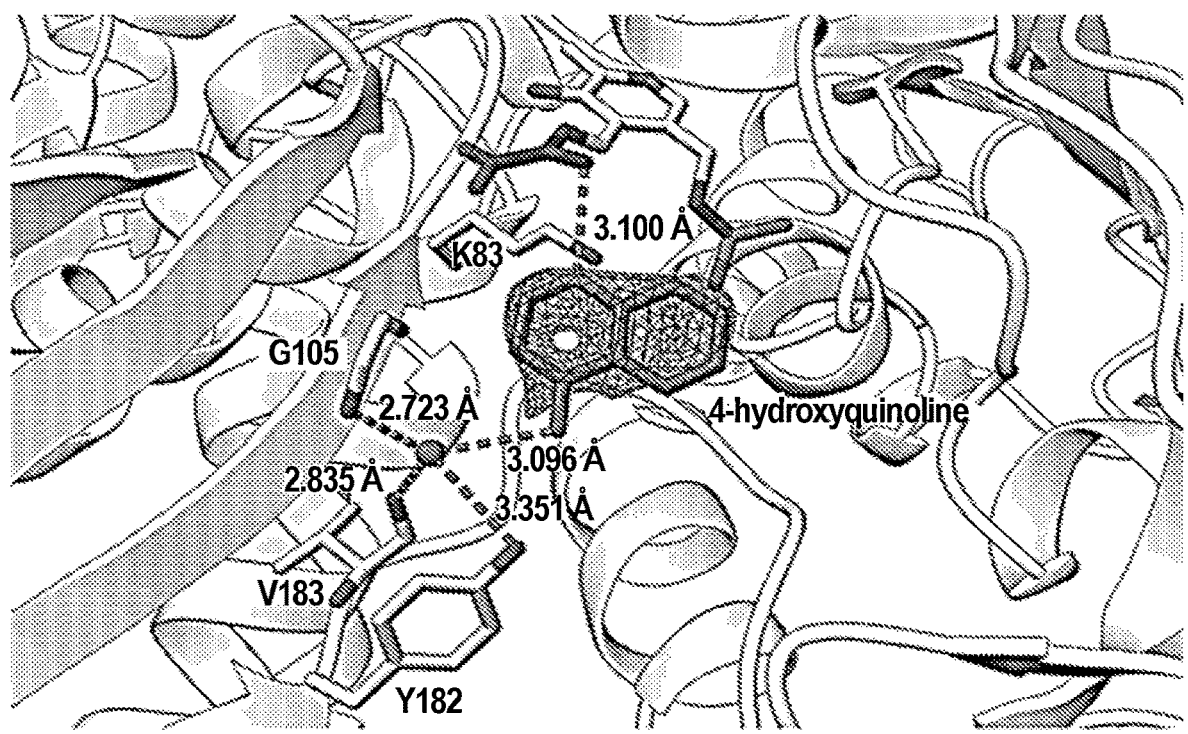
FIG. 12 is a cartoon of the crystal structure of TmTyrS1 (SEQ ID NO: 6) in the E(A-A) state bound with 4-hydroxylquinoline. Distances for hydrogen bonding and other electrostatic interactions are shown. Polder omit map contoured at 7σ.

To obtain more conclusive evidence of the role of this water in coordinating the phenolic hydroxyl group, the structure of SEQ ID NO: 6 in the E(A-A) state was determined in complex with a non-reactive 1-naphthol analog, 4-hydroxyquinoline (FIG. 12). When soaked into crystals of the E(A-A) complex, the hydroxyl group of 4-hydroxyquinoline forms a hydrogen bond with the active-site water (O—O distance of 3.1 Å), supporting its putative role in directing regioselective bond formation by SEQ ID NO: 6 (FIG. 9D). This molecule, which favors the keto tautomer (4-quinolone) in aqueous solution, may be best modeled as the enol tautomer within the enzyme active site. Not intending to be bound by theory, this is based on the short interatomic distance between the quinoline nitrogen and the electrophilic β-carbon of the amino-acrylate (N —C distance of 3.1 Å) requiring a lone pair on the heterocyclic nitrogen (FIG. 9B, inset). Such a binding mode for the structurally analogous 1-naphthol would thus direct C—C bond formation between the amino-acrylate and $C_4$ of this and other phenolic substrates, providing a satisfying structural explanation for the regioselectivity of these reactions.

Figure 13:
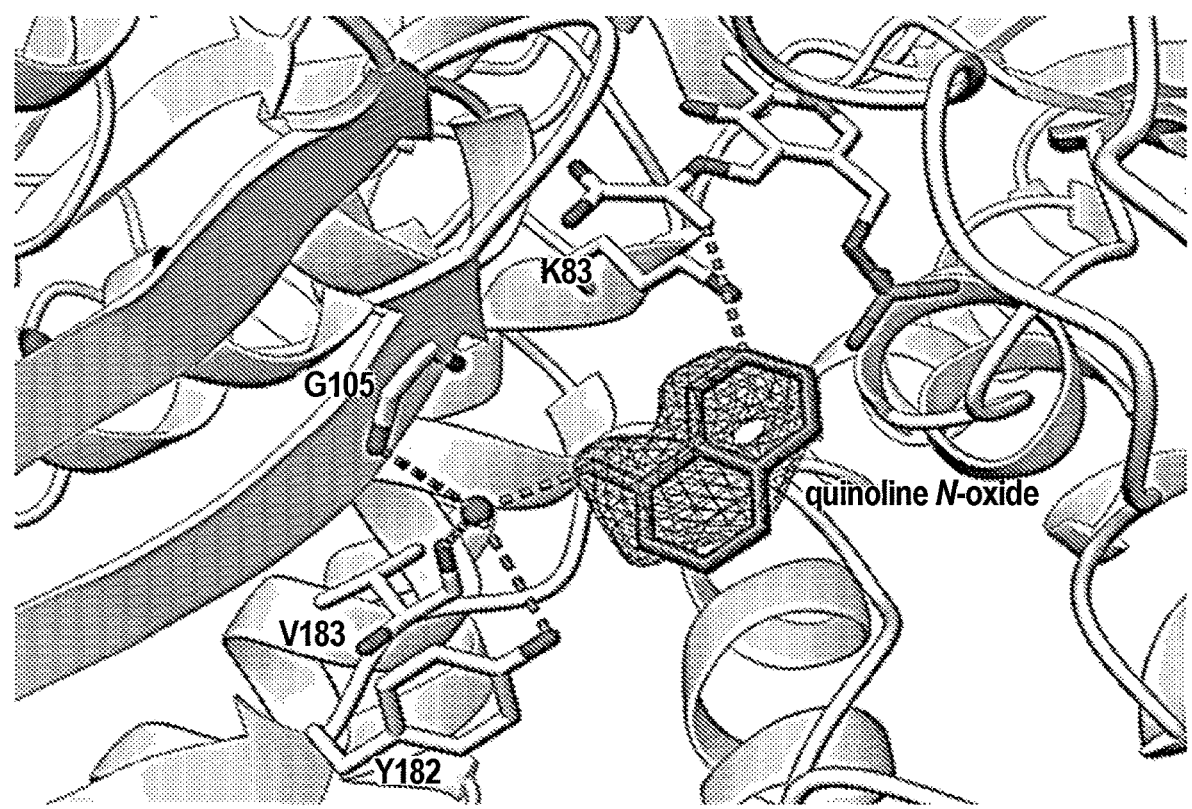
FIG. 13 is a cartoon of the crystal structure of TmTyrS1 (SEQ ID NO: 6) in the E(A-A) state bound with quinoline N-oxide. Polder omit map contoured at 7.6σ.

Soaking the SEQ ID NO: 6 crystals with 1-naphthol analog quinoline N-oxide showed this molecule could also bind within the active site of the E(A-A) complex and interact directly with the coordinated water. Interestingly, however, it was bound in a non-productive mode, with C7 oriented toward the amino-acrylate (FIG. 13). Although the C7-alkylated product was never observed, this suggests that there may be an off-target binding mode for 1-naphthol that would increase the $K_M$ of the reaction in a competitive inhibition-like fashion. Not intending to be bound by theory, this may explain why 1-naphthol displays an elevated $K_M$ of 2.8 mM (FIG. 1E), which is roughly 102-103-fold higher than that of indole in native TrpB enzymes, despite the similarity in steric bulk and the preservation of packing interactions around these two substrates. Rix et al., Scalable continuous evolution for the generation of diverse enzyme variants encompassing promiscuous activities. *Nat. Commun.* 11, 5644 (2020); Buller et al., Directed evolution mimics allosteric activation by stepwise tuning of the conformational ensemble. *J. Am. Chem. Soc.* 120, 7256-7266 (2018).

Figure 14:
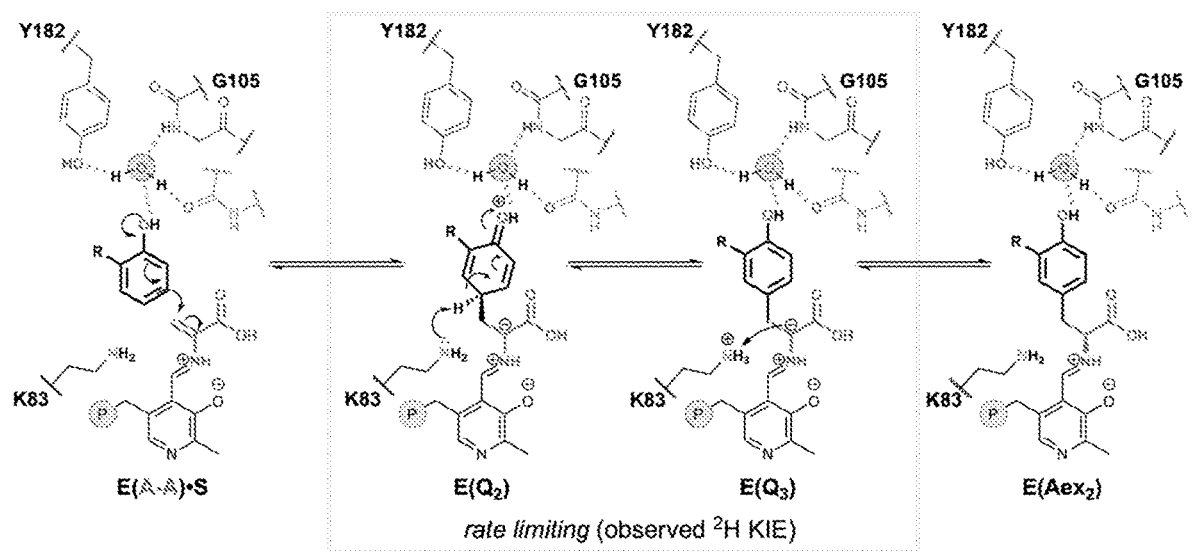
FIG. 14 is a proposed mechanism of step-wise alkylation of phenolic substrates by TyrS variants where a catalytic water coordinates phenol after the amino-acrylate E(A-A) state is reached to form a Michaelis complex (E(A-A)·S) that facilitates regioselective alkylation.

Assays with two different deuterated phenols (2-chlorophenol-d4 and 2-methylphenol-$d_8$) demonstrated clear primary kinetic isotope effects (KIEs). Not intending to be bound by theory, given that the only C—H bond that was broken is the one at C4, these KIEs indicate that deprotonation of C4—and thus, surprisingly, rearomatization of the arene—is rate limiting (FIG. 14). Said differently, deprotonation after C—C bond formation (converting from quinonoid intermediate E (Q2) to E (Q3)) is rate limiting based on observed primary KIEs. A final protonation event produces the covalently bound L-Tyr analog as an external aldimine, E($Aex_2$), FIG. 14. Not intending to be bound by theory, the hydrogen bonding arrangement to Y182 may be inferred based on the binding of 4-hydroxyquinoline over its tautomer 4-quinolone.

Reactions were performed in technical duplicate, see Table 7. KIEs measured in competition between the standard and deuterated substrate under as short of reaction times as possible to achieve 1-10% yield with minimal C—H proton exchange in the solvent. Ser reactions performed using 2-chlorophenol as the phenolic substrate; see, Example 13 for more details. While these results unambiguously identify a primary KIE for deprotonation of C4 of phenolic substrates and no primary KIE for deprotonation of Ca of Ser, they should not be used for inferring trends occurring from evolution until more rigorous methodology (e.g., not in competition and/or a more sensitive method of quantification like single-ion mode) is used.

TABLE 7

Competitive kinetic isotope effects (KIEs) Approximate KIE

| Variant | Substrate | Average | Deviation |
|---|---|---|---|
| Tm9D8* E105G | 2-chlorophenol | 1.620 | 0.088 |
| | 2-methylphenol | 1.904 | 0.014 |
| | Ser | 0.930 | 0.028 |
| Tm TyrS1 | 2-chlorophenol | 2.038 | 0.033 |
| | 2-methylphenol | 2.787 | 0.020 |
| | Ser | 0.755 | 0.012 |
| Tm TyrS2 | 2-chlorophenol | 2.371 | 0.157 |
| | 2-methylphenol | 3.638 | 0.342 |
| | Ser | 0.882 | 0.002 |
| Tm TyrS3 | 2-chlorophenol | 3.260 | 0.394 |
| | 2-methylphenol | 4.005 | 0.491 |
| | Ser | 0.874 | 0.034 |
| Tm TyrS4 | 2-chlorophenol | 2.810 | 0.022 |
| | 2-methylphenol | 3.554 | 0.587 |
| | Ser | 0.893 | 0.034 |
| Tm TyrS5 | 2-chlorophenol | 1.978 | 0.136 |
| | 2-methylphenol | 2.405 | 0.043 |
| | Ser | 0.935 | 0.039 |
| TmTyrS6 | 2-chlorophenol | 2.101 | 0.363 |
| | 2-methylphenol | 3.018 | 0.065 |
| | Ser | 0.882 | 0.010 |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

Exemplary Embodiments

Exemplary embodiments provided in accordance with the presently disclosed subject matter include, but are not limited to, the claims and the following embodiments.

Embodiment 1: An engineered tryptophan synthase β-subunit (TrpB) comprising an amino acid substitution at a position corresponding to amino acid residue E105 of SEQ ID NO: 1.

Embodiment 2: The engineered TrpB of Embodiment 1, wherein the engineered TrpB catalyzes the synthesis of a compound, wherein the compound is tyrosine or a tyrosine analog or a salt thereof.

Embodiment 3: The engineered TrpB of Embodiment 1 or 2, comprising an amino acid sequence at least 80% identical to SEQ ID NO: 1.

Embodiment 4: The engineered TrpB of Embodiment 1 or 2, comprising an amino acid sequence at least 85% identical to SEQ ID NO: 1.

Embodiment 5: The engineered TrpB of Embodiment 1 or 2, comprising an amino acid sequence at least 90% identical to SEQ ID NO: 1.

Embodiment 6: The engineered TrpB of Embodiment 1 or 2, comprising an amino acid sequence at least 95% identical to SEQ ID NO: 1.

Embodiment 7: The engineered TrpB of Embodiment 1 or 2, comprising an amino acid sequence at least 98% identical to SEQ ID NO: 1.

Embodiment 8: The engineered TrpB of any one of Embodiments 1-7, wherein the amino acid substitution at the position corresponding to amino acid residue E105 of SEQ ID NO: 1 is selected from the group consisting of glycine (G), alanine (A), serine(S), and proline (P).

Embodiment 9: The engineered TrpB of any one of Embodiments 1-8, further comprising one or more amino acid substitutions at a position corresponding to an amino acid residue selected from the group consisting of Y4, Y12, P19, E30, F41, I69, A87, K96, I103, I128, K139, P140, L147, A150, N167, L170, I174, Y181, I184, H191, L213, V227, G228, G229, S265, W286, V291, T292, S302, and R389 of SEQ ID NO: 1.

Embodiment 10: The engineered TrpB of Embodiment 9, wherein the amino acid substitution at the position corresponding to amino acid residue Y4 is N.

Embodiment 11: The engineered TrpB of Embodiment 9 or 10, wherein the amino acid substitution at the position corresponding to amino acid residue Y12 is N.

Embodiment 12: The engineered TrpB of any one of Embodiments 9-11, wherein the amino acid substitution at the position corresponding to amino acid residue P19 is G.

Embodiment 13: The engineered TrpB of any one of Embodiments 9-12, wherein the amino acid substitution at the position corresponding to amino acid residue E30 is G.

Embodiment 14: The engineered TrpB of any one of Embodiments 9-13, wherein the amino acid substitution at the position corresponding to amino acid residue F41 is Y.

Embodiment 15: The engineered TrpB of any one of Embodiments 9-14, wherein the amino acid substitution at the position corresponding to amino acid residue I69 is V.

Embodiment 16: The engineered TrpB of any one of Embodiments 9-15, wherein the amino acid substitution at the position corresponding to amino acid residue A87 is T.

Embodiment 17: The engineered TrpB of any one of Embodiments 9-16, wherein the amino acid substitution at the position corresponding to amino acid residue K96 is L.

Embodiment 18: The engineered TrpB of any one of Embodiments 9-17, wherein the amino acid substitution at the position corresponding to amino acid residue I103 is T.

Embodiment 19: The engineered TrpB of any one of Embodiments 9-18, wherein the amino acid substitution at the position corresponding to amino acid residue I128 is V.

Embodiment 20: The engineered TrpB of any one of Embodiments 9-19, wherein the amino acid substitution at the position corresponding to amino acid residue K139 is R.

Embodiment 21: The engineered TrpB of any one of Embodiments 9-20, wherein the amino acid substitution at the position corresponding to amino acid residue P140 is L.

Embodiment 22: The engineered TrpB of any one of Embodiments 9-21, wherein the amino acid substitution at the position corresponding to amino acid residue L147 is Q.

Embodiment 23: The engineered TrpB of any one of Embodiments 9-22, wherein the amino acid substitution at the position corresponding to amino acid residue A150 is V.

Embodiment 24: The engineered TrpB of any one of Embodiments 9-23, wherein the amino acid substitution at the position corresponding to amino acid residue N167 is D.

Embodiment 25: The engineered TrpB of any one of Embodiments 9-24, wherein the amino acid substitution at the position corresponding to amino acid residue L170 is F.

Embodiment 26: The engineered TrpB of any one of Embodiments 9-25, wherein the amino acid substitution at the position corresponding to amino acid residue I174 is T.

Embodiment 27: The engineered TrpB of any one of Embodiments 9-26, wherein the amino acid substitution at the position corresponding to amino acid residue Y181 is H.

Embodiment 28: The engineered TrpB of any one of Embodiments 9-27, wherein the amino acid substitution at the position corresponding to amino acid residue I184 is F, P, or A.

Embodiment 29: The engineered TrpB of any one of Embodiments 9-28, wherein the amino acid substitution at the position corresponding to amino acid residue H191 is Y.

Embodiment 30: The engineered TrpB of any one of Embodiments 9-29, wherein the amino acid substitution at the position corresponding to amino acid residue L213 is P.

Embodiment 31: The engineered TrpB of any one of Embodiments 9-30, wherein the amino acid substitution at the position corresponding to amino acid residue V227 is M.

Embodiment 32: The engineered TrpB of any one of Embodiments 9-31, wherein the amino acid substitution at the position corresponding to amino acid residue G228 is S.

Embodiment 33: The engineered TrpB of any one of Embodiments 9-32, wherein the amino acid substitution at the position corresponding to amino acid residue G229 is A.

Embodiment 34: The engineered TrpB of any one of Embodiments 9-33, wherein the amino acid substitution at the position corresponding to amino acid residue S265 is P.

Embodiment 35: The engineered TrpB of any one of Embodiments 9-34, wherein the amino acid substitution at the position corresponding to amino acid residue W286 is G.

Embodiment 36: The engineered TrpB of any one of Embodiments 9-35, wherein the amino acid substitution at the position corresponding to amino acid residue V291 is A.

Embodiment 37: The engineered TrpB of any one of Embodiments 9-36, wherein the amino acid substitution at the position corresponding to amino acid residue T292 is S.

Embodiment 38: The engineered TrpB of any one of Embodiments 9-37, wherein the amino acid substitution at the position corresponding to amino acid residue S302 is P.

Embodiment 39: The engineered TrpB of any one of Embodiments 9-38, wherein the amino acid substitution at the position corresponding to amino acid residue R389 is H.

Embodiment 40: The engineered TrpB of Embodiment 2, wherein the compound is at least 95% regioselective for para alkylation.

Embodiment 41: The engineered TrpB of Embodiment 2, wherein the compound is at least 99% regioselective for para alkylation.

Embodiment 42: The engineered TrpB of Embodiment 2, wherein the tyrosine is L-tyrosine.

Embodiment 43: The engineered TrpB of Embodiment 2, wherein the tyrosine analog is selected from the group consisting of 2-amino-3-(4-hydroxy-3-(methylthio)phenyl) propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl) propanoic acid, 2-amino-3-(3-fluoro-4-hydroxyphenyl) propanoic acid, 2-amino-3-(4-hydroxy-3-methoxyphenyl) propanoic acid, 2-amino-3-(3-bromo-4-hydroxyphenyl) propanoic acid, 2-amino-3-(3,5-dichloro-4-hydroxyphenyl) propanoic acid, 2-amino-3-(4-hydroxy-3,5-dimethylphenyl) propanoic acid, 2-amino-3-(2-fluoro-4-hydroxyphenyl) propanoic acid, 2-amino-3-(2-chloro-4-hydroxyphenyl) propanoic acid, 2-amino-3-(4-hydroxy-2-methylphenyl) propanoic acid, 2-amino-3-(2,3,5,6-tetrafluoro-4-hydroxyphenyl)propanoic acid, and 2-amino-3-(4-hydroxynaphthalen-1-yl)butanoic acid.

Embodiment 44: An engineered tryptophan synthase β-subunit (TrpB) comprising the amino acid sequence of any one of SEQ ID NOS: 4-11.

Embodiment 45: An isolated polynucleotide comprising a nucleotide sequence encoding the engineered TrpB of Embodiment 44.

Embodiment 46: A method for preparing a compound with the engineered TrpB of any one of Embodiments 1-31, wherein the compound is tyrosine or a tyrosine analog or a salt thereof, the method comprising combining: (i) a first substrate; (ii) a second substrate; and (iii) the engineered TrpB in a reaction mixture; and maintaining the reaction mixture under conditions sufficient to form the compound.

Embodiment 47: The method of Embodiment 46, wherein the first substrate is a donor amino acid.

Embodiment 48: The method of Embodiment 47, wherein the donor amino acid is a β-hydroxy amino acid.

Embodiment 49: The method of Embodiment 48, wherein the β-hydroxy amino acid is threonine or serine.

Embodiment 50: The method of Embodiment 48, wherein the β-hydroxy amino acid is L-threonine.

Embodiment 51: The method of Embodiment 48, wherein the β-hydroxy amino acid is L-serine.

Embodiment 52: The method of Embodiment 47, wherein the donor amino acid is β-chloroalanine.

Embodiment 53: The method of Embodiment 47, wherein the donor amino acid is S-(o-nitrophenyl)-L-cysteine.

Embodiment 54: The method of Embodiment 46, wherein the second substrate is phenol or a phenol analog.

Embodiment 55: The method of Embodiment 46, wherein the tyrosine is L-tyrosine.

Embodiment 56: The method of Embodiment 46, wherein the tyrosine analog is selected from the group consisting of 2-amino-3-(4-hydroxy-3-(methylthio)phenyl)propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl)propanoic acid, 2-amino-3-(3-fluoro-4-hydroxyphenyl)propanoic acid, 2-amino-3-(4-hydroxy-3-methoxyphenyl)propanoic acid, 2-amino-3-(3-bromo-4-hydroxyphenyl)propanoic acid, 2-amino-3-(3,5-dichloro-4-hydroxyphenyl)propanoic acid, 2-amino-3-(4-hydroxy-3,5-dimethylphenyl)propanoic acid, 2-amino-3-(2-fluoro-4-hydroxyphenyl)propanoic acid, 2-amino-3-(2-chloro-4-hydroxyphenyl)propanoic acid, 2-amino-3-(4-hydroxy-2-methylphenyl)propanoic acid, 2-amino-3-(2,3,5,6-tetrafluoro-4-hydroxyphenyl)propanoic acid, and 2-amino-3-(4-hydroxynaphthalen-1-yl)butanoic acid.

Embodiment 57: The method of any one of Embodiments 54, wherein the phenol analog is selected from the group consisting of 2-(methylthio) phenol, 2-iodophenol, 2-chlorophenol, o-cresol, 2-fluorophenol, 2-bromophenol, 2-methoxyphenol, 2,6-dichlorophenol, 3-fluorophenol, 3-chlorophenol, m-cresol, 2,3,5,6-tetrafluorophenol, naphthalen-1-ol, and 2,6-dimethylphenol.

Embodiment 58: A method of preparing a compound of Formula I:

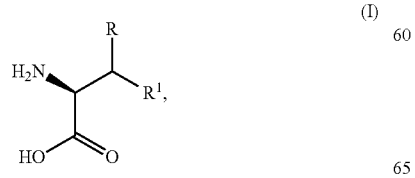

or a salt thereof, wherein R is (A), (B), or (C):

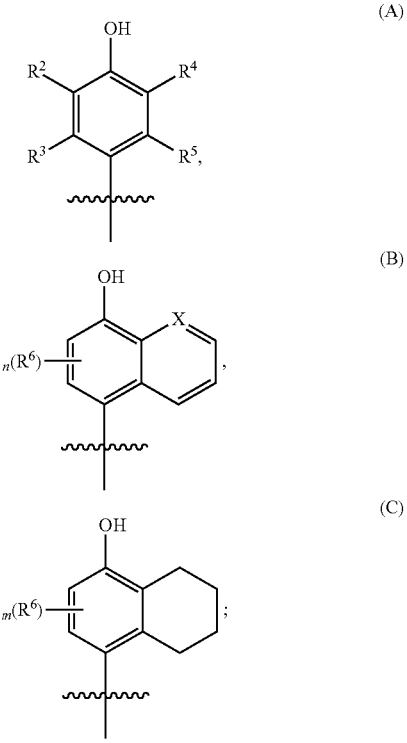

the method comprising:

combining: (i) a β-hydroxy amino acid; (ii) phenol or a phenol analog; and (iii) the engineered TrpB of any one of Embodiments 1-31 in a reaction mixture; and maintaining the reaction mixture under conditions sufficient to form the compound according to Formula I;

wherein:

$R^1$ is hydrogen or $C_{1-8}$ alkyl, which is optionally substituted with one or more $R^{1a}$; each $R^{1a}$ is independently selected from the group consisting of hydrogen, halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N($R^{1b}$)$_2$, —C(O)$R^{1c}$, —C(O)N($R^{1b}$)$_2$, —$NR^{1b}$C(O)$R^{1c}$, and —OC(O)$R^{1c}$;

each $R^{1b}$ is independently selected from the group consisting of hydrogen and $C_{1-6}$ alkyl;

each $R^{1c}$ is independently selected from the group consisting of hydrogen, —OH, halogen, $C_{1-6}$ alkyl, $C_{1-6}$ alkoxy;

$R^2$, $R^3$, $R^4$, and $R^5$ are independently selected from the group consisting of hydrogen, halogen, $C_{1-8}$ alkyl, which is optionally substituted with one or more $R^{2a}$;

each $R^{2a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{2b}$)$_2$, —C(O)$R^{2c}$, —C(O)N($R^{2b}$)$_2$, —$NR^{2b}$C(O)$R^{2c}$, and —OC(O)$R^{2c}$;

each $R^{2b}$ is independently selected from the group consisting of hydrogen and $C_{1-6}$ alkyl;

each $R^{2c}$ is independently selected from the group consisting of hydrogen, —OH, halogen, $C_{1-6}$ alkyl, $C_{1-6}$ alkoxy;

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and C$_{1-6}$ alkyl;

each $R^{3c}$ is independently selected from the group consisting of hydrogen, —OH, halogen, C$_{1-6}$ alkyl, C$_{1-6}$ alkoxy;

n is selected from 0, 1, 2, 3, 4, or 5;

m is selected from 0, 1, 2, 3, 4, 5, or 6;

X is —C(R$^7$) or —N;

wherein R$^7$ is hydrogen or C$_{1-8}$ alkyl, which is optionally substituted with one or more $R^{4a}$;

each $R^{4a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^4$;

each $R^{4b}$ is independently selected from the group consisting of hydrogen and C$_{1-6}$ alkyl; and each R$^4$ is independently selected from the group consisting of hydrogen, —OH, halogen, C$_{1-6}$ alkyl, C$_{1-6}$ alkoxy.

Embodiment 59: The method of Embodiment 58, wherein the engineered TrpB is a thermophilic TrpB.

Embodiment 60: The method of Embodiment 59, wherein the thermophilic TrpB is selected from the group consisting of *T. maritima* TrpB, a *P. furiosis* TrpB, an *A. fulgidus* Trp. B, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T. thermophilus* TrpB, a *P. abyssi* TrpB, an *M. jannaschii* TrpB, a *T. kodakarensis* TrpB, and an *M. aeolicus* TrpB.

Embodiment 61: The method of any one of Embodiments 58-60, wherein the reaction mixture is maintained at a temperature ranging from about 20° C. to about 80° C.

Embodiment 62: The method of any one of Embodiments 58-61, wherein R$^1$ is hydrogen.

Embodiment 63: The method of any one of Embodiments 58-61, wherein R$^1$ is C$_{1-8}$ alkyl.

Embodiment 64: A method of preparing a compound of Formula II:

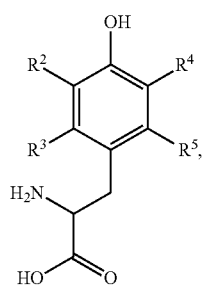

(II)

or a salt thereof, the method comprising:

combining: (i) a β-hydroxy amino acid; (ii) phenol or a phenol analog; and (iii) the engineered TrpB of any one of Embodiments 1-31 in a reaction mixture; and maintaining the reaction mixture under conditions sufficient to form the compound according to Formula II;

wherein:

R$^2$, R$^3$, R$^4$, and R$^5$ are independently selected from the group consisting of hydrogen, halogen, C$_{1-8}$ alkyl, which is optionally substituted with one or more $R^{2a}$;

each $R^{2a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{2b}$)$_2$, —C(O)R$^{2c}$, —C(O)N(R$^{2b}$)$_2$, —NR$^{2b}$C(O)R$^{2c}$, and —OC(O)R$^{2c}$;

each $R^{2b}$ is independently selected from the group consisting of hydrogen and C$_{1-6}$ alkyl; and each $R^{2c}$ is independently selected from the group consisting of hydrogen, —OH, halogen, C$_{1-6}$ alkyl, C$_{1-6}$ alkoxy.

Embodiment 65: The method of Embodiment 64, wherein the engineered TrpB is a thermophilic TrpB.

Embodiment 66: The method of Embodiment 65, wherein the thermophilic TrpB is selected from the group consisting of *T. maritima* TrpB, a *P. furiosis* TrpB, an *A. fulgidus* Trp. B, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T. thermophilus* TrpB, a *P. abyssi* TrpB, an *M. jannaschii* TrpB, a *T. kodakarensis* TrpB, and an *M. deolicus* TrpB.

Embodiment 67: The method of any one of Embodiments 64-66, wherein the reaction mixture is maintained at a temperature ranging from about 20° C. to about 50° C.

Embodiment 68: A method of preparing a compound of Formula III:

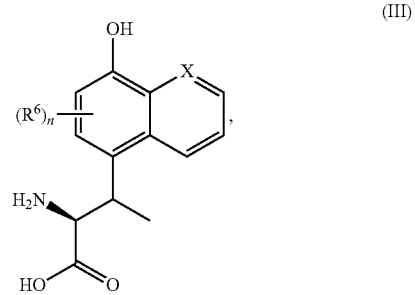

(III)

or a salt thereof, the method comprising:

combining: (i) a β-hydroxy amino acid; (ii) phenol or a phenol analog; and (iii) the engineered TrpB of any one of Embodiments 1-31 in a reaction mixture; and maintaining the reaction mixture under conditions sufficient to form the compound according to Formula III;

wherein:

R$^6$ is hydrogen or C$_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, C$_{1-12}$ alkyl, C$_{2-12}$ alkenyl, C$_{1-12}$ alkynyl, C$_{1-12}$ alkoxy, C$_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and C$_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C($R^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{4b}$)$_2$, —C(O)$R^{4c}$, —C(O)N($R^{4b}$)$_2$, —N$R^{4b}$C(O)$R^{4c}$, and —OC(O)$R^{4c}$;

each $R^{4b}$ is independently selected from the group consisting of hydrogen and $C_{1-6}$ alkyl; and each $R^4$ is independently selected from the group consisting of hydrogen, —OH, halogen, $C_{1-6}$ alkyl, $C_{1-6}$ alkoxy.

Embodiment 69: The method of Embodiment 68, wherein the engineered TrpB is a thermophilic TrpB.

Embodiment 70: The method of Embodiment 69, wherein the thermophilic TrpB is selected from the group consisting of *T. maritima* TrpB, a *P. furiosis* TrpB, an *A. fulgidus* Trp. B, a *T. naphthophila* TrpB, a *T. petrophila* TrpB, a *T. neapolitana* TrpB, a *C. subterraneus* TrpB, a *D. tunisiensi* TrpB, a *D. kuznetsovii* TrpB, a *P. mobilis* TrpB, an *A. aeolicus* TrpB, an *S. azorense* TrpB, a *T. pseudethanolicus* TrpB, a *T. thermophilus* TrpB, a *P. abyssi* TrpB, an *M. jannaschii* TrpB, a *T. kodakarensis* TrpB, and an *M. aeolicus* TrpB.

Embodiment 71: The method of any one of Embodiments 68-70, wherein the reaction mixture is maintained at a temperature ranging from about 20° C. to about 50° C.

Embodiment 72: The method of any one of Embodiments 64-67, wherein the compound has a structure selected from the group consisting of:

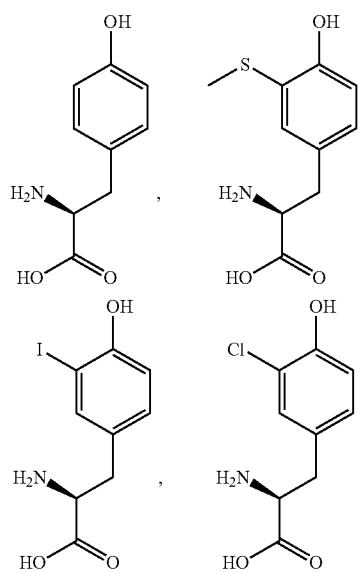

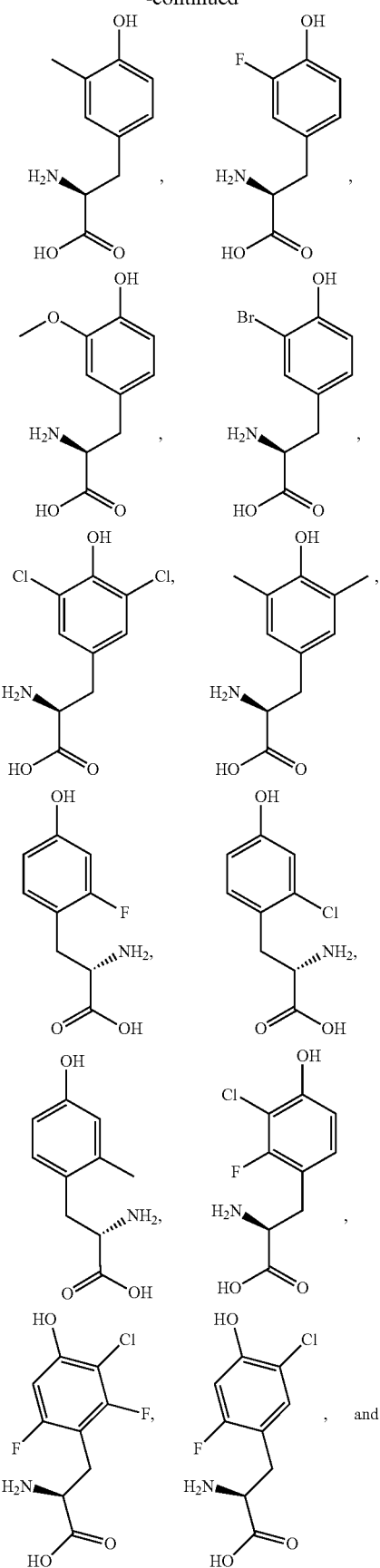

-continued

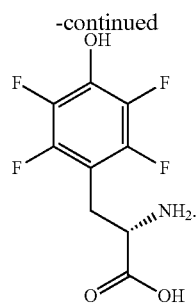

Embodiment 73: The method of any one of Embodiments 68-71, wherein the compound has the structure:

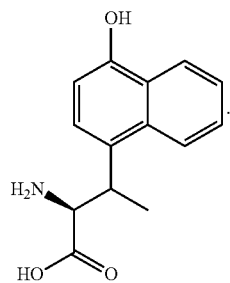 [SMILES: CC(c1ccc(O)c2ccccc12)[C@H](N)C(=O)O]

Embodiment 74: A compound of Formula I:

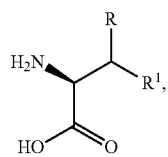
(I)

or a salt thereof, wherein:
R is (B) or (C):

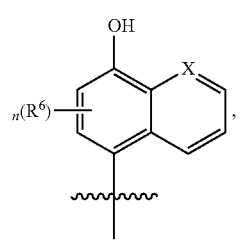
(B)

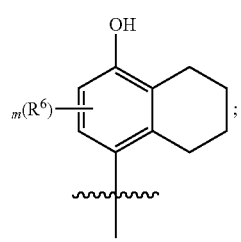
(C)

$R^1$ is hydrogen or $C_{1-8}$ alkyl, which is optionally substituted with one or more $R^{1a}$;

each $R^{1a}$ is independently selected from the group consisting of hydrogen, halogen, —OH, —CN, —N$_3$, —NO$_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —N(R$^{1b}$)$_2$, —C(O)R$^{1c}$, —C(O)N(R$^{1b}$)$_2$, —NR$^{1b}$C(O)R$^{1c}$, and —OC(O)R$^{1c}$;

each $R^{1b}$ is independently selected from the group consisting of hydrogen and $C_{1-6}$ alkyl;

each $R^{1c}$ is independently selected from the group consisting of hydrogen, —OH, halogen, $C_{1-6}$ alkyl, $C_{1-6}$ alkoxy;

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;

n is selected from 0, 1, 2, 3, 4, or 5;

m is selected from 0, 1, 2, 3, 4, 5, or 6;

X is —C(R$^7$) or —N;

wherein $R^7$ is hydrogen or $C_{1-8}$ alkyl, which is optionally substituted with one or more $R^{4a}$;

each $R^{4a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{4b}$)$_2$, —C(O)R$^{4c}$, —C(O)N(R$^{4b}$)$_2$, —NR$^{4b}$C(O)R$^{4c}$, and —OC(O)R$^{4c}$;

each $R^{4b}$ is independently selected from the group consisting of hydrogen and $C_{1-6}$ alkyl; and each $R^4$ is independently selected from the group consisting of hydrogen, —OH, halogen, $C_{1-6}$ alkyl, $C_{1-6}$ alkoxy.

Embodiment 75: A compound of Formula III:

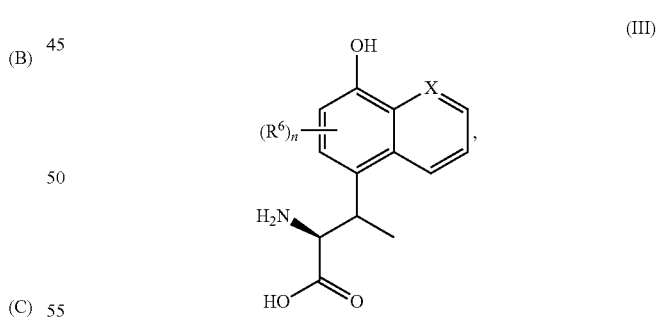
(III)

or a salt thereof, wherein:

$R^6$ is hydrogen or $C_{1-8}$ alkyl, which is optionally substituted with one or more $R^{3a}$;

each $R^{3a}$ is independently selected from the group consisting of hydrogen, halogen, —OH, —CN, —N$_3$, —NO$_2$, $C_{1-12}$ alkyl, $C_{2-12}$ alkenyl, $C_{1-12}$ alkynyl, $C_{1-12}$ alkoxy, $C_{1-12}$ thioalkoxy, —N(R$^{3b}$)$_2$, —C(O)R$^{3c}$, —C(O)N(R$^{3b}$)$_2$, —NR$^{3b}$C(O)R$^{3c}$, and —OC(O)R$^{3c}$;

each $R^{3b}$ is independently selected from the group consisting of hydrogen and $C_{1-6}$ alkyl;

each $R^{3c}$ is independently selected from the group consisting of hydrogen, —OH, halogen, $C_{1-6}$ alkyl, $C_{1-6}$ alkoxy;
n is selected from 0, 1, 2, 3, 4, or 5;
m is selected from 0, 1, 2, 3, 4, 5, or 6;
X is —C($R^7$) or —N;
wherein $R^7$ is hydrogen or $C_{1-8}$ alkyl, which is optionally substituted with one or more $R^{4a}$;
each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —N($R^{4b}$)$_2$, —C(O)$R^{4c}$, —C(O)N($R^{4b}$)$_2$, —N$R^{4b}$C(O)$R^{4c}$, and —OC(O)$R^{4c}$;
each $R^{4b}$ is independently selected from the group consisting of hydrogen and $C_{1-6}$ alkyl; and
each $R^4$ is independently selected from the group consisting of hydrogen, —OH, halogen, $C_{1-6}$ alkyl, $C_{1-6}$ alkoxy.

Embodiment 76: The compound of Embodiment 75, wherein the compound has the structure:

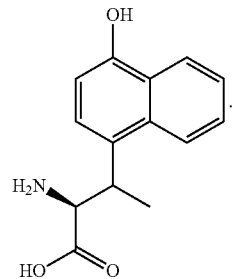 [SMILES: CC(c1ccc(O)c2ccccc12)[C@H](N)C(=O)O]

INFORMAL SEQUENCE LISTING

```
SEQ ID NO: 1 (T. maritima TrpB)
MKGYFGPYGGQYVPEILMPALEELEAAYEEIMKDESFWKEFNDLLRDYAGRPTPLYFA
RRLSEKYGARIYLKREDLLHTGAHKINNAIGQVLLAKKMGKTRIIAETGAGQHGVATAT
AAAALFGMECVIYMGEEDTIRQKPNVERMKLLGAKVVPVKSGSRTLKDAINEALRDWIT
NLQTTYYVIGSVVGPHPYPIIVRNFQKVIGEETKKQILEKEGRLPDYIVACVGGGSNAAGI
FYPFIDSGVKLIGVEAGGEGLETGKHAASLLKGKIGYLHGSKTFVLQDDWGQVQVTHSV
SAGLDYSGVGPEHAYWRETGKVLYDAVTDEEALDAFIELSRLEGIIPALESSHALAYLK
KINIKGKVVVVNLSGRGDKDLESVLNHPYVRERIRLE SEQ ID NO: 2 (Tm9D8)
MKGYFGPYGGQYVPEILMGALEELEAAYEGIMKDESFWKEFNDLLRDYAGRPTPLYFA
RRLSEKYGARVYLKREDLLHTGAHKINNAIGQVLLAKLMGKTRIIAETGAGQHGVATA
TAAALFGMECVIYMGEEDTIRQKLNVERMKLLGAKVVPVKSGSRTLKDAIDEALRDWI
TNLQTTYYVIGSVVGPHPYPIIVRNFQKVIGEETKKQIPEKEGRLPDYIVACVSGGSNAAG
IFYPFIDSGVKLIGVEAGGEGLETGKHAASLLKGKIGYLHGSKTFVLQDDWGQVQVSHS
VSAGLDYSGVGPEHAYWRETGKVLYDAVTDEEALDAFIELSRLEGIIPALESSHALAYL
KKINIKGKVVVVNLSGRGDKDLESVLNHPYVRERIRLE SEQ ID NO: 3 (Tm9D8*)
MKGYFGPYGGQYVPEILMGALEELEAAYEGIMKDESFWKEFNDLLRDYAGRPTPLYFA
RRLSEKYGARVYLKREDLLHTGAHKINNAIGQVLLAKLMGKTRIIAETGAGQHGVATA
TAAALFGMECVIYMGEEDTIRQKLNVERMKLLGAKVVPVKSGSRTLKDAIDEALRDWI
TNLQTTYYVFGSVVGPHPYPIIVRNFQKVIGEETKKQIPEKEGRLPDYIVACVSGGSNAA
GIFYPFIDSGVKLIGVEAGGEGLETGKHAASLLKGKIGYLHGSKTFVLQDDWGQVQVSH
SVSAGLDYSGVGPEHAYWRETGKVLYDAVTDEEALDAFIELSRLEGIIPALESSHALAYL
KKINIKGKVVVVNLSGRGDKDLESVLNHPYVRERIRLE SEQ ID NO: 4 (Tm9D8* E105G)
MKGYFGPYGGQYVPEILMGALEELEAAYEGIMKDESFWKEFNDLLRDYAGRPTPLYFA
RRLSEKYGARVYLKREDLLHTGAHKINNAIGQVLLAKLMGKTRIIAGTGAGQHGVATA
TAAALFGMECVIYMGEEDTIRQKLNVERMKLLGAKVVPVKSGSRTLKDAIDEALRDWI
TNLQTTYYVFGSVVGPHPYPIIVRNFQKVIGEETKKQIPEKEGRLPDYIVACVSGGSNAA
GIFYPFIDSGVKLIGVEAGGEGLETGKHAASLLKGKIGYLHGSKTFVLQDDWGQVQVSH
SVSAGLDYSGVGPEHAYWRETGKVLYDAVTDEEALDAFIELSRLEGIIPALESSHALAYL
KKINIKGKVVVVNLSGRGDKDLESVLNHPYVRERIRLE SEQ ID NO: 5 (Tm9D8* E105G F184P)
MKGYFGPYGGQYVPEILMGALEELEAAYEGIMKDESFWKEFNDLLRDYAGRPTPLYFA
RRLSEKYGARVYLKREDLLHTGAHKINNAIGQVLLAKLMGKTRIIAGTGAGQHGVATA
TAAALFGMECVIYMGEEDTIRQKLNVERMKLLGAKVVPVKSGSRTLKDAIDEALRDWI
TNLQTTYYVPGSVVGPHPYPIIVRNFQKVIGEETKKQIPEKEGRLPDYIVACVSGGSNAA
GIFYPFIDSGVKLIGVEAGGEGLETGKHAASLLKGKIGYLHGSKTFVLQDDWGQVQVSH
SVSAGLDYSGVGPEHAYWRETGKVLYDAVTDEEALDAFIELSRLEGIIPALESSHALAYL
KKINIKGKVVVVNLSGRGDKDLESVLNHPYVRERIRLE SEQ ID NO: 6 (TmTyrS1)
MKGNFGPYGGQNVPEILMGALEELEAAYEGIMKDESFWKEYNDLLRDYAGRPTPLYFA
RRLSEKYGARVYLKREDLLHTGAHKINNAIGQVLLAKLMGKTRITAGTGAGQHGVATA
TAAALFGMECVIYMGEEDTIRQKLNVERMKLLGAKVVPVKSGSRTLKDAIDEALRDWI
TNLQTTYYVPGSVVGPHPYPIIVRNFQKVIGEETKKQIPEKEGRLPDYIVACVSGGSNAA
GIFYPFIDSGVKLIGVEAGGEGLETGKHAASLLKGKIGYLHGSKTFVLQDDWGQVQASH
SVSAGLDYPGVGPEHAYWRETGKVLYDAVTDEEALDAFIELSRLEGIIPALESSHALAYL
KKINIKGKVVVVNLSGRGDKDLESVLNHPYVRERIHLE
```

INFORMAL SEQUENCE LISTING

SEQ ID NO: 7 (TmTyrS2)
MKGNFGPYGGQNVPEILMGALEELEAAYEGIMKDESFWKEYNDLLRDYAGRPTPLYFA
RRLSEKYGARVYLKREDLLHTGAHKINNTIGQVLLAKLMGKTRITAGTGAGQHGVATA
TAAALFGMECVVYMGEEDTIRQKLNVERMKLLGAKVVPVKSGSRTLKDAIDEALRDWI
TNLQTTYYVPGSVVGPYPYPIIVRNFQKVIGEETKKQIPEKEGRLPDYIVACVSGGSNAA
GIFYPFIDSGVKLIGVEAGGEGLETGKHAASLLKGKIGYLHGSKTFVLQDDWGQVQASH
SVSAGLDYPGVGPEHAYWRETGKVLYDAVTDEEALDAFIELSRLEGIIPALESSHALAYL
KKINIKGKVVVVNLSGRGDKDLESVLNHPYVRERIHLE

SEQ ID NO: 8 (TmTyrS3)
MKGNFGPYGGQNVPEILMGALEELEAAYEGIMKDESFWKEYNDLLRDYAGRPTPLYFA
RRLSEKYGARVYLKREDLLHTGAHKINNTIGQVLLAKLMGKTRITAGTGAGQHGVATA
TAAALFGMECVVYMGEEDTIRQKLNVERMKQLGAKVVPVKSGSRTLKDAIDEALRDW
ITNLQTTYYVPGSVVGPYPYPIIVRNFQKVIGEETKKQIPEKEGRLPDYIVACMSGGSNAA
GIFYPFIDSGVKLIGVEAGGEGLETGKHAASLLKGKIGYLHGSKTFVLQDDWGQVQASH
SVSAGLDYPGVGPEHAYWRETGKVLYDAVTDEEALDAFIELSRLEGIIPALESSHALAYL
KKINIKGKVVVVNLSGRGDKDLESVLNHPYVRERIHLE

SEQ ID NO: 9 (TmTyrS4)
MKGNFGPYGGQNVPEILMGALEELEAAYEGIMKDESFWKEYNDLLRDYAGRPTPLYFA
RRLSEKYGARVYLKREDLLHTGAHKINNTIGQVLLAKLMGKTRITAGTGAGQHGVATA
TAAALFGMECVVYMGEEDTIRQKLNVERMKQLGAKVVPVKSGSRTLKDAIDEALRDW
TTNLQTTYYVAGSVVGPYPYPIIVRNFQKVIGEETKKQIPEKEGRLPDYIVACMSGGSNA
AGIFYPFIDSGVKLIGVEAGGEGLETGKHAAPLLKGKIGYLHGSKTFVLQDDWGQVQAS
HSVSAGLDYPGVGPEHAYWRETGKVLYDAVTDEEALDAFIELSRLEGIIPALESSHALAY
LKKINIKGKVVVVNLSGRGDKDLESVLNHPYVRERIHLE

SEQ ID NO: 10 (TmTyrS5)
MKGNFGPYGGQNVPEILMGALEELEAAYEGIMKDESFWKEYNDLLRDYAGRPTPLYFA
RRLSEKYGARVYLKREDLLHTGAHKINNTIGQVLLAKLMGKTRITAGTGAGQHGVATA
TAAALFGMECVVYMGEEDTIRQKLNVERMKQLGVKVVPVKSGSRTLKDAIDEALRDW
TTNLQTTHYVAGSVVGPYPYPIIVRNFQKVIGEETKKQIPEKEGRLPDYIVACMSAGSNA
AGIFYPFIDSGVKLIGVEAGGEGLETGKHAASLLKGKIGYLHGSKTFVLQDDWGQVQAS
HSVSAGLDYPGVGPEHAYWRETGKVLYDAVTDEEALDAFIELSRLEGIIPALESSHALAY
LKKINIKGKVVVVNLSGRGDKDLESVLNHPYVRERIHLE

SEQ ID NO: 11 (TmTyrS6)
MKGNFGPYGGQNVPEILMGALEELEAAYEGIMKDESFWKEYNDLLRDYAGRPTPLYFA
RRLSEKYGARVYLKREDLLHTGAHKINNTIGQVLLAKLMGKTRITAGTGAGQHGVATA
TAAALFGMECVVYMGEEDTIRQRLNVERMKQLGVKVVPVKSGSRTLKDAIDEAFRDW
TTNLQTTHYVAGSVVGPYPYPIIVRNFQKVIGEETKKQIPEKEGRLPDYIVACMSAGSNA
AGIFYPFIDSGVKLIGVEAGGEGLETGKHAASLLKGKIGYLHGSKTFVLQDDGGQVQAS
HSVSAGLDYPGVGPEHAYWRETGKVLYDAVTDEEALDAFIELSRLEGIIPALESSHALAY
LKKINIKGKVVVVNLSGRGDKDLESVLNHPYVRERIHLE

SEQ ID NO: 12 (Pf2B9)
MWFGEFGGQYVPETLVGPLKELEKAYKRFKDDEEFNRQLNYYLKTWAGRPTPLYYAK
RLTEKIGGAKVYLKREDLVHGGAHKTNNAIGQALLAKLMGKTRLIAETGAGQHGVAT
AMAGALLGMKVDIYMGAEDVERQKMNVFRMKLLGANVIPVNSGSRTLKDAINEALRD
WVATFEYTHYLIGSVVGPHPYPTIVRDFQSVIGREAKAQILEAEGQLPDVIVACVGGGSN
AMGIFYPFVNDKKVKLVGVEAGGKGLESGKHSASLNAGQVGVSHGMLSYFLQDEEGQI
KPSHSIAPGLDYPGVGPEHAYLKKIQRAEYVAVTDEEALKAFHELSRTEGIIPALESAHA
VAYAMKLAKEMSRDEIIIVNLSGRGDKDLDIVLKASGNVLE

SEQ ID NO: 13 (Pf2B9 E104G)
MWFGEFGGQYVPETLVGPLKELEKAYKRFKDDEEFNRQLNYYLKTWAGRPTPLYYAK
RLTEKIGGAKVYLKREDLVHGGAHKTNNAIGQALLAKLMGKTRLIAGTGAGQHGVAT
AMAGALLGMKVDIYMGAEDVERQKMNVFRMKLLGANVIPVNSGSRTLKDAINEALRD
WVATFEYTHYLIGSVVGPHPYPTIVRDFQSVIGREAKAQILEAEGQLPDVIVACVGGGSN
AMGIFYPFVNDKKVKLVGVEAGGKGLESGKHSASLNAGQVGVSHGMLSYFLQDEEGQI
KPSHSIAPGLDYPGVGPEHAYLKKIQRAEYVAVTDEEALKAFHELSRTEGIIPALESAHA
VAYAMKLAKEMSRDEIIIVNLSGRGDKDLDIVLKASGNVLE

SEQ ID NO: 14 UniProt Reference ID: F4K727_ARATH (Exemplary TrpB A105)
MSSSKIQVRGQPLLRVPARNHRMTHLVVCGVSTKRHHREINALSSNSGPSLDSVPTRTD
KRQFLRGDGNGKFGRFGGKFVPETLMSRLIELEDEFNFVRCDHEFQEELTTALRDYVGR
ETPLYFAERLTEHYKNIVPTIEGGPEIYLKREDLSHCGSHKINNALAQAMISRRLGCSRVV
AATGAGQHGVATAAACAKLSLECTVFMGAADIEKQSFNVLSMKLLGAQVISVEGTFKD
ASSEAIRNWVENLYTTYYLSGTVVGPHPCPIIVREFQSVIGKETRRQAKQLWGGKPDVL
VACVGSGSNALGLFHEFVGDEDVRLVGVEAAGLGLDSGKHSATLAFGDVGVYHGSMS
YLLQDDQGQILKPHSVGVGLEYPGVGPEISFMKETGRAEFYTATDEEAIQACMRLSRLE
GIIPALEASHALAFLDKLVPTLRDGAKVVVNCSGRGDKDLDTLIQRGMPSSFC SEQ ID NO: 15 UniProt Reference ID: A0A059W1L0_STRA9 (Exemplary TrpB G105)
MMNSAEASLTAEEIVPTHWYNVLSDLSGVEDAAKLRQARPETRTDGDAVAPQIPLSMY
RQSMGRERFVEIPQEVRAEYLRWRPTPLKRARRLEQLLDTPARIYYKYEGTNTTGSHKL
NTALAQAYYYKQAGITSLTTGTGAGQWGSALAVACRIFGLECTVYMVRVSYDQKPYR -continued

INFORMAL SEQUENCE LISTING

```
RIMMEMNGAKVISSPNENSEAGRAALARDPNTDGSLSIANAEAFEHARQVERCNLSVGS
GENHVLLHQTVIGQEAVRQFRAIGDFPDVVIGSVGAGSNFSGVSLPFFHEKVREGLDTRF
VAVEPEACPKLTKGRYAWDYNDYTGITPMTKMYTLGHTFVSPGIHAGGLRYHGAAPLV
SAMYHQKLIEAVAYPQRSVFEAGITFAHEEGLIPAPESAHAIRGAIEEALLAKKEGREKVI
LFNLSGHGLLDLSAYQQFLSGNMTDMAASDEAIAASLGRLPAMDDLGAAAH
```

What is claimed is:

1. An engineered tryptophan synthase β-subunit (TrpB) comprising an amino acid substitution at a position corresponding to amino acid residue E105 of SEQ ID NO: 1, wherein the engineered TrpB catalyzes the synthesis of a tyrosine, a tyrosine analog, or a salt thereof.

2. The engineered TrpB of claim 1, comprising an amino acid sequence at least 80% identical to SEQ ID NO: 1.

3. The engineered TrpB of claim 1, wherein the amino acid substitution at the position corresponding to amino acid residue E105 of SEQ ID NO: 1 is selected from the group consisting of glycine (G), alanine (A), serine(S), and proline (P).

4. The engineered TrpB of claim 1, further comprising one or more amino acid substitutions at a position corresponding to an amino acid residue selected from the group consisting of Y4, Y12, P19, E30, F41, I69, A87, K96, I103, I128, K139, P140, L147, A150, N167, L170, I174, Y181, I184, H191, L213, V227, G228, G229, S265, W286, V291, T292, S302, and R389 of SEQ ID NO: 1.

5. The engineered TrpB of claim 4, wherein:
the amino acid substitution at the position corresponding to amino acid residue Y4 is N;
the amino acid substitution at the position corresponding to amino acid residue Y12 is N;
the amino acid substitution at the position corresponding to amino acid residue P19 is G;
the amino acid substitution at the position corresponding to amino acid residue E30 is G;
the amino acid substitution at the position corresponding to amino acid residue F41 is Y;
the amino acid substitution at the position corresponding to amino acid residue I69 is V;
the amino acid substitution at the position corresponding to amino acid residue A87 is T;
the amino acid substitution at the position corresponding to amino acid residue K96 is L;
the amino acid substitution at the position corresponding to amino acid residue I103 is T;
the amino acid substitution at the position corresponding to amino acid residue I128 is V;

the amino acid substitution at the position corresponding to amino acid residue K139 is R;
the amino acid substitution at the position corresponding to amino acid residue P140 is L;
the amino acid substitution at the position corresponding to amino acid residue L147 is Q;
the amino acid substitution at the position corresponding to amino acid residue A150 is V;
the amino acid substitution at the position corresponding to amino acid residue N167 is D;
the amino acid substitution at the position corresponding to amino acid residue L170 is F;
the amino acid substitution at the position corresponding to amino acid residue I174 is T;
the amino acid substitution at the position corresponding to amino acid residue Y181 is H;
the amino acid substitution at the position corresponding to amino acid residue I184 is F, P, or A;
the amino acid substitution at the position corresponding to amino acid residue H191 is Y;
the amino acid substitution at the position corresponding to amino acid residue L213 is P;
the amino acid substitution at the position corresponding to amino acid residue V227 is M;
the amino acid substitution at the position corresponding to amino acid residue G228 is S;
the amino acid substitution at the position corresponding to amino acid residue G229 is A;
the amino acid substitution at the position corresponding to amino acid residue S265 is P;
the amino acid substitution at the position corresponding to amino acid residue W286 is G;
the amino acid substitution at the position corresponding to amino acid residue V291 is A;
the amino acid substitution at the position corresponding to amino acid residue T292 is S;
the amino acid substitution at the position corresponding to amino acid residue S302 is P; or
the amino acid substitution at the position corresponding to amino acid residue R389 is H.

6. The engineered TrpB of claim 1, wherein the compound is at least 95% regioselective for para alkylation.

7. The engineered TrpB of claim 1, wherein the tyrosine is L-tyrosine and the tyrosine analog is selected from the group consisting of 2-amino-3-(4-hydroxy-3-(methylthio) phenyl)propanoic acid, 2-amino-3-(4-hydroxy-3-iodophenyl)propanoic acid, 2-amino-3-(3-chloro-4-hydroxyphenyl) propanoic acid, 2-amino-3-(4-hydroxy-3-methylphenyl) propanoic acid, 2-amino-3-(3-fluoro-4-hydroxyphenyl) propanoic acid, 2-amino-3-(4-hydroxy-3-methoxyphenyl) propanoic acid, 2-amino-3-(3-bromo-4-hydroxyphenyl) propanoic acid, 2-amino-3-(3,5-dichloro-4-hydroxyphenyl) propanoic acid, 2-amino-3-(4-hydroxy-3,5-dimethylphenyl) propanoic acid, 2-amino-3-(2-fluoro-4-hydroxyphenyl) propanoic acid, 2-amino-3-(2-chloro-4-hydroxyphenyl) propanoic acid, 2-amino-3-(4-hydroxy-2-methylphenyl) propanoic acid, 2-amino-3-(2,3,5,6-tetrafluoro-4-hydroxyphenyl)propanoic acid, and 2-amino-3-(4-hydroxynaphthalen-1-yl)butanoic acid.

8. An engineered tryptophan synthase β-subunit (TrpB) comprising the amino acid sequence of any one of SEQ ID NOS: 4-11, wherein the engineered TrpB catalyzes the synthesis of a compound, wherein the compound is tyrosine or a tyrosine analog or a salt thereof.

9. An isolated polynucleotide comprising a nucleotide sequence encoding the engineered TrpB of claim 8.

10. A method for preparing a tyrosine or a tyrosine analog or a salt thereof, the method comprising:
combining in a reaction mixture: (i) a first substrate; (ii) a second substrate; and (iii) an engineered tryptophan synthase β-subunit (TrpB) comprising an amino acid substitution at a position corresponding to amino acid residue E105 of SEQ ID NO: 1; and
maintaining the reaction mixture under conditions sufficient to form the tyrosine or a tyrosine analog or a salt thereof.

11. The method of claim 8, wherein the first substrate is a donor amino acid.

12. The method of claim 9, wherein the donor amino acid is a β-hydroxy amino acid, β-chloroalanine or S-(o-nitrophenyl)-L-cysteine.

13. The method of claim 10, wherein the β-hydroxy amino acid is threonine or serine.

14. The method of claim 10, wherein the β-hydroxy amino acid is L-threonine or L-serine.

15. The method of claim 8, wherein the second substrate is phenol or a phenol analog.

16. The method of claim 10, wherein the tyrosine is L-tyrosine and the tyrosine analog is selected from the group consisting of 2-amino-3-(4-hydroxy-3-(methylthio)phenyl) propanoic acid, 2-amino-3-(4-hydroxy-3-iodophenyl)propanoic acid, 2-amino-3-(3-chloro-4-hydroxyphenyl)propanoic acid, 2-amino-3-(4-hydroxy-3-methylphenyl) propanoic acid, 2-amino-3-(3-fluoro-4-hydroxyphenyl) propanoic acid, 2-amino-3-(4-hydroxy-3-methoxyphenyl) propanoic acid, 2-amino-3-(3-bromo-4-hydroxyphenyl) propanoic acid, 2-amino-3-(3,5-dichloro-4-hydroxyphenyl) propanoic acid, 2-amino-3-(4-hydroxy-3,5-dimethylphenyl) propanoic acid, 2-amino-3-(2-fluoro-4-hydroxyphenyl) propanoic acid, 2-amino-3-(2-chloro-4-hydroxyphenyl) propanoic acid, 2-amino-3-(4-hydroxy-2-methylphenyl) propanoic acid, 2-amino-3-(2,3,5,6-tetrafluoro-4-hydroxyphenyl)propanoic acid, and 2-amino-3-(4-hydroxynaphthalen-1-yl)butanoic acid.

17. The method of claim 15, wherein the phenol analog is selected from the group consisting of 2-(methylthio) phenol, 2-iodophenol, 2-chlorophenol, o-cresol, 2-fluorophenol, 2-bromophenol, 2-methoxyphenol, 2,6-dichlorophenol, 3-fluorophenol, 3-chlorophenol, m-cresol, 2,3,5,6-tetrafluorophenol, naphthalen-1-ol, and 2,6-dimethylphenol.

18. A method of preparing a compound of Formula I, II, or III:

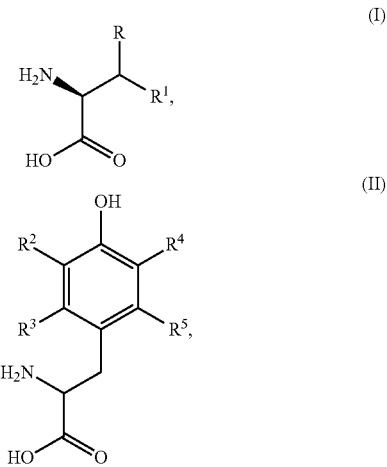

-continued

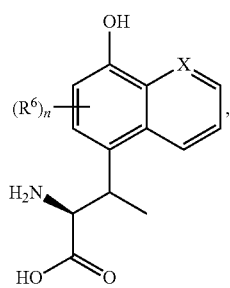
(III)

or a salt thereof,
wherein R is (A), (B), or (C):

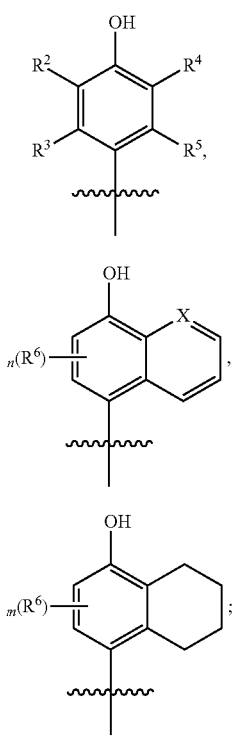

the method comprising:
combining in a reaction mixture: (i) a 3-hydroxy amino acid, (ii) phenol or a phenol analog, and (iii) an engineered tryptophan synthase α-subunit (TrpB) comprising an amino acid subtitution at a position corresponding to amino acids residue E105 of SEQ ID NO: 1; and
maintaining the reaction mixture under conditions sufficient to form the compound according to Formula I, II, or III;
wherein:
$R^1$ is hydrogen or $C_{1-8}$ alkyl, which is optionally substituted with one or more $R^{1a}$;
each $R^{1a}$ is independently selected from the group consisting of hydrogen, halogen, —OH, —CN, —$N_3$, —$NO_2$, $C_{1-12}$ alkyl, $C_{6-14}$ aryl, $C_{2-12}$ alkenyl, $C_{1-12}$ alkynyl, $C_{1-12}$ alkoxy, $C_{1-12}$ thioalkoxy, —$N(R^{1b})_2$, —$C(O)R^{1c}$, —$C(O)N(R^{1b})_2$, —$NR^{1b}C(O)R^{1c}$, and —$OC(O)R^{1c}$;

each $R^{1b}$ is independently selected from the group consisting of hydrogen and $C_{1-6}$ alkyl;
each $R^{1c}$ is independently selected from the group consisting of hydrogen, —OH, halogen, $C_{1-6}$ alkyl, $C_{1-6}$ alkoxy;
$R^2$, $R^3$, $R^4$, and $R^5$ are independently selected from the group consisting of hydrogen, halogen, $C_{1-8}$ alkyl, which is optionally substituted with one or more $R^{2a}$;
each $R^{2a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —$N(R^{2b})_2$, —$C(O)R^{2c}$, —$C(O)N(R^{2b})_2$, —$NR^{2b}C(O)R^{2c}$, and —$OC(O)R^{2c}$;
each $R^{2b}$ is independently selected from the group consisting of hydrogen and $C_{1-6}$ alkyl;
each $R^{2c}$ is independently selected from the group consisting of hydrogen, —OH, halogen, $C_{1-6}$ alkyl, $C_{1-6}$ alkoxy;
$R^6$ is hydrogen or $C_{1-8}$ alkyl, which is optionally substituted with one or more $R^{3a}$;
each $R^{3a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —$N(R^{3b})_2$, —$C(O)R^{3c}$, —$C(O)N(R^{3b})_2$, —$NR^{3b}C(O)R^{3c}$, and —$OC(O)R^{3c}$;
each $R^{3b}$ is independently selected from the group consisting of hydrogen and $C_{1-6}$ alkyl;
each $R^{3c}$ is independently selected from the group consisting of hydrogen, —OH, halogen, $C_{1-6}$ alkyl, $C_{1-6}$ alkoxy;
n is selected from 0, 1, 2, 3, 4, or 5;
m is selected from 0, 1, 2, 3, 4, 5, or 6;
X is —$C(R^7)$ or —N;
wherein $R^7$ is hydrogen or $C_{1-8}$ alkyl, which is optionally substituted with one or more $R^{4a}$;
each $R^{4a}$ is independently selected from the group consisting of hydrogen, halogen, —OH, —CN, —$N_3$, —$NO_2$, $C_{1-12}$ alkyl, $C_{2-12}$ alkenyl, $C_{1-12}$ alkynyl, $C_{1-12}$ alkoxy, $C_{1-12}$ thioalkoxy, —$N(R^{4b})_2$, —$C(O)R^{4c}$, —$C(O)N(R^{4b})_2$, —$NR^{4b}C(O)R^{4c}$, and —$OC(O)R^{4c}$;
each $R^{4b}$ is independently selected from the group consisting of hydrogen and $C_{1-6}$ alkyl; and
each $R^{4c}$ is independently selected from the group consisting of hydrogen, —OH, halogen, $C_{1-6}$ alkyl, $C_{1-6}$ alkoxy.

19. The method of claim 18, wherein the engineered TrpB is a thermophilic TrpB.

20. The method of claim 19, wherein the thermophilic TrpB is selected from the group consisting of T. maritima TrpB, a P. furiosis TrpB, an A. fulgidus Trp. B, a T. naphthophila TrpB, a T. petrophila TrpB, a T. neapolitana TrpB, a C. subterraneus TrpB, a D. tunisiensi TrpB, a D. kuznetsovii TrpB, a P. mobilis TrpB, an A. aeolicus TrpB, an S. azorense TrpB, a T. pseudethanolicus TrpB, a T. thermophilus TrpB, a P. abyssi TrpB, an M. jannaschii TrpB, a T. kodakarensis TrpB, and an M. aeolicus TrpB.

21. The method of claim 18, wherein the reaction mixture is maintained at a temperature ranging from about 20° C. to about 80° C.

22. The method of claim 18, wherein $R^1$ is hydrogen or $C_{1-8}$ alkyl.

23. The method of claim 18, wherein the compound has a structure selected from the group consisting of:

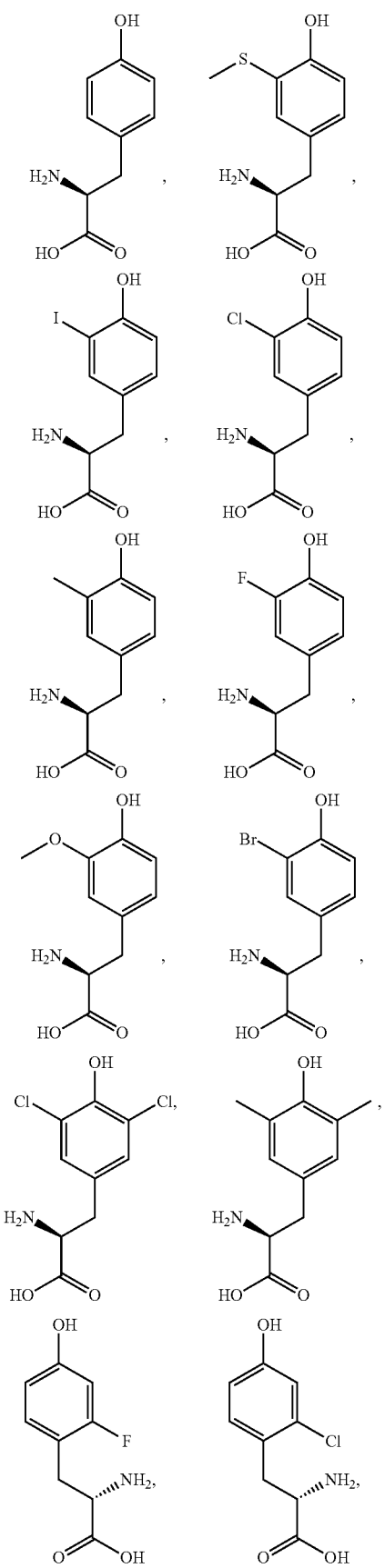

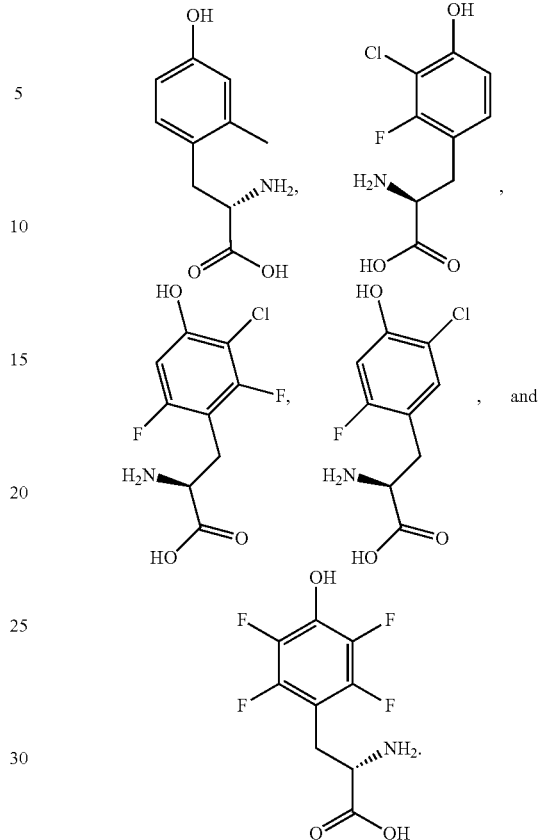

24. The method of claim 18, wherein the compound has the structure:

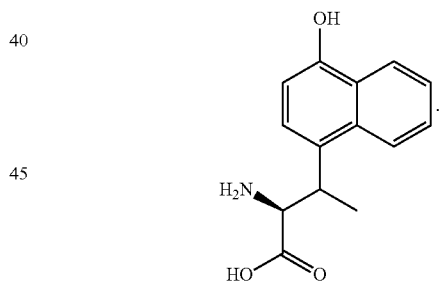

25. An engineered tryptophan synthase β-subunit (TrpB) comprising an amino acid substitution at a position corresponding to amino acid residue E105 of SEQ ID NO: 1 selected from the group consisting of serine (S) and proline (P).

26. The engineered TrpB of claim 25, further comprising one or more amino acid substitutions at a position corresponding to an amino acid residue selected from the group consisting of F41, A87, I103, K139, A150, L170, I174, H191, V227, G229, S265, W286, V291, S302, and R389 of SEQ ID NO: 1.

27. The engineered TrpB of claim 26, wherein: the amino acid substitution at the position corresponding to amino acid residue F41 is Y; the amino acid substitution at the position corresponding to amino acid residue A87 is T; the amino acid substitution at the position corresponding to amino acid residue I103 is T; the amino acid substitution at the position corresponding to amino acid residue K139 is R; the amino acid substitution at the position corresponding to amino acid residue A150 is V; the amino acid substitution at the position corresponding to amino acid residue L170 is F; the amino acid substitution at the position corresponding to amino acid residue I174 is T; the amino acid substitution at the position corresponding to amino acid residue I184 is P or A; the amino acid substitution at the position corresponding to amino acid residue H191 is Y; the amino acid substitution at the position corresponding to amino acid residue V227 is M; the amino acid substitution at the position corresponding to amino acid residue G229 is A; the amino acid substitution at the position corresponding to amino acid residue S265 is P; the amino acid substitution at the position corresponding to amino acid residue W286 is G; the amino acid substitution at the position corresponding to amino acid residue V291 is A; the amino acid substitution at the position corresponding to amino acid residue S302 is P; or the amino acid substitution at the position corresponding to amino acid residue R3 89 is H.

* * * * *

SEQUENCE LISTING

```
Sequence total quantity: 19
SEQ ID NO: 1              moltype = AA  length = 391
FEATURE                   Location/Qualifiers
REGION                    1..391
                          note = Description of sequence: Enzyme: TrpB
source                    1..391
                          mol_type = protein
                          organism = Thermotoga maritima
SEQUENCE: 1
MKGYFGPYGG QYVPEILMPA LEELEAAYEE IMKDESFWKE FNDLLRDYAG RPTPLYFARR   60
LSEKYGARIY LKREDLLHTG AHKINNAIGQ VLLAKKMGKT RIIAETGAGQ HGVATATAAA  120
LFGMECVIYM GEEDTIRQKP NVERMKLLGA KVVPVKSGSR TLKDAINEAL RDWITNLQTT  180
YYVIGSVVGP HPYPIIVRNF QKVIGEETKK QILEKEGRLP DYIVACVGGG SNAAGIFYPF  240
IDSGVKLIGV EAGGEGLETG KHAASLLKGK IGYLHGSKTF VLQDDWGQVQ VTHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIRL E                                391

SEQ ID NO: 2              moltype = AA  length = 391
FEATURE                   Location/Qualifiers
REGION                    1..391
                          note = Description of sequence: Enzyme: Tm9D8
source                    1..391
                          mol_type = protein
                          organism = synthetic construct
SEQUENCE: 2
MKGYFGPYGG QYVPEILMGA LEELEAAYEG IMKDESFWKE FNDLLRDYAG RPTPLYFARR   60
LSEKYGARVY LKREDLLHTG AHKINNAIGQ VLLAKLMGKT RIIAETGAGQ HGVATATAAA  120
LFGMECVIYM GEEDTIRQKL NVERMKLLGA KVVPVKSGSR TLKDAIDEAL RDWITNLQTT  180
YYVIGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIRL E                                391

SEQ ID NO: 3              moltype = AA  length = 391
FEATURE                   Location/Qualifiers
REGION                    1..391
                          note = Description of sequence: Enzyme: Tm9D8*
source                    1..391
                          mol_type = protein
                          organism = synthetic construct
SEQUENCE: 3
MKGYFGPYGG QYVPEILMGA LEELEAAYEG IMKDESFWKE FNDLLRDYAG RPTPLYFARR   60
LSEKYGARVY LKREDLLHTG AHKINNAIGQ VLLAKLMGKT RIIAETGAGQ HGVATATAAA  120
LFGMECVIYM GEEDTIRQKL NVERMKLLGA KVVPVKSGSR TLKDAIDEAL RDWITNLQTT  180
YYVFGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIRL E                                391

SEQ ID NO: 4              moltype = AA  length = 391
FEATURE                   Location/Qualifiers
REGION                    1..391
                          note = Description of sequence: Enzyme: Tm9D8* E105G
source                    1..391
                          mol_type = protein
                          organism = synthetic construct
SEQUENCE: 4
MKGYFGPYGG QYVPEILMGA LEELEAAYEG IMKDESFWKE FNDLLRDYAG RPTPLYFARR   60
LSEKYGARVY LKREDLLHTG AHKINNAIGQ VLLAKLMGKT RIIAGTGAGQ HGVATATAAA  120
LFGMECVIYM GEEDTIRQKL NVERMKLLGA KVVPVKSGSR TLKDAIDEAL RDWITNLQTT  180
YYVFGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIRL E                                391
```

```
SEQ ID NO: 5              moltype = AA  length = 391
FEATURE                   Location/Qualifiers
REGION                    1..391
                          note = Description of sequence: Enzyme: Tm9D8* E105G F184P
source                    1..391
                          mol_type = protein
                          organism = synthetic construct
SEQUENCE: 5
MKGYFGPYGG QYVPEILMGA LEELEAAYEG IMKDESFWKE FNDLLRDYAG RPTPLYFARR   60
LSEKYGARVY LKREDLLHTG AHKINNAIGQ VLLAKLMGKT RIIAGTGAGQ HGVATATAAA  120
LFGMECVIYM GEEDTIRQKL NVERMKLLGA KVVPVKSGSR TLKDAIDEAL RDWITNLQTT  180
YYVPGSVVGP HPYPIIVRNF QKVIGEETKK QIPEKEGRLP DYIVACVSGG SNAAGIFYPF  240
IDSGVKLIGV EAGGEGLETG KHAASLLKGK IGYLHGSKTF VLQDDWGQVQ VSHSVSAGLD  300
YSGVGPEHAY WRETGKVLYD AVTDEEALDA FIELSRLEGI IPALESSHAL AYLKKINIKG  360
KVVVVNLSGR GDKDLESVLN HPYVRERIRL E                                391

SEQ ID NO: 6              moltype = AA  length = 391
FEATURE                   Location/Qualifiers
REGION                    1..391
                          note = Description of sequence: Enzyme: TmTyrS1
source                    1..391
                          mol_type = protein
                          organism = synthetic construct
SEQUENCE: 6
MKGNFGPYGG QNVPEILMGA LEELEAAYEG IMKDESFWKE YNDLLRDYAG RPTPLYFARR   60
LSEKYGARVY LKREDLLHTG AHKINNAIGQ VLLAKLMGKT RIAGTGAGQ HGVATATAAA   120
LFGMECVIYM GEEDTIRQKL NVERMKLLGA KVVPVKSGSR TLKDAIDEAL RDWITNLQTT  180
YYVPGSVVGP HPYPIIVRNF QKVIGEETKK QIPEKEGRLP DYIVACVSGG SNAAGIFYPF  240
IDSGVKLIGV EAGGEGLETG KHAASLLKGK IGYLHGSKTF VLQDDWGQVQ ASHSVSAGLD  300
YPGVGPEHAY WRETGKVLYD AVTDEEALDA FIELSRLEGI IPALESSHAL AYLKKINIKG  360
KVVVVNLSGR GDKDLESVLN HPYVRERIHL E                                391

SEQ ID NO: 7              moltype = AA  length = 391
FEATURE                   Location/Qualifiers
REGION                    1..391
                          note = Description of sequence: Enzyme: TmTyrS2
source                    1..391
                          mol_type = protein
                          organism = synthetic construct
SEQUENCE: 7
MKGNFGPYGG QNVPEILMGA LEELEAAYEG IMKDESFWKE YNDLLRDYAG RPTPLYFARR   60
LSEKYGARVY LKREDLLHTG AHKINNTIGQ VLLAKLMGKT RIAGTGAGQ HGVATATAAA   120
LFGMECVVYM GEEDTIRQKL NVERMKLLGA KVVPVKSGSR TLKDAIDEAL RDWITNLQTT  180
YYVPGSVVGP YPYPIIVRNF QKVIGEETKK QIPEKEGRLP DYIVACVSGG SNAAGIFYPF  240
IDSGVKLIGV EAGGEGLETG KHAASLLKGK IGYLHGSKTF VLQDDWGQVQ ASHSVSAGLD  300
YPGVGPEHAY WRETGKVLYD AVTDEEALDA FIELSRLEGI IPALESSHAL AYLKKINIKG  360
KVVVVNLSGR GDKDLESVLN HPYVRERIHL E                                391

SEQ ID NO: 8              moltype = AA  length = 391
FEATURE                   Location/Qualifiers
REGION                    1..391
                          note = Description of sequence: Enzyme: TmTyrS3
source                    1..391
                          mol_type = protein
                          organism = synthetic construct
SEQUENCE: 8
MKGNFGPYGG QNVPEILMGA LEELEAAYEG IMKDESFWKE YNDLLRDYAG RPTPLYFARR   60
LSEKYGARVY LKREDLLHTG AHKINNTIGQ VLLAKLMGKT RIAGTGAGQ HGVATATAAA   120
LFGMECVVYM GEEDTIRQKL NVERMKQLGA KVVPVKSGSR TLKDAIDEAL RDWITNLQTT  180
YYVPGSVVGP YPYPIIVRNF QKVIGEETKK QIPEKEGRLP DYIVACMSGG SNAAGIFYPF  240
IDSGVKLIGV EAGGEGLETG KHAASLLKGK IGYLHGSKTF VLQDDWGQVQ ASHSVSAGLD  300
YPGVGPEHAY WRETGKVLYD AVTDEEALDA FIELSRLEGI IPALESSHAL AYLKKINIKG  360
KVVVVNLSGR GDKDLESVLN HPYVRERIHL E                                391

SEQ ID NO: 9              moltype = AA  length = 391
FEATURE                   Location/Qualifiers
REGION                    1..391
                          note = Description of sequence: Enzyme: TmTyrS4
source                    1..391
                          mol_type = protein
                          organism = synthetic construct
SEQUENCE: 9
MKGNFGPYGG QNVPEILMGA LEELEAAYEG IMKDESFWKE YNDLLRDYAG RPTPLYFARR   60
LSEKYGARVY LKREDLLHTG AHKINNTIGQ VLLAKLMGKT RIAGTGAGQ HGVATATAAA   120
LFGMECVVYM GEEDTIRQKL NVERMKQLGA KVVPVKSGSR TLKDAIDEAL RDWTTNLQTT  180
YYVAGSVVGP YPYPIIVRNF QKVIGEETKK QIPEKEGRLP DYIVACMSGG SNAAGIFYPF  240
IDSGVKLIGV EAGGEGLETG KHAAPLLKGK IGYLHGSKTF VLQDDWGQVQ ASHSVSAGLD  300
YPGVGPEHAY WRETGKVLYD AVTDEEALDA FIELSRLEGI IPALESSHAL AYLKKINIKG  360
KVVVVNLSGR GDKDLESVLN HPYVRERIHL E                                391
```

```
SEQ ID NO: 10            moltype = AA   length = 391
FEATURE                  Location/Qualifiers
REGION                   1..391
                         note = Description of sequence: Enzyme: TmTyrS5
source                   1..391
                         mol_type = protein
                         organism = synthetic construct
SEQUENCE: 10
MKGNFGPYGG QNVPEILMGA LEELEAAYEG IMKDESFWKE YNDLLRDYAG RPTPLYFARR    60
LSEKYGARVY LKREDLLHTG AHKINNTIGQ VLLAKLMGKT RITAGTGAGQ HGVATATAAA   120
LFGMECVVYM GEEDTIRQKL NVERMKQLGV KVVPVKSGSR TLKDAIDEAL RDWTTNLQTT   180
HYVAGSVVGP YPYPIIVRNF QKVIGEETKK QIPEKEGRLP DYIVACMSAG SNAAGIFYPF   240
IDSGVKLIGV EAGGEGLETG KHAASLLKGK IGYLHGSKTF VLQDDWGQVQ ASHSVSAGLD   300
YPGVGPEHAY WRETGKVLYD AVTDEEALDA FIELSRLEGI IPALESSHAL AYLKKINIKG   360
KVVVVNLSGR GDKDLESVLN HPYVRERIHL E                                 391

SEQ ID NO: 11            moltype = AA   length = 391
FEATURE                  Location/Qualifiers
REGION                   1..391
                         note = Description of sequence: Enzyme: TmTyrS6
source                   1..391
                         mol_type = protein
                         organism = synthetic construct
SEQUENCE: 11
MKGNFGPYGG QNVPEILMGA LEELEAAYEG IMKDESFWKE YNDLLRDYAG RPTPLYFARR    60
LSEKYGARVY LKREDLLHTG AHKINNTIGQ VLLAKLMGKT RITAGTGAGQ HGVATATAAA   120
LFGMECVVYM GEEDTIRQRL NVERMKQLGV KVVPVKSGSR TLKDAIDEAF RDWTTNLQTT   180
HYVAGSVVGP YPYPIIVRNF QKVIGEETKK QIPEKEGRLP DYIVACMSAG SNAAGIFYPF   240
IDSGVKLIGV EAGGEGLETG KHAASLLKGK IGYLHGSKTF VLQDDWGQVQ ASHSVSAGLD   300
YPGVGPEHAY WRETGKVLYD AVTDEEALDA FIELSRLEGI IPALESSHAL AYLKKINIKG   360
KVVVVNLSGR GDKDLESVLN HPYVRERIHL E                                 391

SEQ ID NO: 12            moltype = AA   length = 390
FEATURE                  Location/Qualifiers
REGION                   1..390
                         note = Description of sequence: Enzyme: Pf2B9
source                   1..390
                         mol_type = protein
                         organism = synthetic construct
SEQUENCE: 12
MWFGEFGGQY VPETLVGPLK ELEKAYKRFK DDEEFNRQLN YYLKTWAGRP TPLYYAKRLT    60
EKIGGAKVYL KREDLVHGGA HKTNNAIGQA LLAKLMGKTR LIAETGAGQH GVATAMAGAL   120
LGMKVDIYMG AEDVERQKMN VFRMKLLGAN VIPVNSGSRT LKDAINEALR DWVATFEYTH   180
YLIGSVVGPH PYPTIVRDFQ SVIGREAKAQ ILEAEGQLPD VIVACVGGGS NAMGIFYPFV   240
NDKKVKLVGV EAGGKGLESG KHSASLNAGQ VGVSHGMLSY FLQDEEGQIK PSHSIAPGLD   300
YPGVGPEHAY LKKIQRAEYV AVTDEEALKA FHELSRTEGI IPALESAHAV AYAMKLAKEM   360
SRDEIIIVNL SGRGDKDLDI VLKASGNVLE                                   390

SEQ ID NO: 13            moltype = AA   length = 390
FEATURE                  Location/Qualifiers
REGION                   1..390
                         note = Description of sequence: Enzyme: Pf2B9 E104G
source                   1..390
                         mol_type = protein
                         organism = synthetic construct
SEQUENCE: 13
MWFGEFGGQY VPETLVGPLK ELEKAYKRFK DDEEFNRQLN YYLKTWAGRP TPLYYAKRLT    60
EKIGGAKVYL KREDLVHGGA HKTNNAIGQA LLAKLMGKTR LIAGTGAGQH GVATAMAGAL   120
LGMKVDIYMG AEDVERQKMN VFRMKLLGAN VIPVNSGSRT LKDAINEALR DWVATFEYTH   180
YLIGSVVGPH PYPTIVRDFQ SVIGREAKAQ ILEAEGQLPD VIVACVGGGS NAMGIFYPFV   240
NDKKVKLVGV EAGGKGLESG KHSASLNAGQ VGVSHGMLSY FLQDEEGQIK PSHSIAPGLD   300
YPGVGPEHAY LKKIQRAEYV AVTDEEALKA FHELSRTEGI IPALESAHAV AYAMKLAKEM   360
SRDEIIIVNL SGRGDKDLDI VLKASGNVLE                                   390

SEQ ID NO: 14            moltype = AA   length = 465
FEATURE                  Location/Qualifiers
REGION                   1..465
                         note = Description of sequence: Enzyme:  UniProt Reference
                         ID: F4K727_ARATH: Exemplary TrpB A105
source                   1..465
                         mol_type = protein
                         organism = synthetic construct
SEQUENCE: 14
MSSSKIQVRG QPLLRVPARN HRMTHLVVCG VSTKRHHREI NALSSNSGPS LDSVPTRTDK    60
RQFLRGDGNG KFGRFGGKFV PETLMSRLIE LEDEFNFVRC DHEFQEELTT ALRDYVGRET   120
PLYFAERLTE HYKNIVPTIE GGPEIYLKRE DLSHCGSHKI NNALAQAMIS RRLGCSRVVA   180
ATGAGQHGVA TAAACAKLSL ECTVFMGAAD IEKQSFNVLS MKLLGAQVIS VEGTFKDASS   240
EAIRNWVENL YTTYYLSGTV VGPHPCPIIV REFQSVIGKE TRRQAKQLWG GKPDVLACV   300
```

```
GSGSNALGLF HEFVGDEDVR LVGVEAAGLG LDSGKHSATL AFGDVGVYHG SMSYLLQDDQ    360
GQILKPHSVG VGLEYPGVGP EISFMKETGR AEFYTATDEE AIQACMRLSR LEGIIPALEA   420
SHALAFLDKL VPTLRDGAKV VVNCSGRGDK DLDTLIQRGM PSSFC                   465

SEQ ID NO: 15           moltype = AA  length = 463
FEATURE                 Location/Qualifiers
REGION                  1..463
                        note = Description of sequence: Enzyme:  UniProt Reference
                          ID: A0A059W1L0_STRA9: Exemplary TrpB G105
source                  1..463
                        mol_type = protein
                        organism = synthetic construct
SEQUENCE: 15
MMNSAEASLT AEEIVPTHWY NVLSDLSGVE DAAKLRQARP ETRTDGDAVA PQIPLSMYRQ    60
SMGRERFVEI PQEVRAEYLR WRPTPLKRAR RLEQLLDTPA RIYYKYEGTN TTGSHKLNTA   120
LAQAYYYKQA GITSLTTGTG AGQWGSALAV ACRIFGLECT VYMVRVSYDQ KPYRRIMMEM   180
NGAKVISSPN ENSEAGRAAL ARDPNTDGSL SIANAEAFEH ARQVERCNLS VGSGENHVLL   240
HQTVIGQEAV RQFRAIGDFP DVVIGSVGAG SNFSGVSLPF FHEKVREGLD TRFVAVEPEA   300
CPKLTKGRYA WDYNDYTGIT PMTKMYTLGH TFVSPGIHAG GLRYHGAAPL VSAMYHQKLI   360
EAVAYPQRSV FEAGITFAHE EGLIPAPESA HAIRGAIEEA LLAKKEGREK VILFNLSGHG   420
LLDLSAYQQF LSGNMTDMAA SDEAIAASLG RLPAMDDLGA AAH                    463

SEQ ID NO: 16           moltype = DNA  length = 41
FEATURE                 Location/Qualifiers
source                  1..41
                        mol_type = other DNA
                        organism = unidentified
SEQUENCE: 16
gaaataattt tgtttaactt taagaaggag atatacatat g                       41

SEQ ID NO: 17           moltype = DNA  length = 35
FEATURE                 Location/Qualifiers
source                  1..35
                        mol_type = genomic DNA
                        organism = unidentified
SEQUENCE: 17
gccggatctc agtggtggtg gtggtggtgc tcgag                              35

SEQ ID NO: 18           moltype = DNA  length = 54
FEATURE                 Location/Qualifiers
source                  1..54
                        mol_type = unassigned DNA
                        organism = unidentified
SEQUENCE: 18
ccaacttact tctgacaacg atcggaggac cgaaggagct aaccgctttt ttgc          54

SEQ ID NO: 19           moltype = DNA  length = 54
FEATURE                 Location/Qualifiers
source                  1..54
                        mol_type = unassigned DNA
                        organism = unidentified
SEQUENCE: 19
cgatcgttgt cagaagtaag ttggccgcag tgttatcact catggttatg gcag          54
```